(12) United States Patent
Nakamura et al.

(10) Patent No.: US 6,835,844 B2
(45) Date of Patent: Dec. 28, 2004

(54) ACRYLIC ESTERS AND USE THEREOF

(75) Inventors: Mitsuo Nakamura, Sodegaura (JP); Masao Imai, Sodegaura (JP); Atsuo Otsuji, Sodegaura (JP)

(73) Assignee: Mitsui Chemicals, Inc., Tokyo (JP)

( * ) Notice: Subject to any disclaimer, the term of this patent is extended or adjusted under 35 U.S.C. 154(b) by 136 days.

(21) Appl. No.: 10/332,742

(22) PCT Filed: May 15, 2002

(86) PCT No.: PCT/JP02/04695

§ 371 (c)(1),
(2), (4) Date: Jan. 13, 2003

(87) PCT Pub. No.: WO02/092591

PCT Pub. Date: Nov. 21, 2002

(65) Prior Publication Data

US 2004/0102592 A1 May 27, 2004

(30) Foreign Application Priority Data

| May 15, 2001 | (JP) | ........................ | 2001-144539 |
| May 15, 2001 | (JP) | ........................ | 2001-144540 |
| Sep. 3, 2001 | (JP) | ........................ | 2001-266422 |
| Sep. 17, 2001 | (JP) | ........................ | 2001-281859 |

(51) Int. Cl.$^7$ ........................ C07D 339/02; C08F 28/06
(52) U.S. Cl. ........................ 549/35; 549/39; 526/259
(58) Field of Search ........................ 549/35, 39; 526/259

(56) References Cited

U.S. PATENT DOCUMENTS

| 4,465,845 A | * | 8/1984 | Okamoto et al. | ............. 549/30 |
| 4,600,784 A | * | 7/1986 | Okamoto et al. | ............. 549/39 |
| 6,458,908 B1 | * | 10/2002 | Imai et al. | ............. 526/259 |
| 6,570,025 B1 | * | 5/2003 | Fujii et al. | ............. 549/11 |

FOREIGN PATENT DOCUMENTS

| EP | 1 057 808 A2 | 12/2000 |
| EP | 0 562 966 A2 | 9/2003 |
| JP | 3-215801 A | 9/1991 |
| JP | 4-321662 A | 11/1992 |
| WO | WO 98/35955 A1 | 8/1998 |

* cited by examiner

*Primary Examiner*—Deborah C. Lambkin
(74) *Attorney, Agent, or Firm*—Burns, Doane, Swecker & Mathis, L.L.P.

(57) ABSTRACT

The present invention provides an acrylic ester compound represented by formula (1), a polymerizable composition containing the acrylic ester compound, and a cured product and an optical component obtained by polymerizing the polymerizable composition:

(1)

(wherein "a" is an integer of 0 to 4; $R_1$ is a directly bonded single bond, an alkylene group, an aralkylene group or arylene group which may have a substituent, or a —$Y_3$—S—$R_4$—S—$Y_4$— group ($R_4$ is an alkylene group, an aralkylene group or an arylene group; and $Y_3$ and $Y_4$ are each an alkylene group); $R_2$ and $R_3$ are each a hydrogen atom or an alkyl group; $X_1$ and $X_2$ are each an oxygen atom or a sulfur atom; and $Y_1$ and $Y_2$ are each an alkylene group which may contain an oxygen atom or a sulfur atom).

20 Claims, No Drawings

ACRYLIC ESTERS AND USE THEREOF

TECHNICAL FIELD

The present invention relates to an acrylic ester compound, a polymerizable composition containing the acrylic ester compound, and a cured product and an optical component obtained by polymerizing the polymerizable composition. Furthermore, it also relates to a sulfur-containing compound useful as a starting material at the time of manufacture of the acrylic ester compound.

BACKGROUND ART

Inorganic glass has been widely used in various fields as a transparent optical material, because of its favorable properties such as high transparency and low optical anisotropy. However, it has disadvantages of being heavy, fragile and poor in productivity. Therefore, various organic optical materials (optical resins) have been extensively developed to replace the inorganic glass.

One of the basically most important characteristics for an optical resin is transparency. The highly transparent optical resins developed so far include polymethyl methacrylate (PMMA), bisphenol A polycarbonate (BPA-PC), polystyrene (PS), methyl methacrylate/styrene copolymer (MS), styrene/acrylonitrile copolymer (SAN), poly(4-methyl-pent-1-ene) (TPX), polycycloolefin (COP), polydiethylene glycol bisallyl carbonate (EGAC) and polythiourethane (PTU).

PMMA has excellent transparency and weather resistance as well as good moldability. However, it has disadvantages of low refractive index (nd) of 1.49 and high moisture absorptivity.

BPA-PC is excellent in transparency, heat resistance, impact resistance and refractive index. However, it has disadvantages of relatively high optical anisotropy (birefringence) and high aberration (low Abbe number), which have limited its applications.

PS and MS have high moldability, high transparency, low moisture absorptivity and high refractive index. However, they have been rarely used as optical resins, because of their disadvantages of insufficient resistance to impact, weather and heat.

SAN is relatively high in refractive index, and considered to have balanced mechanical properties. However, it is also rarely used as an optical resin, because of its relatively insufficient heat resistance (thermal deformation temperature: 80 to 90° C.).

TPX and COP, although having high transparency, low moisture absorptivity and high heat resistance, include disadvantages of low refractive index (nd: 1.47 to 1.53), and insufficient impact resistance, gas barrier characteristics and dye-affinity.

EGAC is a thermosetting optical resin produced by polymerization of diethylene glycol bisallyl carbonate as a monomer, and has been most widely used for common spectacles lenses. It has favorable characteristics of high transparency, high heat resistance and very low chromatic aberration, but disadvantages of low refractive index (nd: 1.50) and insufficient impact resistance.

PTU is a thermosetting resin obtained by a reaction between a diisocyanate compound and a polythiol compound, and most widely used for spectacles lenses of superhigh refractive index. PTU is a very excellent optical resin having, in particular, high transparency and impact resistance as well as a high refractive index and low chromatic aberration. However, it inconveniently needs a long time for molding by thermal polymerization (1 to 3 days), and hence involves productivity-related problems to be solved.

Some of the proposals for improved productivity by decreasing a polymerization/molding time include use of acrylates or thioacrylates containing a bromine atom or a sulfur atom for radical polymerization initiated by being irradiated with light to obtain optical lenses, as disclosed by Japanese Patent Laid-open Publication Nos. 63-248811, 1-266613 and 3-217412. Moreover, use of (meth)acrylate compounds having a sulfur-containing alicyclic structure as a radical-polymerizable compound is also suggested for production of the optical lenses by Japanese Patent Laid-open Publication Nos. 3-215801 and 4-161410.

However, the resins produced, by these methods, although being able to be polymerized in a shorter time, rarely satisfy characteristics sufficient for optical lenses, which include optical characteristics (e.g., transparency, refractive index and Abbe number), thermal characteristics (e.g., thermal deformation temperature) and mechanical characteristics (e.g., impact resistance and bending strength). More specifically, when these resins are used for spectacles lenses, they have various disadvantages of, e.g., insufficient refractive index, low Abbe number though being high in refractive index, being fragile and easily broken, and being heavy for the lenses, and in addition, the surfaces of the resins are roughened or attacked by a solvent which is used for treatment, e.g., for providing a hard coat. Therefore, developments of the materials which can solve these problems have been greatly demanded.

As described above, each of the conventional optical resins involves disadvantages and problems to be solved, though having excellent characteristics. Under these circumstances, there are keen demands for development of novel optical materials which are excellent in productivity because of being polymerizable and moldable in a short time, good in thermal and mechanical characteristics, and high in refractive index and Abbe number.

DISCLOSURE OF THE INVENTION

It is an object of the present invention to provide an optical resin, which can be polymerizable and moldable in a short time so that it is excellent in productivity, having good thermal and mechanical characteristics, and being high in refractive index by solving the problems involved in the conventional optical resin.

The present inventors have achieved the present invention after having extensively studied to solve the above-described problems. That is, the present invention provides:

[1] An acrylic ester compound represented by formula (1):

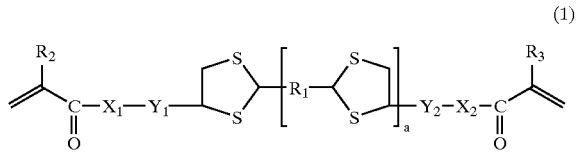

(wherein
"a", is an integer of 0 to 4;
$R_1$ is a directly bonded single bond, an alkylene group which may have a substituent, an aralkylene group which may have a substituent, an arylene group which may have a substituent, or a $—Y_3—S—R_4—S—Y_4—$ group;

$R_2$ and $R_3$ are each a hydrogen atom or an alkyl group;

$X_1$ and $X_2$ are each an oxygen atom or a sulfur atom;

$Y_1$ and $Y_2$ are each an alkylene group which may contain an oxygen atom or a sulfur atom;

$R_4$ in the $—Y_3—S—R_4—S—Y_4—$ group is an alkylene group, an aralkylene group or an arylene group; and $Y_3$ and $Y_4$ in the $—Y_3—S—R_4—S—Y_4—$ group are each independently an alkylene group.

[2] The acrylic ester compound according to [1], wherein in formula (1), "a" is 1; $R_1$ is a directly bonded single bond, an alkylene group which may have a substituent, an aralkylene group which may have a substituent, an arylene group which may have a substituent or a $—Y_3—S—R_4—S—Y_4—$ group (wherein $Y_3$ is a $—(CH_2)_m—$ group and $Y_4$ is a $—(CH_2)_n—$ group ("m" and "n" are each an integer of 1 to 4)); and $Y_1$ is a $—(CH_2)_k—$ group and $Y_2$ is a $—(CH_2)_l—$ group ("k" and "l" are each an integer of 1 to 4).

[3] The acrylic ester compound according to [1], wherein in formula (1), "a" is 0; and $Y_1$ is a $—(CH_2)_k—$ group and $Y_2$ is a $—(CH_2)_l—$ group ("k" and "l" are each an integer of 1 to 4).

[4] The acrylic ester compound according to [2], wherein the compound represented by formula (1) is represented by formula (1-a):

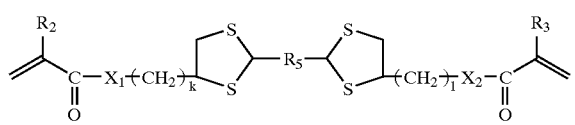

(1-a)

(wherein $R_5$, which is similar to $R_1$, is a directly bonded single bond, an alkylene group which may have a substituent, an aralkylene group which may have a substituent, or an arylene group which may have a substituent; and $R_2$, $R_3$, $X_1$, $X_2$, "k" and "l" are same meanings as described above).

[5] The acrylic ester compound according to [2], wherein the compound represented by formula (1) is a compound represented by formula (1-b):

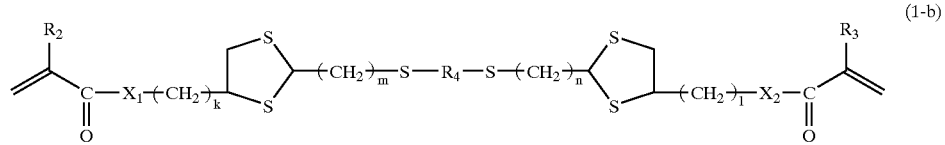

(1-b)

(wherein $R_2$, $R_3$, $R_4$, $X_1$, $X_2$, "k", "l", "m" and "n" are same meanings as described above).

[6] The acrylic ester compound according to [3], wherein the compound represented by formula (1) is a compound represented by formula (1-c):

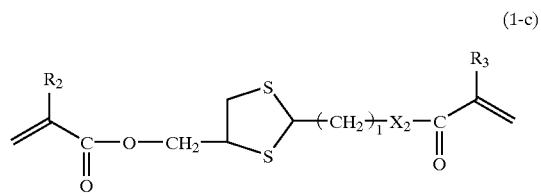

(1-c)

(wherein $R_2$, $R_3$, $R_4$, $X_1$, $X_2$, and "l" are same meanings as described above).

[7] The acrylic ester compound according to [3], wherein the compound represented by formula (1) is a compound represented by formula (1-d):

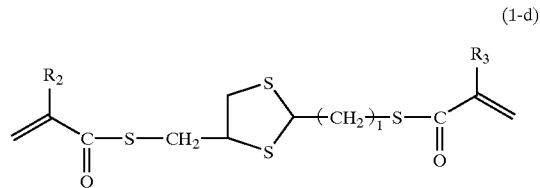

(1-d)

(wherein $R_2$, $R_3$ and "l" are same meanings as described above).

[8] A polymerizable composition containing the acrylic ester compound according to any one of [1] to [7].

[9] A cured product obtained by polymerizing the polymerizable composition according to [8].

[10] An optical component comprising the cured product according to [9].

[11] A process for producing the acrylic ester compound represented by formula (1) in accordance with acrylate-esterification of a sulfur-containing compound represented by formula (2):

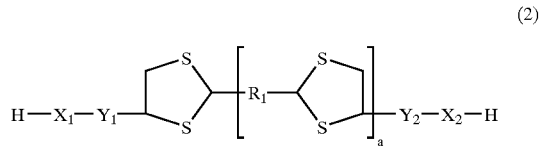

(2)

(wherein "a", $R_1$, $X_1$, $X_2$, $Y_1$ and $Y_2$ are same meanings as described above).

[12] The process according to [11] for producing the acrylic ester compound represented by formula (1), wherein the acrylate-esterification is effected by reacting a halopropionic acid or its acid halide with the compound represented by formula (2) to convert it into a halopropionic ester compound, and then by dehydrohalogenating the halopropionic ester compound into the acrylic ester.

[13] The process according to [11] or [12] for producing the acrylic ester compound, wherein the compound represented by formula (2) is a compound represented by formula (2-a):

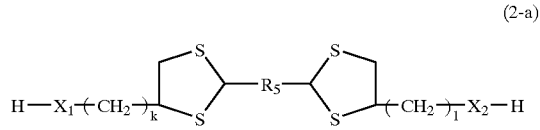

(2-a)

(wherein $R_5$ is a directly bonded single bond, an alkylene group which may have a substituent, an aralkylene group which may have a substituent, or an arylene group which may have a substituent; "k" and "l" are each an integer of 1 to 4; and $X_1$ and $X_2$ are each an oxygen atom or a sulfur atom).

[14] The process according to [11] or [12] for producing the acrylic ester compound, wherein the compound represented by formula (2) is a compound represented by formula (2-b):

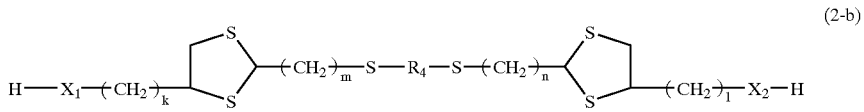

(2-b)

(wherein $R_4$ is an alkylene, an aralkylene or an arylene group; "k", "l", "m" and "n" are each an integer of 1 to 4; and $X_1$ and $X_2$ are each an oxygen atom or a sulfur atom).

[15] The process according to [11] or [12] for producing the acrylic ester compound, wherein the compound represented by formula (2) is a compound represented by formula (2-c):

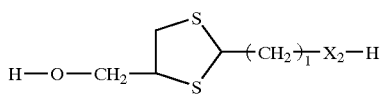

(2-c)

(wherein $X_2$ is an oxygen atom or a sulfur atom; and "l" is an integer of 1 to 4).

[16] The process according to [11] or [12] for producing the acrylic ester compound, wherein the compound represented by formula (2) is a compound represented by formula (2-d):

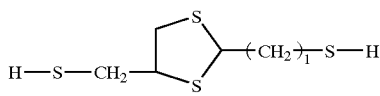

(2-d)

(wherein "l" is an integer of 1 to 4).

[17] A sulfur-containing compound represented by formula (2-a):

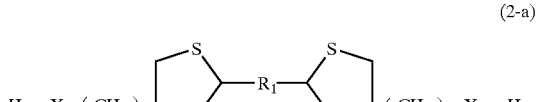

(2-a)

(wherein $R_1$ is a directly bonded single bond, an alkylene group which may have a substituent, an aralkylene group which may have a substituent, or an arylene group which may have a substituent; "k" and "l" are each an integer of 1 to 4; and $X_1$ and $X_2$ are each a sulfur atom or an oxygen atom).

[18] A sulfur-containing compound represented by formula (2-b):

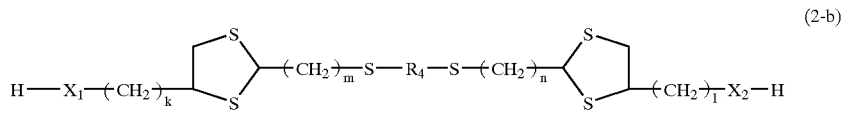

(2-b)

(wherein $R_4$ is an alkylene group, an aralkylene group or an arylene group; "k", "l", "m" and "n" are each an integer of 1 to 4; and $X_1$ and $X_2$ are each an oxygen atom or a sulfur atom).

[19] A sulfur-containing compound represented by formula (2-c):

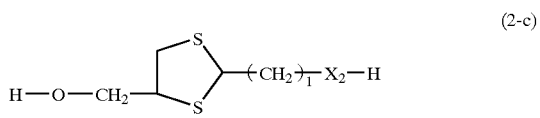

(2-c)

(wherein $X_2$ is an oxygen atom or a sulfur atom; and "l", is an integer of 1 to 4).

[20] A sulfur-containing compound represented by formula (3):

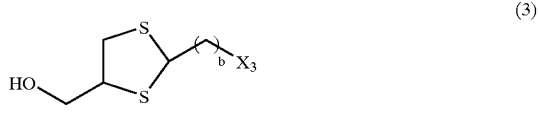

(3)

(wherein $X_3$ is a halogen atom; an "b" is an integer of 1 to 4).

BEST MODE FOR CARRYING OUT THE INVENTION

The present invention will be described in detail.

The acrylic ester compound of the present invention represented by formula (1), is a novel compound characterized by the chemical structure having, per molecule, one or two dithiolan ring structures and two (meth)acryloyl groups.

The acrylic ester compound of the present invention is a novel compound characterized by the chemical structure having, per molecule, one or two dithiolan ring structures and two (meth)acryloyl groups, and useful as a monomer for a polymerizable composition, curable by being initiated for polymerization when irradiated with light:

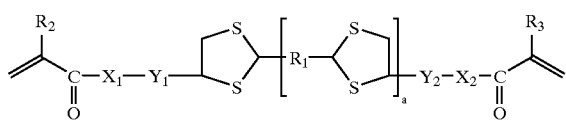

(1)

In formula (1), "a" is an integer of 0 to 4, preferably 0 to 3, more preferably 0 to 2, still more preferably 0 or 1.

In formula (1), $R_1$ is a directly bonded single bond, an alkylene group which may have a substituent, an aralkylene group which may have a substituent, an arylene group which may have a substituent, or a —$Y_3$—S—$R_4$—S—$Y_4$— group (wherein $R_4$ is an alkylene group, an aralkylene group or an arylene group, and $Y_3$ and $Y_4$ are each an alkylene group).

It is preferably a straight-chain, a cyclic alkylene group or their combination of 1 to 20 carbon atoms which may have a substituent; an aralkylene group of 6 to 20 carbon atoms which may have a substituent; an arylene group of 4 to 20 carbon atoms which may have a substituent; or a —$Y_3$—S—$R_4$—S—$Y_4$— group.

When $R_1$ is an alkylene-group which may have a substituent, the substituent for the alkylene group includes alkoxy, alkoxyalkoxy, aralkyloxy, aryloxy, aryloxyalkyloxy, alkylthio, alkylthioalkylthio, aralkylthio, arylthio and arylthioalkylthio groups.

When $R_1$ is an aralkylene group or an arylene group which may have a substituent, the aromatic ring in the aralkylene group or the arylene group is preferably substituted. The substituent includes alkyl, alkoxy, alkoxyalkoxy, aralkyloxy, aryl, aryloxy, aryloxyalkyloxy, alkylthio, alkylthioalkylthio, aralkylthio, arylthio and arylthioalkylthio groups, and a halogen atom.

The aromatic ring in the aralkylene or the arylene group may be a hydrocarbon aromatic ring or a heteroaromatic ring containing a heteroatom. The heteroatom is preferably an oxygen, sulfur or nitrogen atom, more preferably an oxygen or sulfur atom, still more preferably a sulfur atom.

The $R_1$ group is more preferably a directly bonded single bond, a straight-chain, branched or cyclic alkylene group or their combination of 1 to 8 carbon atoms, an aralkylene group of 6 to 12 carbon atoms, an arylene group of 4 to 12 carbon atoms, or a —$Y_3$—S—$R_4$—S—$Y_4$— group, still more preferably the directly bonded single bond, the straight-chain, branched or cyclic alkylene group or their combination of 1 to 4 carbon atoms, the aralkylene group of 6 to 8 carbon atoms, the arylene group of 4 to 10 carbon atoms, or the —$Y_3$—S—$R_4$—S—$Y_4$— group.

$R_4$ in the —$Y_3$—S—$R_4$—S—$Y_4$— group is an alkylene group, an aralkylene group or an arylene group, and $Y_3$ and $Y_4$ in the —$Y_3$—S—$R_4$—S—$Y_4$— group are each an alkylene group.

$R_4$ in the —$Y_3$—S—$R_4$—S—$Y_4$— group is preferably a straight-chain or cyclic alkylene group or their combination of 1 to 20 carbon atoms which may have a substituent; an aralkylene group of 6 to 20 carbon atoms which may have a substituent; or an arylene group of 4 to 20 carbon atoms which may have a substituent.

For the alkylene group which may have a substituent, the substituent includes alkoxy, alkoxyalkoxy, aralkyloxy, aryl, aryloxy, aryloxyalkyloxy, alkylthio, alkylthioalkylthio, aralkylthio, arylthio and arylthioalkylthio groups, and a halogen atom.

For the aralkylene or the arylene group which may have a substituent, the substituent includes alkyl, alkoxy, alkoxyalkoxy, aralkyloxy, aryl, aryloxy, aryloxyalkyloxy, alkylthio, alkylthioalkylthio, aralkylthio, arylthio and arylthioalkylthio groups, and a halogen atom.

The alkylene group may contain a heteroatom, e.g., oxygen or sulfur.

The aromatic ring in the aralkylene or the arylene group may be a hydrocarbon ring or a heteroaromatic ring containing a heteroatom.

The $R_4$ group is more preferably a straight-chain, branched or cyclic alkylene group or their combination of 1 to 8 carbon atoms, an aralkylene group of 6 to 12 carbon atoms, or an arylene group of 4 to 12 carbon atoms, still more preferably a straight-chain, branched or cyclic alkylene group or their combination of 1 to 4 carbon atoms, an aralkylene group of 6 to 8 carbon atoms, or an arylene group of 4 to 10 carbon atoms.

Of these, the particularly preferable $R_4$ group is an alkylene, aralkylene or arylene which is not substituted.

The $R_4$ group includes, but not limited to, methylene, ethylene, ethylidene, trimethylene, 1-methyl-1,2-ethylene, isopropylidene, tetramethylene, ethylethylene, 1-butylidene, 2-butylidene, 1,5-pentamethylene, 1,6-hexamethylene, 1,8-octamethylene, 1,4-cyclohexylene, 1,3-cyclohexylene, 1,2-cyclohexylene, 1,4-cyclohexanebismethyl, 1,3-cyclohexanebismethyl, 1,2-cyclohexanebismethyl, 1,4-cyclohexanebisethyl, 1,3-cyclohexanebisethyl, 1,2-cyclohexanebisethyl, 1,4-xylylene, 1,3-xylylene, 1,2-xylylene, 1,4-(α,α'-dimethyl)xylylene, 1,3-(α,α'-dimethyl)xylylene, 1,2-(α,α'-dimethyl)xylylene, 1,4-(α,α,α',α'-tetramethyl)xylylene, 1,3-(α,α,α',α'-tetramethyl)xylylene, 1,2-(α,α,α'-tetramethyl)xylylene, 1,4-benzenebis-β-ethyl, 1,3-benzenebis-β-ethyl, 1,2-benzenebis-β-ethyl, 1,4-phenylene, 1,3-phenylene, 1,2-phenylene, naphthylene, and thiophen-2,5-diyl groups.

Of these $R_4$ groups, the particularly preferable ones are methylene, ethylene, ethylidene, trimethylene, 1-methyl-1,2-ethylene, isopropylidene, tetramethylene, 1,4-xylylene, 1,3-xylylene, 1,2-xylylene, 1,4-phenylene, 1,3-phenylene, 1,2-phenylene, naphthylene, thiophen-2,5-diyl groups.

$Y_3$ and $Y_4$ in the —$Y_3$—S—$R_4$—S—$Y_4$— group are preferably an alkylene group having a total carbon number of 1 to 8, more preferably $Y_3$ is the one represented by —$(CH_2)_m$— and $Y_4$ is the one represented by —$(CH_2)_n$—, wherein "m" and "n" are each an integer of 1 to 4, preferably 1 to 3, still more preferably 1 or 2, particularly preferably 1.

The $R_1$ group includes, but not limited to, divalent bonding groups, e.g., directly bonded single bond, methylene, dimethylene, ethylidene, trimethylene, 1-methyl-1,2-ethylene, isopropylidene, tetramethylene, ethylethylene, 1-butylidene, 2-butylidene, 1,5-pentamethylene, 1,6-hexamethylene, 1,8-octamethylene, 1,4-cyclohexylene, 1,3-cyclohexylene, 1,2-cyclohexylene, 1,4-cyclohexanedimethyl, 1,3-cyclohexanedimethyl, 1,2-cyclohexanedimethyl, 1,4-cyclohexanediethyl, 1,3-cyclohexanediethyl, 1,2-cyclohexanediethyl, 1,4-xylylene, 1,3-xylylene, 1,2-xylylene, 1,4-(α,α'-dimethyl)xylylene, 1,3-(α,α'-dimethyl)xylylene, 1,2(α,α'-dimethyl)xylylene, 1,4-(α,α,α',α'-tetramethyl)xylylene, 1,3-(α,α,α',α'-tetramethyl)xylylene, 1,2-(α,α,α',α'-tetramethyl)xylylene, 1,4-benzenebis-β-ethyl, 1,3-benzenebis-β-ethyl, 1,2-benzenebis-β-ethyl, 1,4-phenylene, 1,3-phenylene, 1,2-phenylene, 2,3-naphthylene, 2,6-naphthylene, 2,2'-biphenyl, 2,2'-diphenylether, furan-2,5-diyl, thiophen-2,5-diyl;

methane-1,1-bis-thiomethyl, ethane-1,2-bis-thiomethyl, ethane-1,1-bis-thiomethyl, propane-1,3-bis-thiomethyl, 1-methyl-ethane-1,2-bis-thiomethyl, propane-2,2-bis-thiomethyl, butane-1,4-bis-thiomethyl, butane-1,2-bis-thiomethyl, butane-1,1-bis-thiomethyl, butane-2,2-bis-thiomethyl, pentane-1,5-bis-thiomethyl, hexane-1,6-bis-thiomethyl, octane-1,8-bis-thiomethyl, cyclohexane-1,4-bis-thiomethyl, cyclohexane-1,3-bis-thiomethyl, cyclohexane-1,2-bis-thiomethyl, cyclohexane-1,4-bis(methylthiomethyl), cyclohexane-1,3-bis(methylthiomethyl), cyclohexane-1,2-bis(methylthiomethyl), cyclohexane-1,4-bis(ethylthiomethyl), cyclohexane-1,3-bis(ethylthiomethyl), cyclohexane-1,2-bis(ethylthiomethyl), benzene-1,4-bis(methylthiomethyl), benzene-1,3-bis(methylthiomethyl), benzene-1,2-bis(methylthiomethyl), benzene-1,4-bis(α-methyl-methylthiomethyl), benzene-1,3-bis(α-methyl-methylthiomethyl), benzene-1,2-bis(α-methyl-methylthiomethyl), benzene-1,4-bis(α,α-dimethyl-methylthiomethyl), benzene-1,3-bis(α,α-dimethyl-methylthiomethyl), benzene-1,2-bis(α,α-dimethyl-methylthiomethyl), benzene-1,4-bis(β-ethyl), benzene-1,3-bis(β-ethyl), benzene-1,2-bis(β-ethyl), benzene-1,4-bisthiomethyl, benzene-1,3-bisthiomethyl, benzene-1,2-bisthiomethyl, naphthalene-bis-thiomethyl, and thiophene-2,5-bis(thiomethyl) groups.

The particularly preferable $R_1$ group includes a directly bonded single bond, methylene, dimethylene, trimethylene, tetramethylene, 1,4-phenylene, 1,3-phenylene, 1,2-phenylene, naphthylene, thiophen-2,5-diyl, methane-1,1-bis-thiomethyl, ethane-1,2-bis-thiomethyl, propane-1,3-bis-thiomethyl, propane-1,2-bis-thiomethyl, propane-2,2-bis-thiomethyl, butane-1,4-thiomethyl, benzene-1,4-bis(methylthiomethyl), benzene-1,3-bis(methylthiomethyl), benzene-1,2-bis(methylthiomethyl), benzene-1,4-bis(thiomethyl), benzene-1,3-bis(thiomethyl), benzene-1,2-bis(thiomethyl), naphthalene-bis-thiomethyl, and thiophene-2,5-bis-thiomethyl groups.

$R_2$ and $R_3$ in formula (1) are each a hydrogen atom or an alkyl group, preferably a hydrogen atom or an alkyl group of 1 to 4 carbon atoms, more preferably the hydrogen atom or a methyl group.

$Y_1$ and $Y_2$ in formula (1) are each an alkylene group which may contain an oxygen atom or a sulfur atom.

The alkylene group which may contain an oxygen atom or a sulfur atom means that its methylene group may be partly an oxa (—O—) group or a thia (—S—) group. Such an alkylene group which may contain an oxygen atom or a sulfur atom is preferably represented by formula (a):

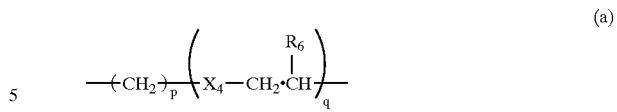

(a)

(wherein $X_4$ is an oxygen atom or a sulfur atom; $R_6$ is a hydrogen atom or a methyl group; and "p" and "q" are each an integer of 1 to 4).

$Y_1$ and $Y_2$ in formula (1) are each preferably an alkylene group having a total carbon number of 1 to 8, more preferably $Y_1$ is the one represented by —$(CH_2)_k$— and $Y_2$ is the one represented by —$(CH_2)_l$—, wherein "k" and "l" are each an integer of 1 to 4, preferably 1 to 3, still more preferably 1 or 2, particularly preferably 1.

$X_1$ and $X_2$ in formula (1) are each a sulfur atom or an oxygen atom, preferably the sulfur atom.

Of the acrylic ester compounds of the present invention represented by formula (1), those represented by formulae (1-a) to (1-d) are particularly preferable embodiments:

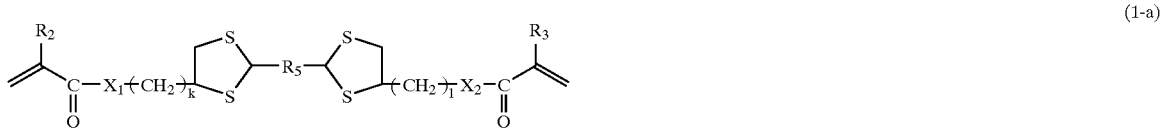

(1-a)

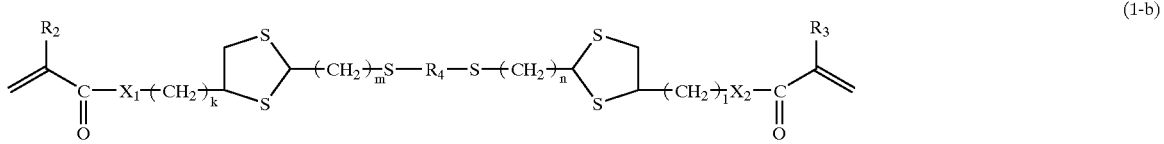

(1-b)

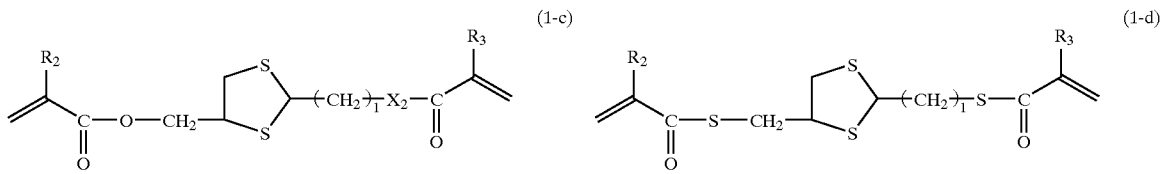

(1-c)                                                                 (1-d)

(wherein $R_5$ is a directly bonded single bond, alkylene group which may have a substituent, aralkylene group which may have a substituent, or arylene group which may have a substituent, similarly to $R_1$; and $R_2$, $R_3$, $R_4$, $X_1$, $X_2$, "k" and "l", "m" and "n" are same meanings as described above).

The specific examples of the acrylic ester compounds of the present invention represented by formula (1), are listed below, although those useful for the present invention are not limited thereto:

| Example Compound Nos | Compound Names |
|---|---|
| 1-a-1 | 2,2'-Bi(4-acryloyloxymethyl-1,3-dithiolan) |
| 1-a-2 | 1,1-Bis(4-acryloyloxymethyl-1,3-dithiolan-2-yl)methane |
| 1-a-3 | 1,2-Bis(4-acryloyloxymethyl-1,3-dithiolan-2-yl)ethane |
| 1-a-4 | 1,3-Bis(4-acryloyloxymethyl-1,3-dithiolan-2-yl)propane |
| 1-a-5 | 1,4-Bis(4-acryloyloxymethyl-1,3-dithiolan-2-yl)butane |
| 1-a-6 | 1,6-Bis(4-acryloyloxymethyl-1,3-dithiolan-2-yl)hexane |

-continued

| Example Compound Nos | Compound Names |
|---|---|
| 1-a-7 | 1,4-Bis[(4-acryloyloxymethyl-1,3-dithiolan-2-yl)methyl]cyclohexane |
| 1-a-8 | 1,4-Bis[(4-acryloyloxymethyl-1,3-dithiolan-2-yl)methyl]benzene |
| 1-a-9 | 1,3-Bis[(4-acryloyloxymethyl-1,3-dithiolan-2-yl)methyl]benzene |
| 1-a-10 | 1,2-Bis[(4-acryloyloxymethyl-1,3-dithiolan-2-yl)methyl]benzene |
| 1-a-11 | 1,4-Bis(4-acryloyloxymethyl-1,3-dithiolan-2-yl)benzene |
| 1-a-12 | 1,3-Bis(4-acryloyloxymethyl-1,3-dithiolan-2-yl)benzene |
| 1-a-13 | 1,2-Bis(4-acryloyloxymethyl-1,3-dithiolan-2-yl)benzene |
| 1-a-14 | 2,2'-Bis(4-acryloyloxymethyl-1,3-dithiolan-2-yl)biphenyl |
| 1-a-15 | 2,2'-Bis(4-acryloyloxymethyl-1,3-dithiolan-2-yl)diphenyl ether |
| 1-a-16 | 2,3-Bis(4-acryloyloxymethyl-1,3-dithiolan-2-yl)naphthalene |
| 1-a-17 | 2,6-Bis(4-acryloyloxymethyl-1,3-dithiolan-2-yl)naphthalene |
| 1-a-18 | 2,5-Bis(4-acryloyloxymethyl-1,3-dithiolan-2-yl)furan |
| 1-a-19 | 2,5-Bis(4-acryloyloxymethyl-1,3-dithiolan-2-yl)thiophene |
| 1-a-20 | 3,4-Bis(4-acryloyloxymethyl-1,3-dithiolan-2-yl)thiophene |
| 1-a-21 | 2,2'-Bi(4-acryloylthiomethyl-1,3-dithiolan) |
| 1-a-22 | 1,1-Bis(4-acryloylthiomethyl-1,3-dithiolan-2-yl)methane |
| 1-a-23 | 1,2-Bis(4-acryloylthiomethyl-1,3-dithiolan-2-yl)ethane |
| 1-a-24 | 1,3-Bis(4-acryloylthiomethyl-1,3-dithiolan-2-yl)propane |
| 1-a-25 | 1,4-Bis(4-acryloylthiomethyl-1,3-dithiolan-2-yl)butane |
| 1-a-26 | 1,6-Bis(4-acryloylthiomethyl-1,3-dithiolan-2-yl)hexane |
| 1-a-27 | 1,4-Bis[(4-acryloylthiomethyl-1,3-dithiolan-2-yl)methyl]cyclohexane |
| 1-a-28 | 1,4-Bis[(4-acryloylthiomethyl-1,3-dithiolan-2-yl)methyl]benzene |
| 1-a-29 | 1,3-Bis[(4-acryloylthiomethyl-1,3-dithiolan-2-yl)methyl]benzene |
| 1-a-30 | 1,2-Bis[(4-acryloylthiomethyl-1,3-dithiolan-2-yl)methyl]benzene |
| 1-a-31 | 1,4-Bis(4-acryloylthiomethyl-1,3-dithiolan-2-yl)benzene |
| 1-a-32 | 1,3-Bis(4-acryloylthiomethyl-1,3-dithiolan-2-yl)benzene |
| 1-a-33 | 1,2-Bis(4-acryloylthiomethyl-1,3-dithiolan-2-yl)benzene |
| 1-a-34 | 2,2'-Bis(4-acryloylthiomethyl-1,3-dithiolan-2-yl)-biphenyl |
| 1-a-35 | 2,2'-Bis(4-acryloylthiomethyl-1,3-dithiolan-2-yl)-diphenyl ether |
| 1-a-36 | 2,3-Bis(4-acryloylthiomethyl-1,3-dithiolan-2-yl)naphthalene |
| 1-a-37 | 2,6-Bis(4-acryloylthiomethyl-1,3-dithiolan-2-yl)naphthalene |
| 1-a-38 | 2,5-Bis(4-acryloylthiomethyl-1,3-dithiolan-2-yl)furan |
| 1-a-39 | 2,5-Bis(4-acryloylthiomethyl-1,3-dithiolan-2-yl)thiophene |
| 1-a-40 | 3,4-Bis(4-acryloylthiomethyl-1,3-dithiolan-2-yl)thiophene |
| 1-a-41 | 2,2'-Bi(4-methacryloyloxymethyl-1,3-dithiolan) |
| 1-a-42 | 1,1-Bis(4-methacryloyloxymethyl-1,3-dithiolan-2-yl)methane |
| 1-a-43 | 1,2-Bis(4-methacryloyloxymethyl-1,3-dithiolan-2-yl)ethane |
| 1-a-44 | 1,3-Bis(4-methacryloyloxymethyl-1,3-dithiolan-2-yl)propane |

-continued

| Example Compound Nos | Compound Names |
|---|---|
| 1-a-45 | 1,4-Bis(4-methacryloyloxymethyl-1,3-dithiolan-2-yl)butane |
| 1-a-46 | 1,6-Bis(4-methacryloyloxymethyl-1,3-dithiolan-2-yl)hexane |
| 1-a-47 | 1,4-Bis[(4-methacryloyloxymethyl-1,3-dithiolan-2-yl)methyl]cyclohexane |
| 1-a-48 | 1,4-Bis[(4-methacryloyloxymethyl-1,3-dithiolan-2-yl)methyl]benzene |
| 1-a-49 | 1,3-Bis[(4-methacryloyloxymethyl-1,3-dithiolan-2-yl)methyl]benzene |
| 1-a-50 | 1,2-Bis[(4-methacryloyloxymethyl-1,3-dithiolan-2-yl)methyl]benzene |
| 1-a-51 | 1,4-Bis(4-methacryloyloxymethyl-1,3-dithiolan-2-yl)benzene |
| 1-a-52 | 1,3-Bis(4-methacryloyloxymethyl-1,3-dithiolan-2-yl)benzene |
| 1-a-53 | 1,2-Bis(4-methacryloyloxymethyl-1,3-dithiolan-2-yl)benzene |
| 1-a-54 | 2,2'-Bis(4-methacryloyloxymethyl-1,3-dithiolan-2-yl)-biphenyl |
| 1-a-55 | 2,2'-Bis(4-methacryloyloxymethyl-1,3-dithiolan-2-yl)-diphenyl ether |
| 1-a-56 | 2,3-Bis(4-methacryloyloxymethyl-1,3-dithiolan-2-yl)naphthalene |
| 1-a-57 | 2,6-Bis(4-methacryloyloxymethyl-1,3-dithiolan-2-yl)naphthalene |
| 1-a-58 | 2,5-Bis(4-methacryloyloxymethyl-1,3-dithiolan-2-yl)furan |
| 1-a-59 | 2,5-Bis(4-methacryloyloxymethyl-1,3-dithiolan-2-yl)thiophene |
| 1-a-60 | 3,4-Bis(4-methacryloyloxymethyl-1,3-dithiolan-2-yl)thiophene |
| 1-a-61 | 2,2'-Bi(4-methacryloylthiomethyl-1,3-dithiolan) |
| 1-a-62 | 1,1-Bis(4-methacryloylthiomethyl-1,3-dithiolan-2-yl)methane |
| 1-a-63 | 1,2-Bis(4-methacryloylthiomethyl-1,3-dithiolan-2-yl)ethane |
| 1-a-64 | 1,3-Bis(4-methacryloylthiomethyl-1,3-dithiolan-2-yl)propane |
| 1-a-65 | 1,4-Bis(4-methacryloylthiomethyl-1,3-dithiolan-2-yl)butane |
| 1-a-66 | 1,6-Bis(4-methacryloylthiomethyl-1,3-dithiolan-2-yl)hexane |
| 1-a-67 | 1,4-Bis[(4-methacryloylthiomethyl-1,3-dithiolan-2-yl)methyl]cyclohexane |
| 1-a-68 | 1,4-Bis[(4-methacryloylthiomethyl-1,3-dithiolan-2-yl)methyl]benzene |
| 1-a-69 | 1,3-Bis[(4-methacryloylthiomethyl-1,3-dithiolan-2-yl)methyl]benzene |
| 1-a-70 | 1,2-Bis[(4-methacryloylthiomethyl-1,3-dithiolan-2-yl)methyl]benzene |
| 1-a-71 | 1,4-Bis(4-methacryloylthiomethyl-1,3-dithiolan-2-yl)benzene |
| 1-a-72 | 1,3-Bis(4-methacryloylthiomethyl-1,3-dithiolan-2-yl)benzene |
| 1-a-73 | 1,2-Bis(4-methacryloylthiomethyl-1,3-dithiolan-2-yl)benzene |
| 1-a-74 | 2,2'-Bis(4-methacryloylthiomethyl-1,3-dithiolan-2-yl)-biphenyl |
| 1-a-75 | 2,2'-Bis(4-methacryloylthiomethyl-1,3-dithiolan-2-yl)-diphenyl ether |
| 1-a-76 | 2,3-Bis(4-methacryloylthiomethyl-1,3-dithiolan-2-yl)naphthalene |
| 1-a-77 | 2,6-Bis(4-methacryloylthiomethyl-1,3-dithiolan-2-yl)naphthalene |
| 1-a-78 | 2,5-Bis(4-methacryloylthiomethyl-1,3-dithiolan-2-yl)furan |
| 1-a-79 | 2,5-Bis(4-methacryloylthiomethyl-1,3-dithiolan-2-yl)thiophene |
| 1-a-80 | 3,4-Bis(4-methacryloylthiomethyl-1,3-dithiolan-2-yl)thiophene |
| 1-a-81 | 2,2'-Bi[4-(2-acryloyloxyethyl)-1,3-dithiolan] |
| 1-a-82 | 1,3-Bis[4-(2-acryloyloxyethyl)-1,4-dithiolan-2-yl]benzene |
| 1-a-83 | 2,2'-Bi[4-(2-acryloylthioethyl)-1,3-dithiolan] |

-continued

| Example Compound Nos | Compound Names |
|---|---|
| 1-a-84 | 1,1-Bis[4-(3-acryloylthiopropyl)-1,3-dithiolan-2-yl]methane |
| 1-a-85 | 1,3-Bis[4-(2-acryloylthiobutyl)-1,3-dithiolan-2-yl]benzene |
| 1-a-86 | 2,2'-Bi[4-(2-methacryloyloxyethyl)-1,3-dithiolan] |
| 1-a-87 | 2,2'-Bi[4-(2-methacryloylthioethyl)-1,3-dithiolan] |
| 1-a-88 | 1,3-Bis[4-(2-methacryloyloxyethyl)-1,4-dithiolan-2-yl]benzene |
| 1-a-89 | 4-Acryloyloxy-4'-acryloylthio-2,2'-bi(1,3-dithiolan) |
| 1-a-90 | 1-(4-Acryloylthiomethyl-1,3-dithiolan-2-yl)-1-(4-acryloyloxymethyl-1,3-dithiolan-2-yl)methane |
| 1-a-91 | 1-(4-Acryloylthiomethyl-1,3-dithiolan-2-yl)-2-(4-methacryloylthiomethyl-1,3-dithiolan-2-yl)ethane |
| 1-a-92 | 1-(4-Acryloylthiomethyl-1,3-dithiolan-2-yl)-4-(4-methacryloyloxythiomethyl-1,3-dithiolan-2-yl)benzene |
| 1-a-93 | 1-(4-Methacryloylthiomethyl-1,3-dithiolan-2-yl)-4-(4-acryloyloxythiomethyl-1,3-dithiolan-2-yl)benzene |
| 1-b-1 | Bis[(4-acryloyloxymethyl-1,3-dithiolan-2-yl)methylthio]methane |
| 1-b-2 | 1,1-Bis[(4-acryloyloxymethyl-1,3-dithiolan-2-yl)methylthio]ethane |
| 1-b-3 | 1,2-Bis[(4-acryloyloxymethyl-1,3-dithiolan-2-yl)methylthio]ethane |
| 1-b-4 | 1,3-Bis[(4-acryloyloxymethyl-1,3-dithiolan-2-yl)methylthio]propane |
| 1-b-5 | 1,2-Bis[(4-acryloyloxymethyl-1,3-dithiolan-2-yl)methylthio]propane |
| 1-b-6 | 2,2-Bis[(4-acryloyloxymethyl-1,3-dithiolan-2-yl)methylthio]propane |
| 1-b-7 | 1,4-Bis[(4-acryloyloxymethyl-1,3-dithiolan-2-yl)methylthio]butane |
| 1-b-8 | 1,5-Bis[(4-acryloyloxymethyl-1,3-dithiolan-2-yl)methylthio]pentane |
| 1-b-9 | 1,6-Bis[(4-acryloyloxymethyl-1,3-dithiolan-2-yl)methylthio]hexane |
| 1-b-10 | 1,8-Bis[(4-acryloyloxymethyl-1,3-dithiolan-2-yl)methylthio]octane |
| 1-b-11 | 1,4-Bis[(4-acryloyloxymethyl-1,3-dithiolan-2-yl)methylthio]cyclohexane |
| 1-b-12 | 1,3-Bis[(4-acryloyloxymethyl-1,3-dithiolan-2-yl)methylthio]cyclohexane |
| 1-b-13 | 1,2-Bis[(4-acryloyloxymethyl-1,3-dithiolan-2-yl)methylthio]cyclohexane |
| 1-b-14 | 1,4-Bis[(4-acryloyloxymethyl-1,3-dithiolan-2-yl)methylthiomethyl]cyclohexane |
| 1-b-15 | 1,3-Bis[(4-acryloyloxymethyl-1,3-dithiolan-2-yl)methylthiomethyl]cyclohexane |
| 1-b-16 | 1,2-Bis[(4-acryloyloxymethyl-1,3-dithiolan-2-yl)methylthiomethyl]cyclohexane |
| 1-b-17 | 1,4-Bis[(4-acryloyloxymethyl-1,3-dithiolan-2-yl)methylthiomethyl]benzene |
| 1-b-18 | 1,3-Bis[(4-acryloyloxymethyl-1,3-dithiolan-2-yl)methylthiomethyl]benzene |
| 1-b-19 | 1,2-Bis[(4-acryloyloxymethyl-1,3-dithiolan-2-yl)methylthiomethyl]benzene |
| 1-b-20 | 1,4-Bis[1'-(4-acryloyloxymethyl-1,3-dithiolan-2-yl)methylthioethyl]benzene |
| 1-b-21 | 1,3-Bis[1'-(4-acryloyloxymethyl-1,3-dithiolan-2-yl)methylthioethyl]benzene |
| 1-b-22 | 1,2-Bis[1'-(4-acryloyloxymethyl-1,3-dithiolan-2-yl)methylthioethyl]benzene |
| 1-b-23 | 1,4-Bis[2'-(4-acryloyloxymethyl-1,3-dithiolan-2-yl)methylthioethyl]benzene |
| 1-b-24 | 1,3-Bis[2'-(4-acryloyloxymethyl-1,3-dithiolan-2-yl)methylthioethyl]benzene |
| 1-b-25 | 1,2-Bis[2'-(4-acryloyloxymethyl-1,3-dithiolan-2-yl)methylthioethyl]benzene |
| 1-b-26 | 1,4-Bis[2'-(4-acryloyloxymethyl-1,3-dithiolan-2-yl)methylthio]benzene |
| 1-b-27 | 1,3-Bis[2'-(4-acryloyloxymethyl-1,3-dithiolan-2-yl)methylthio]benzene |
| 1-b-28 | 1,2-Bis[2'-(4-acryloyloxymethyl-1,3-dithiolan-2-yl)methylthio]benzene |
| 1-b-29 | 1,4-Bis[2'-(4-acryloyloxymethyl-1,3-dithiolan-2-yl)methylthio]naphthalene |
| 1-b-30 | 1,5-Bis[2'-(4-acryloyloxymethyl-1,3-dithiolan-2-yl)methylthio]naphthalene |
| 1-b-31 | 2,6-Bis[2'-(4-acryloyloxymethyl-1,3-dithiolan-2-yl)methylthio]naphthalene |
| 1-b-32 | 1,5-Bis[2'-(4-acryloyloxymethyl-1,3-dithiolan-2-yl)methylthio]naphthalene |
| 1-b-33 | 2,7-Bis[2'-(4-acryloyloxymethyl-1,3-dithiolan-2-yl)methylthio]naphthalene |
| 1-b-34 | 2,5-Bis[2'-(4-acryloyloxymethyl-1,3-dithiolan-2-yl)methylthio]thiophene |
| 1-b-35 | 3,4-Bis[2'-(4-acryloyloxymethyl-1,3-dithiolan-2-yl)methylthio]thiophene |
| 1-b-36 | Bis[(4-methacryloyloxymethyl-1,3-dithiolan-2-yl)methylthio]methane |
| 1-b-37 | 1,1-Bis[(4-methacryloyloxymethyl-1,3-dithiolan-2-yl)methylthio]ethane |
| 1-b-38 | 1,2-Bis[(4-methacryloyloxymethyl-1,3-dithiolan-2-yl)methylthio]ethane |
| 1-b-39 | 1,3-Bis[(4-methacryloyloxymethyl-1,3-dithiolan-2-yl)methylthio]propane |
| 1-b-40 | 1,2-Bis[(4-methacryloyloxymethyl-1,3-dithiolan-2-yl)methylthio]propane |
| 1-b-41 | 2,2-Bis[(4-methacryloyloxymethyl-1,3-dithiolan-2-yl)methylthio]propane |
| 1-b-42 | 1,4-Bis[(4-methacryloyloxymethyl-1,3-dithiolan-2-yl)methylthio]butane |
| 1-b-43 | 1,5-Bis[(4-methacryloyloxymethyl-1,3-dithiolan-2-yl)methylthio]pentane |
| 1-b-44 | 1,6-Bis[(4-methacryloyloxymethyl-1,3-dithiolan-2-yl)methylthio]hexane |
| 1-b-45 | 1,8-Bis[(4-methacryloyloxymethyl-1,3-dithiolan-2-yl)methylthio]octane |
| 1-b-46 | 1,4-Bis[(4-methacryloyloxymethyl-1,3-dithiolan-2-yl)methylthio]cyclohexane |
| 1-b-47 | 1,3-Bis[(4-methacryloyloxymethyl-1,3-dithiolan-2-yl)methylthio]cyclohexane |
| 1-b-48 | 1,2-Bis[(4-methacryloyloxymethyl-1,3-dithiolan-2-yl)methylthio]cyclohexane |
| 1-b-49 | 1,4-Bis[(4-methacryloyloxymethyl-1,3-dithiolan-2-yl)methylthiomethyl]cyclohexane |
| 1-b-50 | 1,3-Bis[(4-methacryloyloxymethyl-1,3-dithiolan-2-yl)methylthiomethyl]cyclohexane |
| 1-b-51 | 1,2-Bis[(4-methacryloyloxymethyl-1,3-dithiolan-2-yl)methylthiomethyl]cyclohexane |
| 1-b-52 | 1,4-Bis[(4-methacryloyloxymethyl-1,3-dithiolan-2-yl)methylthiomethyl]benzene |
| 1-b-53 | 1,3-Bis[(4-methacryloyloxymethyl-1,3-dithiolan-2-yl)methylthiomethyl]benzene |
| 1-b-54 | 1,2-Bis[(4-methacryloyloxymethyl-1,3-dithiolan-2-yl)methylthiomethyl]benzene |
| 1-b-55 | 1,4-Bis[1'-(4-methacryloyloxymethyl-1,3-dithiolan-2-yl)methylthioethyl]benzene |
| 1-b-56 | 1,3-Bis[1'-(4-methacryloyloxymethyl-1,3-dithiolan-2-yl)methylthioethyl]benzene |
| 1-b-57 | 1,2-Bis[1'-(4-methacryloyloxymethyl-1,3-dithiolan-2-yl)methylthioethyl]benzene |
| 1-b-58 | 1,4-Bis[2'-(4-methacryloyloxymethyl-1,3-dithiolan-2-yl)methylthioethyl]benzene |
| 1-b-59 | 1,3-Bis[2'-(4-methacryloyloxymethyl-1,3-dithiolan-2-yl)methylthioethyl]benzene |
| 1-b-60 | 1,2-Bis[2'-(4-methacryloyloxymethyl-1,3-dithiolan-2-yl)methylthioethyl]benzene |
| 1-b-61 | 1,4-Bis[2'-(4-methacryloyloxymethyl-1,3-dithiolan-2-yl)methylthio]benzene |
| 1-b-62 | 1,3-Bis[2'-(4-methacryloyloxymethyl-1,3-dithiolan-2-yl)methylthio]benzene |
| 1-b-63 | 1,2-Bis[2'-(4-methacryloyloxymethyl-1,3-dithiolan-2-yl)methylthio]benzene |

| Example Compound Nos | Compound Names |
|---|---|
| 1-b-64 | 1,4-Bis[2'-(4-methacryloyloxymethyl-1,3-dithiolan-2-yl)methylthio]naphthalene |
| 1-b-65 | 1,5-Bis[2'-(4-methacryloyloxymethyl-1,3-dithiolan-2-yl)methylthio]naphthalene |
| 1-b-66 | 2,6-Bis[2'-(4-methacryloyloxymethyl-1,3-dithiolan-2-yl)methylthio]naphthalene |
| 1-b-67 | 1,5-Bis[2'-(4-methacryloyloxymethyl-1,3-dithiolan-2-yl)methylthio]naphthalene |
| 1-b-68 | 2,7-Bis[2'-(4-methacryloyloxymethyl-1,3-dithiolan-2-yl)methylthio]naphthalene |
| 1-b-69 | 2,5-Bis[2'-(4-methacryloyloxymethyl-1,3-dithiolan-2-yl)methylthio]thiophene |
| 1-b-70 | 3,4-Bis[2'-(4-methacryloyloxymethyl-1,3-dithiolan-2-yl)methylthio]thiophene |
| 1-b-71 | Bis[(4-acryloylthiomethyl-1,3-dithiolan-2-yl)methylthio]methane |
| 1-b-72 | 1,1-Bis[(4-acryloylthiomethyl-1,3-dithiolan-2-yl)methylthio]ethane |
| 1-b-73 | 1,2-Bis[(4-acryloylthiomethyl-1,3-dithiolan-2-yl)methylthio]ethane |
| 1-b-74 | 1,3-Bis[(4-acryloylthiomethyl-1,3-dithiolan-2-yl)methylthio]propane |
| 1-b-75 | 1,2-Bis[(4-acryloylthiomethyl-1,3-dithiolan-2-yl)methylthio]propane |
| 1-b-76 | 2,2-Bis[(4-acryloylthiomethyl-1,3-dithiolan-2-yl)methylthio]propane |
| 1-b-77 | 1,4-Bis[(4-acryloylthiomethyl-1,3-dithiolan-2-yl)methylthio]butane |
| 1-b-78 | 1,5-Bis[(4-acryloylthiomethyl-1,3-dithiolan-2-yl)methylthio]pentane |
| 1-b-79 | 1,6-Bis[(4-acryloylthiomethyl-1,3-dithiolan-2-yl)methylthio]hexane |
| 1-b-80 | 1,8-Bis[(4-acryloylthiomethyl-1,3-dithiolan-2-yl)methylthio]octane |
| 1-b-81 | 1,4-Bis[(4-acryloylthiomethyl-1,3-dithiolan-2-yl)methylthio]cyclohexane |
| 1-b-82 | 1,3-Bis[(4-acryloylthiomethyl-1,3-dithiolan-2-yl)methylthio]cyclohexane |
| 1-b-83 | 1,2-Bis[(4-acryloylthiomethyl-1,3-dithiolan-2-yl)methylthio]cyclohexane |
| 1-b-84 | 1,4-Bis[(4-acryloylthiomethyl-1,3-dithiolan-2-yl)methylthiomethyl]cyclohexane |
| 1-b-85 | 1,3-Bis[(4-acryloylthiomethyl-1,3-dithiolan-2-yl)methylthiomethyl]cyclohexane |
| 1-b-86 | 1,2-Bis[(4-acryloylthiomethyl-1,3-dithiolan-2-yl)methylthiomethyl]cyclohexane |
| 1-b-87 | 1,4-Bis[(4-acryloylthiomethyl-1,3-dithiolan-2-yl)methylthiomethyl]benzene |
| 1-b-88 | 1,3-Bis[(4-acryloylthiomethyl-1,3-dithiolan-2-yl)methylthiomethyl]benzene |
| 1-b-89 | 1,2-Bis[(4-acryloylthiomethyl-1,3-dithiolan-2-yl)methylthiomethyl]benzene |
| 1-b-90 | 1,4-Bis[1'-(4-acryloylthiomethyl-1,3-dithiolan-2-yl)methylthioethyl]benzene |
| 1-b-91 | 1,3-Bis[1'-(4-acryloylthiomethyl-1,3-dithiolan-2-yl)methylthioethyl]benzene |
| 1-b-92 | 1,2-Bis[1'-(4-acryloylthiomethyl-1,3-dithiolan-2-yl)methylthioethyl]benzene |
| 1-b-93 | 1,4-Bis[2'-(4-acryloylthiomethyl-1,3-dithiolan-2-yl)methylthioethyl]benzene |
| 1-b-94 | 1,3-Bis[2'-(4-acryloylthiomethyl-1,3-dithiolan-2-yl)methylthioethyl]benzene |
| 1-b-95 | 1,2-Bis[2'-(4-acryloylthiomethyl-1,3-dithiolan-2-yl)methylthioethyl]benzene |
| 1-b-96 | 1,4-Bis[2'-(4-acryloylthiomethyl-1,3-dithiolan-2-yl)methylthio]benzene |
| 1-b-97 | 1,3-Bis[2'-(4-acryloylthiomethyl-1,3-dithiolan-2-yl)methylthio]benzene |
| 1-b-98 | 1,2-Bis[2'-(4-acryloylthiomethyl-1,3-dithiolan-2-yl)methylthio]benzene |
| 1-b-99 | 1,4-Bis[2'-(4-acryloylthiomethyl-1,3-dithiolan-2-yl)methylthio]naphthalene |
| 1-b-100 | 1,5-Bis[2'-(4-acryloylthiomethyl-1,3-dithiolan-2-yl)methylthio]naphthalene |
| 1-b-101 | 2,6-Bis[2'-(4-acryloylthiomethyl-1,3-dithiolan-2-yl)methylthio]naphthalene |
| 1-b-102 | 1,5-Bis[2'-(4-acryloylthiomethyl-1,3-dithiolan-2-yl)methylthio]naphthalene |
| 1-b-103 | 2,7-Bis[2'-(4-acryloylthiomethyl-1,3-dithiolan-2-yl)methylthio]naphthalene |
| 1-b-104 | 2,5-Bis[2'-(4-acryloylthiomethyl-1,3-dithiolan-2-yl)methylthio]thiophene |
| 1-b-105 | 3,4-Bis[2'-(4-acryloylthiomethyl-1,3-dithiolan-2-yl)methylthio]thiophene |
| 1-b-106 | Bis[(4-methacryloylthiomethyl-1,3-dithiolan-2-yl)methylthio]methane |
| 1-b-107 | 1,1-Bis[(4-methacryloylthiomethyl-1,3-dithiolan-2-yl)methylthio]ethane |
| 1-b-108 | 1,2-Bis[(4-methacryloylthiomethyl-1,3-dithiolan-2-yl)methylthio]ethane |
| 1-b-109 | 1,3-Bis[(4-methacryloylthiomethyl-1,3-dithiolan-2-yl)methylthio]propane |
| 1-b-110 | 1,2-Bis[(4-methacryloylthiomethyl-1,3-dithiolan-2-yl)methylthio]propane |
| 1-b-111 | 2,2-Bis[(4-methacryloylthiomethyl-1,3-dithiolan-2-yl)methylthio]propane |
| 1-b-112 | 1,4-Bis[(4-methacryloylthiomethyl-1,3-dithiolan-2-yl)methylthio]butane |
| 1-b-113 | 1,5-Bis[(4-methacryloylthiomethyl-1,3-dithiolan-2-yl)methylthio]pentane |
| 1-b-114 | 1,6-Bis[(4-methacryloylthiomethyl-1,3-dithiolan-2-yl)methylthio]hexane |
| 1-b-115 | 1,8-Bis[(4-methacryloylthiomethyl-1,3-dithiolan-2-yl)methylthio]octane |
| 1-b-116 | 1,4-Bis[(4-methacryloylthiomethyl-1,3-dithiolan-2-yl)methylthio]cyclohexane |
| 1-b-117 | 1,3-Bis[(4-methacryloylthiomethyl-1,3-dithiolan-2-yl)methylthio]cyclohexane |
| 1-b-118 | 1,2-Bis[(4-methacryloylthiomethyl-1,3-dithiolan-2-yl)methylthio]cyclohexane |
| 1-b-119 | 1,4-Bis[(4-methacryloylthiomethyl-1,3-dithiolan-2-yl)methylthiomethyl]cyclohexane |
| 1-b-120 | 1,3-Bis[(4-methacryloylthiomethyl-1,3-dithiolan-2-yl)methylthiomethyl]cyclohexane |
| 1-b-121 | 1,2-Bis[(4-methacryloylthiomethyl-1,3-dithiolan-2-yl)methylthiomethyl]cyclohexane |
| 1-b-122 | 1,4-Bis[(4-methacryloylthiomethyl-1,3-dithiolan-2-yl)methylthiomethyl]benzene |
| 1-b-123 | 1,3-Bis[(4-methacryloylthiomethyl-1,3-dithiolan-2-yl)methylthiomethyl]benzene |
| 1-b-124 | 1,2-Bis[(4-methacryloylthiomethyl-1,3-dithiolan-2-yl)methylthiomethyl]benzene |
| 1-b-125 | 1,4-Bis[1'-(4-methacryloylthiomethyl-1,3-dithioethyl]benzene |
| 1-b-126 | 1,3-Bis[1'-(4-methacryloylthiomethyl-1,3-dithioethyl]benzene |
| 1-b-127 | 1,2-Bis[1'-(4-methacryloylthiomethyl-1,3-dithioethyl]benzene |
| 1-b-128 | 1,4-Bis[2'-(4-methacryloylthiomethyl-1,3-dithioethyl]benzene |
| 1-b-129 | 1,3-Bis[2'-(4-methacryloylthiomethyl-1,3-dithioethyl]benzene |
| 1-b-130 | 1,2-Bis[2'-(4-methacryloylthiomethyl-1,3-dithioethyl]benzene |
| 1-b-131 | 1,4-Bis[2'-(4-methacryloylthiomethyl-1,3-dithiolan-2-yl)methylthio]benzene |
| 1-b-132 | 1,3-Bis[2'-(4-methacryloylthiomethyl-1,3-dithiolan-2-yl)methylthio]benzene |
| 1-b-133 | 1,2-Bis[2'-(4-methacryloylthiomethyl-1,3-dithiolan-2-yl)methylthio]benzene |
| 1-b-134 | 1,4-Bis[2'-(4-methacryloylthiomethyl-1,3-dithiolan-2-yl)methylthio]naphthalene |
| 1-b-135 | 1,5-Bis[2'-(4-methacryloylthiomethyl-1,3-dithiolan-2-yl)methylthio]naphthalene |
| 1-b-136 | 2,6-Bis[2'-(4-methacryloylthiomethyl-1,3-dithiolan-2-yl)methylthio]naphthalene |
| 1-b-137 | 1,5-Bis[2'-(4-methacryloylthiomethyl-1,3-dithiolan-2-yl)methylthio]naphthalene |

| Example Compound Nos | Compound Names |
|---|---|
| 1-b-138 | 2,7-Bis[2'-(4-methacryloylthiomethyl-1,3-dithiolan-2-yl)methylthio]naphthalene |
| 1-b-139 | 2,5-Bis[2'-(4-methacryloylthiomethyl-1,3-dithiolan-2-yl)methylthio]thiophene |
| 1-b-140 | 3,4-Bis[2'-(4-methacryloylthiomethyl-1,3-dithiolan-2-yl)methylthio]thiophene |
| 1-b-141 | Bis[(4-acryloyloxyethyl-1,3-dithiolan-2-yl)methylthio]methane |
| 1-b-142 | 1,2-Bis[(4-acryloyloxypropyl-1,3-dithiolan-2-yl)methylthio]ethane |
| 1-b-143 | 1,4-Bis[(4-acryloyloxybutyl-1,3-dithiolan-2-yl)methylthiomethyl]cyclohexane |
| 1-b-144 | 1,4-Bis[(4-acryloyloxyethyl-1,3-dithiolan-2-yl)methylthiomethyl]benzene |
| 1-b-145 | 1,4-Bis[2'-(4-acryloyloxyethyl-1,3-dithiolan-2-yl)methylthio]benzene |
| 1-b-146 | 2,5-Bis[2'-(4-acryloyloxyethyl-1,3-dithiolan-2-yl)methylthio]thiophene |
| 1-b-147 | Bis[(4-methacryloyloxyethyl-1,3-dithiolan-2-yl)methylthio]methane |
| 1-b-148 | 1,2-Bis[(4-methacryloyloxypropyl-1,3-dithiolan-2-yl)methylthio]ethane |
| 1-b-149 | 1,4-Bis[(4-methacryloyloxybutyl-1,3-dithiolan-2-yl)methylthiomethyl]cyclohexane |
| 1-b-150 | 1,4-Bis[(4-methacryloyloxyethyl-1,3-dithiolan-2-yl)methylthiomethyl]benzene |
| 1-b-151 | 1,4-Bis[2'-(4-methacryloyloxyethyl-1,3-dithiolan-2-yl)methylthio]benzene |
| 1-b-152 | 2,5-Bis[2'-(4-methacryloyloxyethyl-1,3-dithiolan-2-yl)methylthio]thiophene |
| 1-b-153 | Bis[(4-acryloyloxymethyl-1,3-dithiolan-2-yl)ethylthio]methane |
| 1-b-154 | 1,2-Bis[(4-acryloyloxymethyl-1,3-dithiolan-2-yl)propylthio]ethane |
| 1-b-155 | 1,4-Bis[(4-acryloyloxymethyl-1,3-dithiolan-2-yl)butylthiomethyl]cyclohexane |
| 1-b-156 | 1,4-Bis[(4-acryloyloxymethyl-1,3-dithiolan-2-yl)ethylthiomethyl]benzene |
| 1-b-157 | 1,4-Bis[2'-(4-acryloyloxymethyl-1,3-dithiolan-2-yl)butylthio]benzene |
| 1-b-158 | 2,5-Bis[2'-(4-acryloyloxymethyl-1,3-dithiolan-2-yl)ethylthio]thiophene |
| 1-b-159 | Bis[(4-methacryloyloxymethyl-1,3-dithiolan-2-yl)ethylthio]methane |
| 1-b-160 | 1,2-Bis[(4-methacryloyloxymethyl-1,3-dithiolan-2-yl)propylthio]ethane |
| 1-b-161 | 1,4-Bis[(4-methacryloyloxymethyl-1,3-dithiolan-2-yl)butylthiomethyl]cyclohexane |
| 1-b-162 | 1,4-Bis[(4-methacryloyloxymethyl-1,3-dithiolan-2-yl)ethylthiomethyl]benzene |
| 1-b-163 | 1,4-Bis[2'-(4-methacryloyloxymethyl-1,3-dithiolan-2-yl)butylthio]benzene |
| 1-b-164 | 2,5-Bis[2'-(4-methacryloyloxymethyl-1,3-dithiolan-2-yl)ethylthio]thiophene |
| 1-b-165 | Bis[(4-acryloylthioethyl-1,3-dithiolan-2-yl)methylthio]methane |
| 1-b-166 | 1,2-Bis[(4-acryloylthiopropyl-1,3-dithiolan-2-yl)methylthio]ethane |
| 1-b-167 | 1,4-Bis[(4-acryloylthiobutyl-1,3-dithiolan-2-yl)methylthiomethyl]cyclohexane |
| 1-b-168 | 1,4-Bis[(4-acryloylthioethyl-1,3-dithiolan-2-yl)methylthiomethyl]benzene |
| 1-b-169 | 1,4-Bis[2'-(4-acryloylthioethyl-1,3-dithiolan-2-yl)methylthio]benzene |
| 1-b-170 | 2,5-Bis[2'-(4-acryloylthioethyl-1,3-dithiolan-2-yl)methylthio]thiophene |
| 1-b-171 | Bis[(4-methacryloylthioethyl-1,3-dithiolan-2-yl)methylthio]methane |
| 1-b-172 | 1,2-Bis[(4-methacryloylthiopropyl-1,3-dithiolan-2-yl)methylthio]ethane |
| 1-b-173 | 1,4-Bis[(4-methacryloylthiobutyl-1,3-dithiolan-2-yl)methylthiomethyl]cyclohexane |
| 1-b-174 | 1,4-Bis[(4-methacryloylthioethyl-1,3-dithiolan-2-yl)methylthiomethyl]benzene |
| 1-b-175 | 1,4-Bis[2'-(4-methacryloylthioethyl-1,3-dithiolan-2-yl)methylthio]benzene |
| 1-b-176 | 2,5-Bis[2'-(4-methacryloylthioethyl-1,3-dithiolan-2-yl)methylthio]thiophene |
| 1-b-177 | Bis[(4-acryloylthiomethyl-1,3-dithiolan-2-yl)ethylthio]methane |
| 1-b-178 | 1,2-Bis[(4-acryloylthiomethyl-1,3-dithiolan-2-yl)propylthio]ethane |
| 1-b-179 | 1,4-Bis[(4-acryloylthiomethyl-1,3-dithiolan-2-yl)butylthiomethyl]cyclohexane |
| 1-b-180 | 1,4-Bis[(4-acryloylthiomethyl-1,3-dithiolan-2-yl)ethylthiomethyl]benzene |
| 1-b-181 | 1,4-Bis[2'-(4-acryloylthiomethyl-1,3-dithiolan-2-yl)butylthio]benzene |
| 1-b-182 | 2,5-Bis[2'-(4-acryloylthiomethyl-1,3-dithiolan-2-yl)ethylthio]thiophene |
| 1-b-183 | Bis[(4-methacryloylthiomethyl-1,3-dithiolan-2-yl)ethylthio]methane |
| 1-b-184 | 1,2-Bis[(4-methacryloylthiomethyl-1,3-dithiolan-2-yl)propylthio]ethane |
| 1-b-185 | 1,4-Bis[(4-methacryloylthiomethyl-1,3-dithiolan-2-yl)butylthiomethyl]cyclohexane |
| 1-b-186 | 1,4-Bis[(4-methacryloylthiomethyl-1,3-dithiolan-2-yl)ethylthiomethyl]benzene |
| 1-b-187 | 1,4-Bis[2'-(4-methacryloylthiomethyl-1,3-dithiolan-2-yl)butylthio]benzene |
| 1-b-188 | 2,5-Bis[2'-(4-methacryloylthiomethyl-1,3-dithiolan-2-yl)ethylthio]thiophene |
| 1-b-189 | 1-[(4-Acryloylthiomethyl-1,3-dithiolan-2-yl)ethylthio]-1-[(4-methacryloylthiomethyl-1,3-dithiolan-2-yl)ethylthio]methane |
| 1-b-190 | 1-[(4-Acryloyloxymethyl-1,3-dithiolan-2-yl)methylthio]-1-[(4-acryloylthiomethyl-1,3-dithiolan-2-yl)methylthio]ethane |
| 1-b-191 | 1-[(4-Methacryloylthiomethyl-1,3-dithiolan-2-yl)methylthiomethyl]-4-[(4-methacryloylthio-ethyl-1,3-dithiolan-2-yl)methylthiomethyl]-cyclohexane |
| 1-b-192 | 1-[(4-Acryloylthiomethyl-1,3-dithiolan-2-yl)methylthiomethyl]-4-[(4-acryloylthiomethyl-1,3-dithiolan-2-yl)ethylthiomethyl]benzene |
| 1-b-193 | 1-[2'-(4-Methacryloylthiomethyl-1,3-dithiolan-2-yl)methylthio]-4-[2'-(4-methacryloylthio-methyl-1,3-dithiolan-2-yl)butylthio]benzene |
| 1-b-194 | 2-[2'-(4-Acryloylthiomethyl-1,3-dithiolan-2-yl)methylthio]-5-[2'-(4-methacryloylthiomethyl-1,3-dithiolan-2-yl)methylthio]thiophene |

Moreover, the specific examples of the acrylic ester compounds represented by formulae (1-c) and (1-d) are listed below:

| Example Compound Nos. | Structural Formulae |
|---|---|
| 1-c-1 | 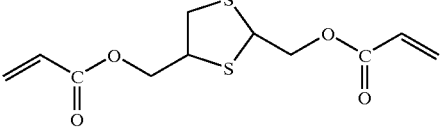 |

-continued
| Example Compound Nos. | Structural Formulae |
|---|---|
| 1-c-2 | 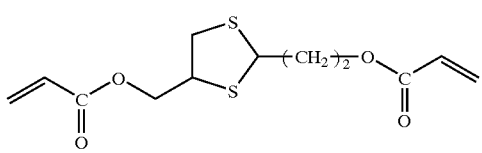 |
| 1-c-3 | 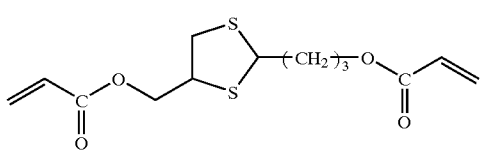 |
| 1-c-4 | 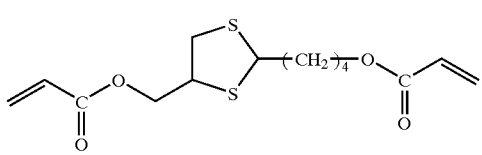 |
| 1-c-5 | 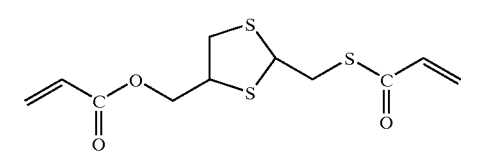 |
| 1-c-6 | 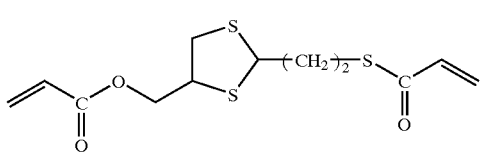 |
| 1-c-7 | 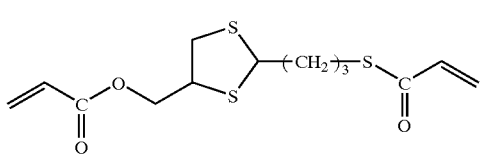 |
| 1-c-8 | 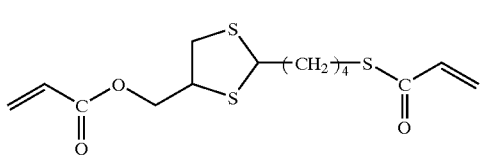 |
| 1-c-9 | 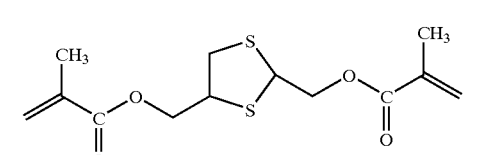 |
| 1-c-10 | 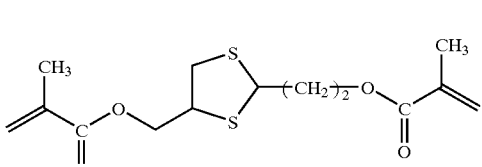 |
-continued
| Example Compound Nos. | Structural Formulae |
|---|---|
| 1-c-11 | 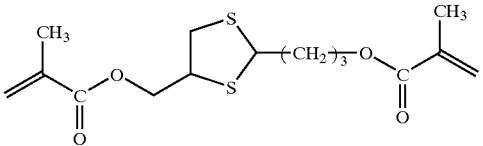 |
| 1-c-12 | 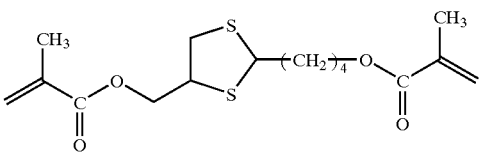 |
| 1-c-13 | 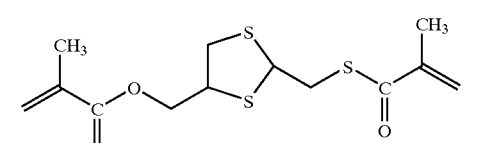 |
| 1-c-14 | 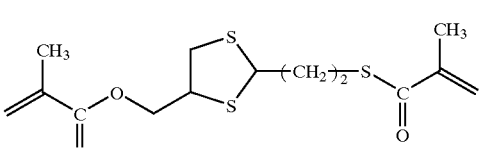 |
| 1-c-15 | 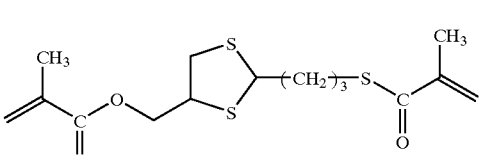 |
| 1-c-16 | 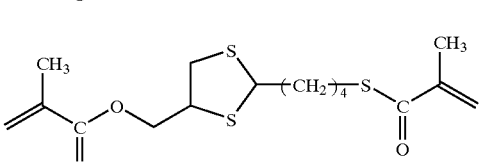 |
| 1-c-17 | 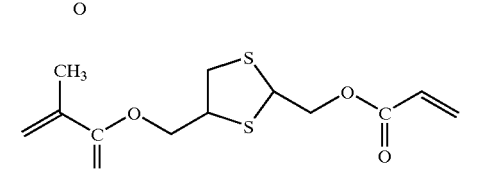 |
| 1-c-18 | 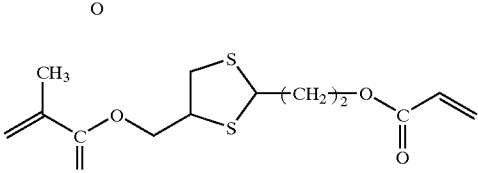 |
| 1-c-19 | 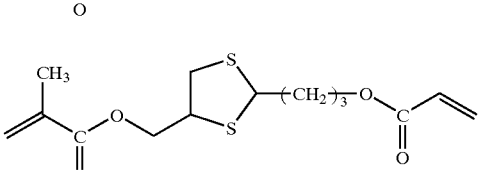 |

| Example Compound Nos. | Structural Formulae |
|---|---|
| 1-c-20 | 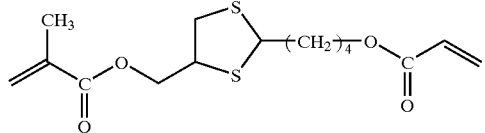 |
| 1-c-21 | 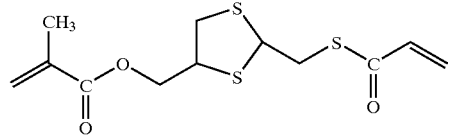 |
| 1-c-22 | 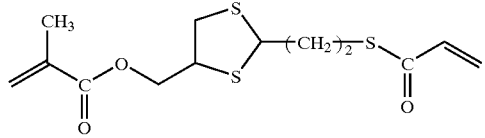 |
| 1-c-23 | 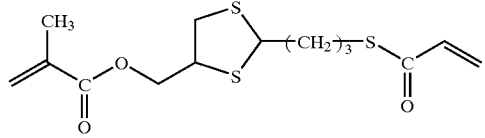 |
| 1-c-24 | 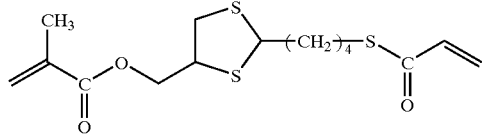 |
| 1-c-25 | 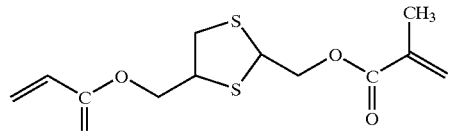 |
| 1-c-26 | 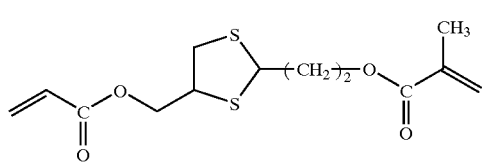 |
| 1-c-27 | 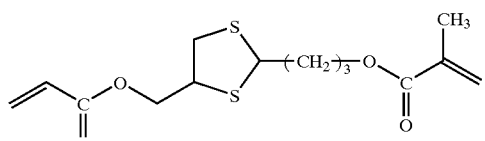 |
| 1-c-28 | 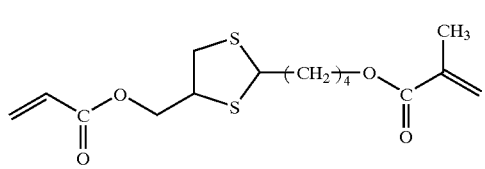 |
| Example Compound Nos. | Structural Formulae |
|---|---|
| 1-c-29 | 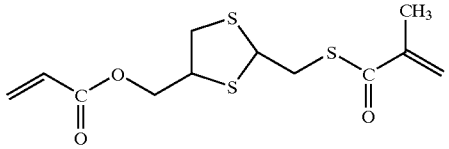 |
| 1-c-30 | 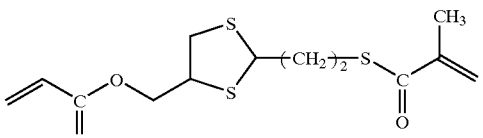 |
| 1-c-31 | 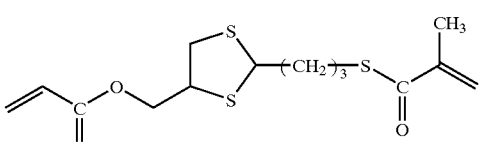 |
| 1-c-32 | 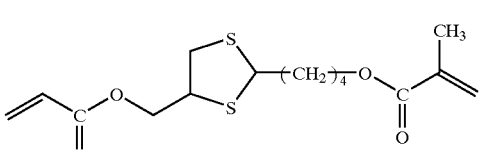 |
| 1-d-1 | 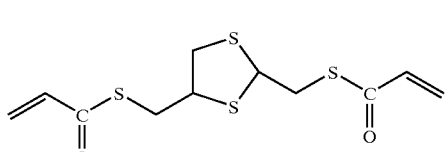 |
| 1-d-2 | 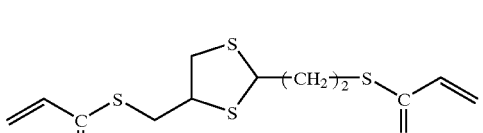 |
| 1-d-3 | 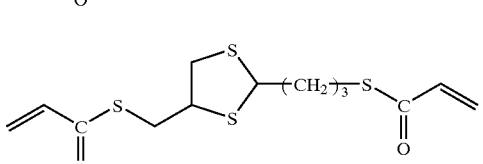 |
| 1-d-4 | 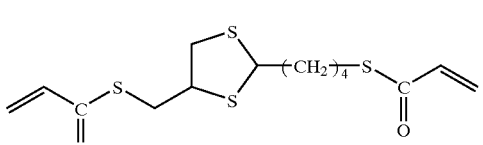 |
| 1-d-5 | 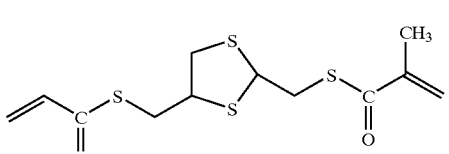 |

| Example Compound Nos. | Structural Formulae |
|---|---|
| 1-d-6 | 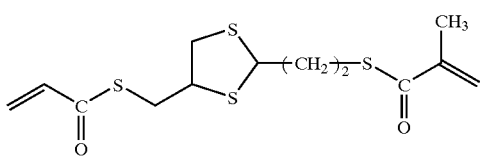 |
| 1-d-7 | 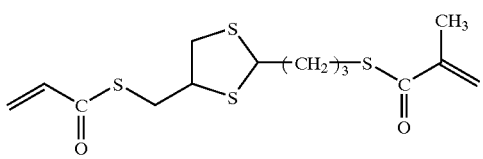 |
| 1-d-8 | 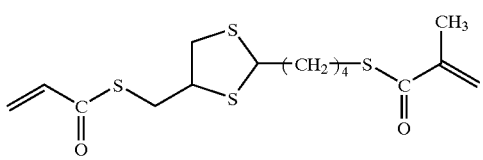 |
| 1-d-9 | 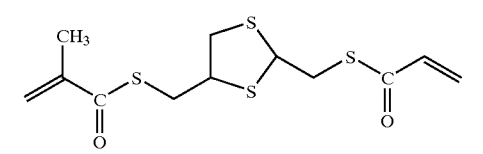 |
| 1-d-10 | 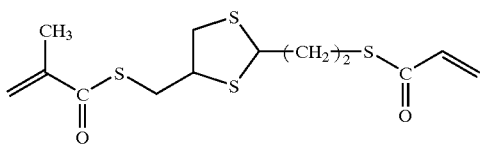 |
| 1-d-11 | 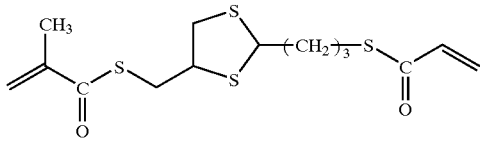 |
| 1-d-12 | 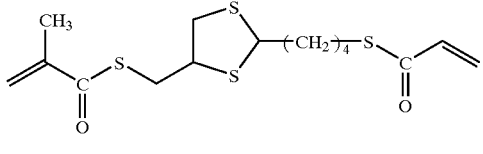 |
| 1-d-13 | 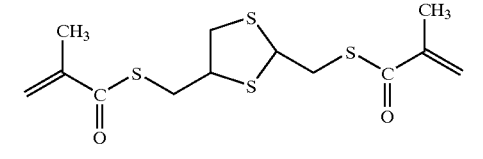 |
| 1-d-14 | 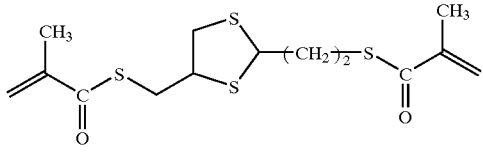 |
| 1-d-15 | 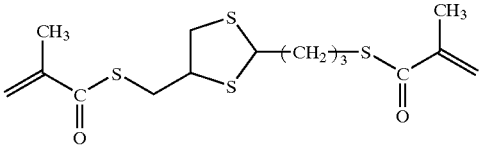 |
| 1-d-16 | 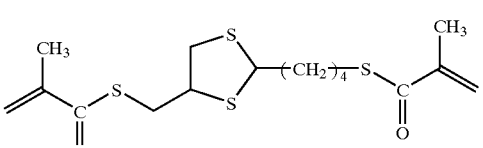 |

The acrylic ester compound of the present invention represented by formula (1) is suitably produced by a variety of esterification processes, the reactions therefor being by themselves known, using the sulfur-containing compound represented by formula (2) as a starting compound.

More specifically, these esterification processes may be represented by:

(1) reacting the compound represented by formula (2) with an acrylic ester; and (2) reacting the compound represented by formula (2) with a halopropionic acid (e.g., 3-chloropropionic, 3-bromopropionic, 3-chloro-2-methylpropionic, 3-bromo-2-methylpropionic acid) or its acid or acid halide to convert it into the halopropionic ester compound, and then dehydrohalogenating the above product into the acrylic ester:

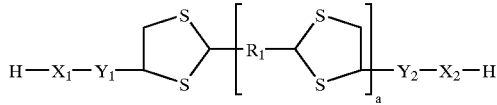

(2)

(wherein "a", $R_1$, $X_1$, $X_2$, $Y_1$ and $Y_2$ are same meanings as described above).

Moreover, "a", $R_1$, $X_1$, $X_2$, $Y_1$ and $Y_2$ in formula (2) for the present invention are the same as those in formula (1).

Of the sulfur-containing compounds represented by formula (2), those represented by formulae (2-a) to (2-d) are particularly preferable embodiments as the intermediates for the compounds represented by formula (1), where those represented by formulae (2-a), (2-b) and (2-c) are novel compounds:

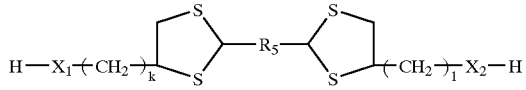

(2-a)

(wherein $R_5$ is a directly bonded single bond, alkylene group which may have a substituent, aralkylene group which may have a substituent, or arylene group which may have a substituent; "k" and "l" are each an integer of 1 to 4; and $X_1$ and $X_2$ are each an oxygen atom or a sulfur atom),

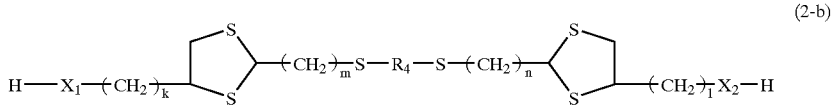

(2-b)

(wherein $R_4$ is an alkylene, aralkylene or arylene group, "k", "l", "m" and "n" are each an integer of 1 to 4; and $X_1$ and $X_2$ are each an oxygen atom or a sulfur atom),

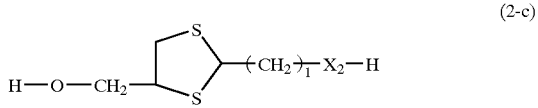

(2-c)

(wherein $X_2$ is an oxygen atom or a sulfur atom; and "l" is an integer of 1 to 4), and

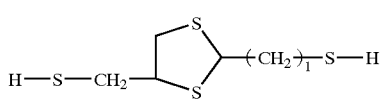

(2-d)

(wherein "l" is an integer of 1 to 4).

The specific examples of the sulfur-containing compounds represented by formula (2) are listed below, although those useful for the present invention are not limited thereto:

| Example Compound Nos | Compound Names |
| --- | --- |
| 2-a-1 | 2,2'-Bi(4-hydroxymethyl-1,3-dithiolan) |
| 2-a-2 | 1,1-Bis(4-hydroxymethyl-1,3-dithiolan-2-yl)methane |
| 2-a-3 | 1,2-Bis(4-hydroxymethyl-1,3-dithiolan-2-yl)ethane |
| 2-a-4 | 1,3-Bis(4-hydroxymethyl-1,3-dithiolan-2-yl)propane |
| 2-a-5 | 1,4-Bis(4-hydroxymethyl-1,3-dithiolan-2-yl)butane |
| 2-a-6 | 1,6-Bis(4-hydroxymethyl-1,3-dithiolan-2-yl)hexane |
| 2-a-7 | 1,4-Bis[(4-hydroxymethyl-1,3-dithiolan-2-yl)methyl]cyclohexane |
| 2-a-8 | 1,4-Bis[(4-hydroxymethyl-1,3-dithiolan-2-yl)methyl]benzene |
| 2-a-9 | 1,3-Bis[(4-hydroxymethyl-1,3-dithiolan-2-yl)methyl]benzene |
| 2-a-10 | 1,2-Bis[(4-hydroxymethyl-1,3-dithiolan-2-yl)methyl]benzene |
| 2-a-11 | 1,4-Bis(4-hydroxymethyl-1,3-dithiolan-2-yl)benzene |
| 2-a-12 | 1,3-Bis(4-hydroxymethyl-1,3-dithiolan-2-yl)benzene |
| 2-a-13 | 1,2-Bis(4-hydroxymethyl-1,3-dithiolan-2-yl)benzene |
| 2-a-14 | 2,2'-Bis(4-hydroxymethyl-1,3-dithiolan-2-yl)biphenyl |
| 2-a-15 | 2,2'-Bis(4-hydroxymethyl-1,3-dithiolan-2-yl)diphenylether |
| 2-a-16 | 2,3-Bis(4-hydroxymethyl-1,3-dithiolan-2-yl)naphthalene |
| 2-a-17 | 2,6-Bis(4-hydroxymethyl-1,3-dithiolan-2-yl)naphthalene |
| 2-a-18 | 2,5-Bis(4-hydroxymethyl-1,3-dithiolan-2-yl)furan |
| 2-a-19 | 2,5-Bis(4-hydroxymethyl-1,3-dithiolan-2-yl)thiophene |
| 2-a-20 | 3,4-Bis(4-hydroxymethyl-1,3-dithiolan-2-yl)thiophene |
| 2-a-21 | 2,2'-Bi(4-mercaptomethyl-1,3-dithiolan) |
| 2-a-22 | 1,1-Bis(4-mercaptomethyl-1,3-dithiolan-2-yl)methane |
| 2-a-23 | 1,2-Bis(4-mercaptomethyl-1,3-dithiolan-2-yl)ethane |
| 2-a-24 | 1,3-Bis(4-mercaptomethyl-1,3-dithiolan-2-yl)propane |
| 2-a-25 | 1,4-Bis(4-mercaptomethyl-1,3-dithiolan-2-yl)butane |
| 2-a-26 | 1,6-Bis(4-mercaptomethyl-1,3-dithiolan-2-yl)hexane |
| 2-a-27 | 1,4-Bis[(4-mercaptomethyl-1,3-dithiolan-2-yl)methyl]cyclohexane |
| 2-a-28 | 1,4-Bis[(4-mercaptomethyl-1,3-dithiolan-2-yl)methyl]benzene |
| 2-a-29 | 1,3-Bis[(4-mercaptomethyl-1,3-dithiolan-2-yl)methyl]benzene |
| 2-a-30 | 1,2-Bis[(4-mercaptomethyl-1,3-dithiolan-2-yl)methyl]benzene |
| 2-a-31 | 1,4-Bis(4-mercaptomethyl-1,3-dithiolan-2-yl)benzene |
| 2-a-32 | 1,3-Bis(4-mercaptomethyl-1,3-dithiolan-2-yl)benzene |
| 2-a-33 | 1,2-Bis(4-mercaptomethyl-1,3-dithiolan-2-yl)benzene |
| 2-a-34 | 2,2'-Bis(4-mercaptomethyl-1,3-dithiolan-2-yl)biphenyl |
| 2-a-35 | 2,2'-Bis(4-mercaptomethyl-1,3-dithiolan-2-yl)diphenyl ether |
| 2-a-36 | 2,3-Bis(4-mercaptomethyl-1,3-dithiolan-2-yl)naphthalene |
| 2-a-37 | 2,6-Bis(4-mercaptomethyl-1,3-dithiolan-2-yl)naphthalene |
| 2-a-38 | 2,5-Bis(4-mercaptomethyl-1,3-dithiolan-2-yl)furan |
| 2-a-39 | 2,5-Bis(4-mercaptomethyl-1,3-dithiolan-2-yl)thiophene |
| 2-a-40 | 3,4-Bis(4-mercaptomethyl-1,3-dithiolan-2-yl)thiophene |
| 2-a-41 | 2,2'-Bi[4-(2-hydroxyethyl)-1,3-dithiolan] |
| 2-a-42 | 1,3-Bis[4-(2-hydroxyethyl)-1,4-dithiolan-2-yl]benzene |
| 2-a-43 | 2,2'-Bi[4-(2-mercaptoethyl)-1,3-dithiolan] |
| 2-a-44 | 1,1-Bis[4-(3-mercaptopropyl)-1,3-dithiolan-2-yl]methane |
| 2-a-45 | 1,3-Bis[4-(2-mercaptobutyl)-1,3-dithiolan-2-yl]benzene |
| 2-a-46 | 4-Hydroxy-4'-mercapto-2,2'-bi(1,3-dithiolan) |
| 2-a-47 | 1-(4-Mercaptomethyl-1,3-dithiolan-2-yl)-1-(4-hydroxymethyl-1,3-dithiolan-2-yl)methane |
| 2-a-48 | 1-(4-Mercaptomethyl-1,3-dithiolan-2-yl)-2-(4-metamercaptomethyl-1,3-dithiolan-2-yl)ethane |
| 2-a-49 | 1-(4-Mercaptomethyl-1,3-dithiolan-2-yl)-4-(4-metahydroxythiomethyl-1,3-dithiolan-2-yl)benzene |
| 2-a-50 | 1-(4-Metamercaptomethyl-1,3-dithiolan-2-yl)-4-(4-hydroxythiomethyl-1,3-dithiolan-2-yl)benzene |
| 2-b-1 | Bis[(4-hydroxymethyl-1,3-dithiolan-2-yl)methylthio]methane |
| 2-b-2 | 1,1-Bis[(4-hydroxymethyl-1,3-dithiolan-2-yl)methylthio]ethane |
| 2-b-3 | 1,2-Bis[(4-hydroxymethyl-1,3-dithiolan-2-yl)methylthio]ethane |
| 2-b-4 | 1,3-Bis[(4-hydroxymethyl-1,3-dithiolan-2-yl)methylthio]propane |

| Example Compound Nos | Compound Names |
|---|---|
| 2-b-5 | 1,2-Bis[(4-hydroxymethyl-1,3-dithiolan-2-yl)-methylthio]propane |
| 2-b-6 | 2,2-Bis[(4-hydroxymethyl-1,3-dithiolan-2-yl)-methylthio]propane |
| 2-b-7 | 1,4-Bis[(4-hydroxymethyl-1,3-dithiolan-2-yl)-methylthio]butane |
| 2-b-8 | 1,5-Bis[(4-hydroxymethyl-1,3-dithiolan-2-yl)-methylthio]pentane |
| 2-b-9 | 1,6-Bis[(4-hydroxymethyl-1,3-dithiolan-2-yl)-methylthio]hexane |
| 2-b-10 | 1,8-Bis[(4-hydroxymethyl-1,3-dithiolan-2-yl)-methylthio]octane |
| 2-b-11 | 1,4-Bis[(4-hydroxymethyl-1,3-dithiolan-2-yl)-methylthio]cyclohexane |
| 2-b-12 | 1,3-Bis[(4-hydroxymethyl-1,3-dithiolan-2-yl)-methylthio]cyclohexane |
| 2-b-13 | 1,2-Bis[(4-hydroxymethyl-1,3-dithiolan-2-yl)-methylthio]cyclohexane |
| 2-b-14 | 1,4-Bis[(4-hydroxymethyl-1,3-dithiolan-2-yl)-methylthiomethyl]cyclohexane |
| 2-b-15 | 1,3-Bis[(4-hydroxymethyl-1,3-dithiolan-2-yl)-methylthiomethyl]cyclohexane |
| 2-b-16 | 1,2-Bis[(4-hydroxymethyl-1,3-dithiolan-2-yl)-methylthiomethyl]cyclohexane |
| 2-b-17 | 1,4-Bis[(4-hydroxymethyl-1,3-dithiolan-2-yl)-methylthiomethyl]benzene |
| 2-b-18 | 1,3-Bis[(4-hydroxymethyl-1,3-dithiolan-2-yl)-methylthiomethyl]benzene |
| 2-b-19 | 1,2-Bis[(4-hydroxymethyl-1,3-dithiolan-2-yl)-methylthiomethyl]benzene |
| 2-b-20 | 1,4-Bis[1'-(4-hydroxymethyl-1,3-dithiolan-2-yl)-methylthioethyl]benzene |
| 2-b-21 | 1,3-Bis[1'-(4-hydroxymethyl-1,3-dithiolan-2-yl)-methylthioethyl]benzene |
| 2-b-22 | 1,2-Bis[1'-(4-hydroxymethyl-1,3-dithiolan-2-yl)-methylthioethyl]benzene |
| 2-b-23 | 1,4-Bis[2'-(4-hydroxymethyl-1,3-dithiolan-2-yl)-methylthioethyl]benzene |
| 2-b-24 | 1,3-Bis[2'(4-hydroxymethyl-1,3-dithiolan-2-yl)-methylthioethyl]benzene |
| 2-b-25 | 1,2-Bis[2'-(4-hydroxymethyl-1,3-dithiolan-2-yl)-methylthioethyl]benzene |
| 2-b-26 | 1,4-Bis[2'-(4-hydroxymethyl-1,3-dithiolan-2-yl)-methylthio]benzene |
| 2-b-27 | 1,3-Bis[2'(4-hydroxymethyl-1,3-dithiolan-2-yl-)methylthio]benzene |
| 2-b-28 | 1,2-Bis[2'-(4-hydroxymethyl-1,3-dithiolan-2-yl)-methylthio]benzene |
| 2-b-29 | 1,4-Bis[2'-(4-hydroxymethyl-1,3-dithiolan-2-yl)-methylthio]naphthalene |
| 2-b-30 | 1,5-Bis[2'-(4-hydroxymethyl-1,3-dithiolan-2-yl)-methylthio]naphthalene |
| 2-b-31 | 2,6-Bis[2'-(4-hydroxymethyl-1,3-dithiolan-2-yl)-methylthio]naphthalene |
| 2-b-32 | 1,5-Bis[2'-(4-hydroxymethyl-1,3-dithiolan-2-yl)-methylthio]naphthalene |
| 2-b-33 | 2,7-Bis[2'-(4-hydroxymethyl-1,3-dithiolan-2-yl)-methylthio]naphthalene |
| 2-b-34 | 2,5-Bis[2'-(4-hydroxymethyl-1,3-dithiolan-2-yl)-methylthio]thiophene |
| 2-b-35 | 3,4-Bis[2'-(4-hydroxymethyl-1,3-dithiolan-2-yl)-methylthio]thiophene |
| 2-b-36 | Bis[(4-mercaptomethyl-1,3-dithiolan-2-yl)-methylthio]methane |
| 2-b-37 | 1,1-Bis[(4-mercaptomethyl-1,3-dithiolan-2-yl)-methylthio]ethane |
| 2-b-38 | 1,2-Bis[(4-mercaptomethyl-1,3-dithiolan-2-yl)-methylthio]ethane |
| 2-b-39 | 1,3-Bis[(4-mercaptomethyl-1,3-dithiolan-2-yl)-methylthio]propane |
| 2-b-40 | 1,2-Bis[(4-mercaptomethyl-1,3-dithiolan-2-yl)-methylthio]propane |
| 2-b-41 | 2,2-Bis[(4-mercaptomethyl-1,3-dithiolan-2-yl)-methylthio]propane |
| 2-b-42 | 1,4-Bis[(4-mercaptomethyl-1,3-dithiolan-2-yl)-methylthio]butane |
| 2-b-43 | 1,5-Bis[(4-mercaptomethyl-1,3-dithiolan-2-yl)-methylthio]pentane |
| 2-b-44 | 1,6-Bis[(4-mercaptomethyl-1,3-dithiolan-2-yl)-methylthio]hexane |
| 2-b-45 | 1,8-Bis[(4-mercaptomethyl-1,3-dithiolan-2-yl)-methylthio]octane |
| 2-b-46 | 1,4-Bis[(4-mercaptomethyl-1,3-dithiolan-2-yl)-methylthio]cyclohexane |
| 2-b-47 | 1,3-Bis[(4-mercaptomethyl-1,3-dithiolan-2-yl)-methylthio]cyclohexane |
| 2-b-48 | 1,2-Bis[(4-mercaptomethyl-1,3-dithiolan-2-yl)-methylthio]cyclohexane |
| 2-b-49 | 1,4-Bis[(4-mercaptomethyl-1,3-dithiolan-2-yl)-methylthiomethyl]cyclohexane |
| 2-b-50 | 1,3-Bis[(4-mercaptomethyl-1,3-dithiolan-2-yl)-methylthiomethyl]cyclohexane |
| 2-b-51 | 1,2-Bis[(4-mercaptomethyl-1,3-dithiolan-2-yl)-methylthiomethyl]cyclohexane |
| 2-b-52 | 1,4-Bis[(4-mercaptomethyl-1,3-dithiolan-2-yl)-methylthiomethyl]benzene |
| 2-b-53 | 1,3-Bis[(4-mercaptomethyl-1,3-dithiolan-2-yl)-methylthiomethyl]benzene |
| 2-b-54 | 1,2-Bis[(4-mercaptomethyl-1,3-dithiolan-2-yl)-methylthiomethyl]benzene |
| 2-b-55 | 1,4-Bis[1'-(4-mercaptomethyl-1,3-dithiolan-2-yl)methylthioethyl]benzene |
| 2-b-56 | 1,3-Bis[1'-(4-mercaptomethyl-1,3-dithiolan-2-yl)methylthioethyl]benzene |
| 2-b-57 | 1,2-Bis[1'-(4-mercaptomethyl-1,3-dithiolan-2-yl)methylthioethyl]benzene |
| 2-b-58 | 1,4-Bis[2'-(4-mercaptomethyl-1,3-dithiolan-2-yl)methylthioethyl]benzene |
| 2-b-59 | 1,3-Bis[2'-(4-mercaptomethyl-1,3-dithiolan-2-yl)methylthioethyl]benzene |
| 2-b-60 | 1,2-Bis[2'-(4-mercaptomethyl-1,3-dithiolan-2-yl)methylthioethyl]benzene |
| 2-b-61 | 1,4-Bis[2'-(4-mercaptomethyl-1,3-dithiolan-2-yl)methylthio]benzene |
| 2-b-62 | 1,3-Bis[2'-(4-mercaptomethyl-1,3-dithiolan-2-yl)methylthio]benzene |
| 2-b-63 | 1,2-Bis[2'-(4-mercaptomethyl-1,3-dithiolan-2-yl)methylthio]benzene |
| 2-b-64 | 1,4-Bis[2'-(4-mercaptomethyl-1,3-dithiolan-2-yl)methylthio]naphthalene |
| 2-b-65 | 1,5-Bis[2'-(4-mercaptomethyl-1,3-dithiolan-2-yl)methylthio]naphthalene |
| 2-b-66 | 2,6-Bis[2'-(4-mercaptomethyl-1,3-dithiolan-2-yl)methylthio]naphthalene |
| 2-b-67 | 1,5-Bis[2'-(4-mercaptomethyl-1,3-dithiolan-2-yl)methylthio]naphthalene |
| 2-b-68 | 2,7-Bis[2'-(4-mercaptomethyl-1,3-dithiolan-2-yl)methylthio]naphthalene |
| 2-b-69 | 2,5-Bis[2'-(4-mercaptomethyl-1,3-dithiolan-2-yl)methylthio]thiophene |
| 2-b-70 | 3,4-Bis[2'-(4-mercaptomethyl-1,3-dithiolan-2-yl)methylthio]thiophene |
| 2-b-71 | Bis[(4-hydroxyethyl-1,3-dithiolan-2-yl)-methylthio]methane |
| 2-b-72 | 1,2-Bis[(4-hydroxypropyl-1,3-dithiolan-2-yl)-methylthio]ethane |
| 2-b-73 | 1,4-Bis[(4-hydroxybutyl-1,3-dithiolan-2-yl)-methylthiomethyl]cyclohexane |
| 2-b-74 | 1,4-Bis[(4-hydroxyethyl-1,3-dithiolan-2-yl)-methylthiomethyl]benzene |
| 2-b-75 | 1,4-Bis[2'-(4-hydroxyethyl-1,3-dithiolan-2-yl)-methylthio]benzene |
| 2-b-76 | 2,5-Bis[2'-(4-hydroxyethyl-1,3-dithiolan-2-yl)-methylthio]thiophene |
| 2-b-77 | Bis[(4-hydroxymethyl-1,3-dithiolan-2-yl)-ethylthio]methane |
| 2-b-78 | 1,2-Bis[(4-hydroxymethyl-1,3-dithiolan-2-yl)-propylthio]ethane |

-continued

| Example Compound Nos | Compound Names |
|---|---|
| 2-b-79 | 1,4-Bis[(4-hydroxymethyl-1,3-dithiolan-2-yl)-butylthiomethyl]cyclohexane |
| 2-b-80 | 1,4-Bis[(4-hydroxymethyl-1,3-dithiolan-2-yl)-ethylthiomethyl]benzene |
| 2-b-81 | 1,4-Bis[2'-(4-hydroxymethyl-1,3-dithiolan-2-yl)butylthio]benzene |
| 2-b-82 | 2,5-Bis[2'-(4-hydroxymethyl-1,3-dithiolan-2-yl)ethylthio]thiophene |
| 2-b-83 | Bis[(4-mercaptoethyl-1,3-dithiolan-2-yl)-methylthio]methane |
| 2-b-84 | 1,2-Bis[(4-mercaptopropyl-1,3-dithiolan-2-yl)-methylthio]ethane |
| 2-b-85 | 1,4-Bis[(4-mercaptobutyl-1,3-dithiolan-2-yl)-methylthiomethyl]cyclohexane |
| 2-b-86 | 1,4-Bis[(4-mercaptoethyl-1,3-dithiolan-2-yl)-methylthiomethyl]benzene |
| 2-b-87 | 1,4-Bis[2'-(4-mercaptoethyl-1,3-dithiolan-2-yl)methylthio]benzene |
| 2-b-88 | 2,5-Bis[2'-(4-mercaptoethyl-1,3-dithiolan-2-yl)methylthio]thiophene |
| 2-b-89 | Bis[(4-mercaptomethyl-1,3-dithiolan-2-yl)-ethylthio]methane |
| 2-b-90 | 1,2-Bis[(4-mercaptomethyl-1,3-dithiolan-2-yl)-propylthio]ethane |
| 2-b-91 | 1,4-Bis[(4-mercaptomethyl-1,3-dithiolan-2-yl)-butylthiomethyl]cyclohexane |
| 2-b-92 | 1,4-Bis[(4-mercaptomethyl-1,3-dithiolan-2-yl)-ethylthiomethyl]benzene |
| 2-b-93 | 1,4-Bis[2'-(4-mercaptomethyl-1,3-dithiolan-2-yl)butylthio]benzene |
| 2-b-94 | 2,5-Bis[2'-(4-mercaptomethyl-1,3-dithiolan-2-yl)ethylthio]thiophene |
| 2-b-95 | Bis[(4-metamercaptomethyl-1,3-dithiolan-2-yl)-ethylthio]methane |
| 2-b-96 | 1-[(4-Hydroxymethyl-1,3-dithiolan-2-yl)-methylthio]-1-[(4-mercaptomethyl-1,3-dithiolan-2-yl)methylthio]ethane |
| 2-b-97 | 1-[(4-Mercaptomethyl-1,3-dithiolan-2-yl)-methylthiomethyl]-4-[(4-mercaptoethyl-1,3-dithiolan-2-yl)methylthiomethyl]cyclohexane |
| 2-b-98 | 1-[(4-Mercaptothiomethyl-1,3-dithiolan-2-yl)-methylthiomethyl]-4-[(4-mercaptomethyl-1,3-dithiolan-2-yl)ethylthiomethyl]benzene |

Moreover, the specific examples of the sulfur-containing compounds represented by formulae (2-c) and (2-d) are listed below:

| Example Compound Nos. | Structural Formulae |
|---|---|
| 2-c-1 | HO~~\~~S~~\~~S~~\~~OH (1,3-dithiolane with HO-CH2 and CH2-OH) |
| 2-c-2 | HO~~\~~dithiolane~~\~~(CH2)2-OH |
| 2-c-3 | HO~~\~~dithiolane~~\~~(CH2)3-OH |
| 2-c-4 | HO~~\~~dithiolane~~\~~(CH2)4-OH |
| 2-c-5 | HO~~\~~dithiolane~~\~~CH2-SH |
| 2-c-6 | HO~~\~~dithiolane~~\~~(CH2)2-SH |
| 2-c-7 | HO~~\~~dithiolane~~\~~(CH2)3-SH |
| 2-c-8 | HO~~\~~dithiolane~~\~~(CH2)4-SH |
| 2-d-1 | HS~~\~~dithiolane~~\~~CH2-SH |
| 2-d-2 | HS~~\~~dithiolane~~\~~(CH2)2-SH |
| 2-d-3 | HS~~\~~dithiolane~~\~~(CH2)3-SH |
| 2-d-4 | HS~~\~~dithiolane~~\~~(CH2)4-SH |

Next, the process for producing the sulfur-containing compound for the present invention represented by formula (2) will be described.

Of the sulfur-containing compounds represented by formula (2), the one represented by formula (2-a) is typically produced by, e.g., a synthesis route of Scheme A, shown below:

Scheme A

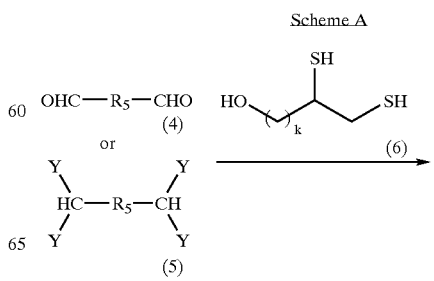

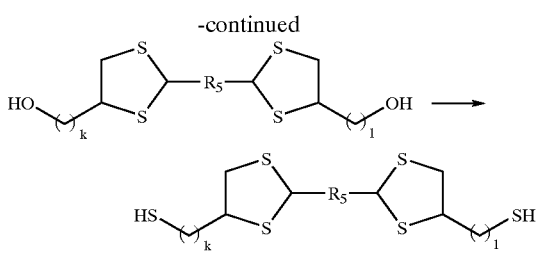

(in Scheme A, $R_5$, "k" and "l" are the same as those described earlier; and Y is a chlorine atom or a bromine atom).

In the process of Scheme A, a dialdehyde compound represented by formula (4) or its acetal derivative, or tetrahalogen compound represented by formula (5) is used as a starting compound, which is reacted with a dimercaptoalkylhydroxy compound represented by formula (6), to produce a compound represented by formula (2-a) in which $X_1$ and $X_2$ are each an oxygen atom. The reaction to form a dithiolan ring can be effected in a manner similar to the process described in Journal of Chemical Society (C), pp. 415–419 (1969) as the basis.

Then, the hydroxy group in the dihydroxy compound is converted into the mercapto group by a known process (e.g., reaction with thiourea under an acidic condition and hydrolyzing the resultant thiuronium salt), to produce a sulfur-containing compound of the present invention represented by formula (2-a) in which $X_1$ and $X_2$ are each a sulfur atom. The conversion of a hydroxy compound into a thiol (mercapto) compound is suitably effected by a known process, e.g., the one disclosed by Journal of Chemical Society, Vol. 68, 2103–2104 (1946), Journal of Organic Chemistry, Vol. 27, 93–95 (1962), or organic synthesis, V, 401–403 (1963).

Of the sulfur-containing compounds represented by formula (2), the one represented by formula (2-b) is typically produced by, e.g., a synthesis route of Scheme B, shown below:

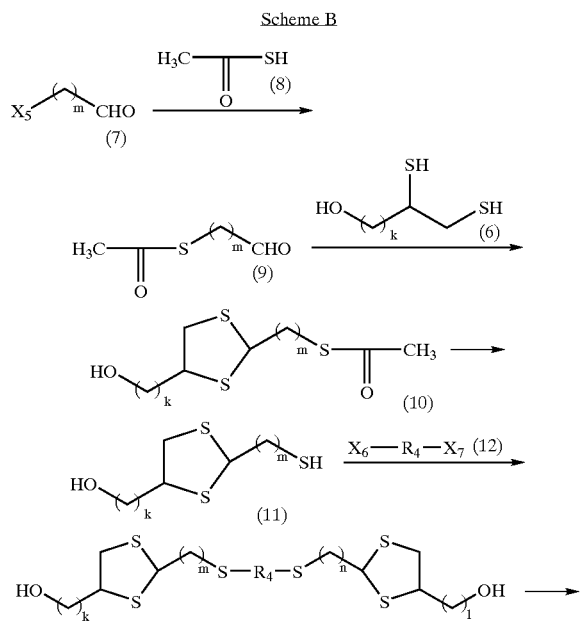

(in Scheme B, $R_4$, "k", "l", "m" and "n" are the same as those described earlier; and $X_5$, $X_6$ and $X_7$ are each a chlorine atom or a bromine atom).

In Scheme B, the thioacetic acid represented by formula (8) or its salt (e.g., sodium, potassium or lithium salt) is acted on the haloalkyl aldehyde represented by formula (7) or its acetal derivative as a starting compound, to produce a compound represented by formula (9). Then, the product compound is reacted with the dimercaptohydroxy compound represented by formula (6) (representatively 2,3-mercaptio-1-propnaol or the like) in the presence of an acidic catalyst or the like to produce a compound containing a dithiolan ring represented by formula (10), and the acetylthio acid of the dithiolan-containnng compound is hydrolyzed under an acidic or basic condition, to produce a compound represented by formula (11), or by formula (2) in which a is 0, $X_1$ and $X_2$ are an oxygen atom and a sulfur atom, respectively, $Y_1$ is a —$(CH_2)_k$— group ("k" is an integer of 1 to 4) and $Y_2$ is a —$(CH_2)_l$— group ("l" is an integer of 1 to 4).

The compound represented by formula (11) is reacted with the dihalogen compound represented by formula (12) to produce a sulfur-containing compound for the present invention represented by formula (2-b) in which each of $X_1$ and $X_2$ is an oxygen atom.

Moreover, the hydroxy group is converted into the mercapto group by a known process (e.g., reaction with thiourea under an acidic condition and hydrolyzing the resultant thiuronium salt), to produce a sulfur-containing compound of the present invention represented by formula (2-b) in which $X_1$ and $X_2$ are each a sulfur atom. Such a process is described in detail in Japanese Patent Laid-open Publication No. 6-16657, as described earlier.

Of the sulfur-containing compounds represented by formula (2), the one represented by each of formulae (2-c) and (2-d) is similarly produced by a synthesis route of Scheme B. Moreover, the one represented by formula (2-c) can be also produced by acting the dithiol compound (6-1), which is the one represented by formula (6) in which "k" is 1, on the aldehyde compound represented by formula (7) in the presence of catalyst to produce a compound represented by formula (3), and then converting the halogen atom represented by $X_3$ in formula (3) into the hydroxy group by a known synthesis process, e.g., hydrolysis, to produce a compound represented by formula (2-c) in which $X_2$ is an oxygen atom. Still more, the compound represented by formula (2-c) in which $X_2$ is a sulfur atom can be produced by converting the halogen atom represented by $X_3$ in formula (3) into the thiol group by a known synthesis process, e.g., acting thiourea on the halogen atom to produce a thiuronium salt and hydrolyzing the salt in the presence of alkali:

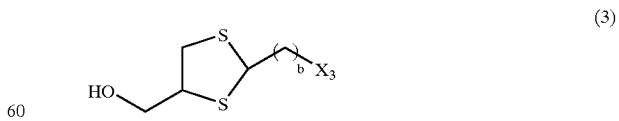

(3)

(wherein $X_3$ is a halogen atom; and "b" is an integer of 1 to 4).

In the above formula (3), the halogen atom represented by $X_3$ is preferably chlorine or bromine.

As described above, the sulfur-containing compound represented by formula (3) can be produced by acting the dithiol compound (6-1), which is the one represented by formula (6) in which "k" is 1, on the aldehyde compound represented by formula (7) or its acetal derivative in the presence of catalyst. This process will be described in more detail.

The aldehyde compounds represented by formula (7) or their acetal derivatives include haloalkylaldehydes, e.g., chloroacetoaldehyde, 3-chloropropionaldehyde, 3-bromopropionaldehyde, 4-chlorobutylaldehyde and 4-bromobutylaldehyde; dialkyl acetal and cyclic alkylene acetal derivatives of haloalkyl aldehydes, e.g., 2-chloroacetoaldehyde dimethylacetal, 2-chloroacetoaldehyde diethylacetal, 2-chloropropionaldehyde dimethylacetal, 2-chloropropionaldehyde diethylacetal, 2-bromopropionaldehyde dimethylacetal, 2-bromopropionaldehyde diethylacetal, 2-bromopropionaldehyde diethyleneacetal [or 2-(2'-bromoethyl)-1,3-dioxolan], and 2-bromopropionaldehyde dimethyleneacetal [or 2-(2'-bromoethyl)-1,3-dioxolan].

Quantity of the dithiol compound (6-1) for production of the sulfur-containing compound represented by formula (3), where the compound represented by formula (6-1) is acted on the aldehyde or its acetal derivative represented by formula (7), is not limited. However, it is normally incorporated at 0.1 to 10 mols per mol of the compound represented by formula (7), preferably 0.5 to 5 mols, more preferably 0.7 to 3 mols, still more preferably 0.8 to 2 mols.

The above reaction may be effected in the absence of catalyst, but preferably in the presence of catalyst in consideration of reaction temperature, reaction time or the like. The catalysts useful for the present invention include acid catalysts, e.g., protonic acids, such as inorganic acids (e.g., hydrochloric acid, hydrogen chloride, hydrobromic acid, sulfuric acid, nitric acid, boric acid and phosphoric acid), and organic acids (e.g., acetic acid, propionic acid, oxalic acid, methanesulfonic acid, trifluoromethanesulfonic acid, benzenesulfonic acid and p-toluenesulfonic acid), and lewis acids (e.g., titanium trichloride, titanium tetrachloride, tin dichloride, tin tetrachloride, zinc chloride, aluminum chloride and boron trifluoride/ether complex).

Quantity of the catalyst is not limited. However, it is normally incorporated at 0.001 to 20 mols per mol of the aldehyde compound represented by formula (7) or its acetal derivative, preferably 0.01 to 10 mols, more preferably 0.1 to 5 mols. These catalysts may be used either singly or in combination.

The reaction may be effected either in the presence or absence of solvent. The solvent, when used, is not limited so long as it is inert to the reaction. The solvents useful for the present invention include hydrocarbon-based ones, e.g., benzene, toluene and xylene; halogen-based ones, e.g., methylene chloride, chloroform, 1,2-dichloroethane, chlorobenzene and dichlorobenzene; and ether-based ones, e.g., diethyl ether, tetrahydrofuran, dioxane and diethylene glycol dimethyl ether. These solvents may be used either singly or in combination.

Quantity of the reaction solvent is not limited. However, an excessively large quantity is undesirable in view of production efficiency or the like. It is normally incorporated at 300 parts by weight or less per part of the aldehyde compound or its acetal derivative, preferably 100 parts or less.

The reaction may be also effected either under air or an inert gas atmosphere, preferably under an inert gas (e.g., nitrogen or argon) atmosphere, to prevent troubles, e.g., coloration of the product.

The reaction temperature is not limited. However, it is preferably in a range from 0° C. to boiling point of the solvent.

The reaction time may be normally in a range from several minutes to 10 hours or more, although varying depending on reaction time or the like. The reaction can be followed by a known analytical procedure (e.g., liquid chromatography, thin-film chromatography or IR), to determine the end of the reaction.

The compound represented by formula (3) is also a novel compound, and included in the present invention. The specific examples of the sulfur-containing compounds represented by formula (3) are listed below:

| Example Compound Nos. | Structural Formulae |
|---|---|
| 3-1 | HO–⟨S,S⟩–CH$_2$Br |
| 3-2 | HO–⟨S,S⟩–(CH$_2$)$_2$–Br |
| 3-3 | HO–⟨S,S⟩–(CH$_2$)$_3$–Br |
| 3-4 | HO–⟨S,S⟩–(CH$_2$)$_4$–Br |
| 3-5 | HO–⟨S,S⟩–CH$_2$Cl |
| 3-6 | HO–⟨S,S⟩–(CH$_2$)$_2$–Cl |
| 3-7 | HO–⟨S,S⟩–(CH$_2$)$_3$–Cl |
| 3-8 | HO–⟨S,S⟩–(CH$_2$)$_4$–Cl |

Of the above-described processes for producing the acrylic ester compound represented by formula (1) by reacting the sulfur-containing compound represented by formula (2) with the acrylic acid [e.g., (meth)acrylic acid, its ester derivative, or its acid halide], the representative ones are described in more detail.

A variety of known processes as esterification processes, e.g., those described in Jikken Kagaku Koza (edited by Chemical Society of Japan), 19, 471–482 (1957), Journal of Organic Chemistry, Vol. 45, pp. 5364 (1980) and European Polymer Journal, Vol. 19, pp. 399 (1983), are cited as those useful for the present invention.

More specifically, the following two procedures can be cited as the representative ones:

((1)-a): An acid halide of (meth)acrylic acid is acted on, e.g., added dropwise to, the sulfur-containing compound represented by formula (2) with stirring in the presence of base.

((1)-b): The sulfur-containing compound represented by formula (2) is reacted with a (meth)acrylic ester derivative [e.g., alkyl (meth)acrylic ester, such as methyl, ethyl, butyl (meth)acrylic ester] for interesterification in the presence of catalyst (acidic or basic).

Of these processes, the former ((1)-a) process is more preferable, when the sulfur-containing compound represented by formula (2) has a thiol group, because of its relatively low reaction temperature to prevent addition of the (meth)acrylic acid as the other starting compound to an unsaturated double bond as the side-reaction of the desired esterification.

Quantity the acrylic acid [e.g., (meth)acrylic acid, its ester derivative, or its acid halide] to be acted on the sulfur-containing compound represented by formula (2) for the above reaction is not limited. However, it is normally incorporated at 0.1 to 5 mols per mol of the sulfur-containing compound, preferably 0.25 to 2.5 mols, more preferably 0.5 to 1.5 mols.

The reaction may be effected either in the absence of solvent or in the presence of an inert solvent. The solvents useful for the present invention include hydrocarbon-based ones, e.g., n-hexane, benzene and toluene; ketone-based ones, e.g., acetone, methylethylketone and methylisobutylketone; ester-based ones, e.g., ethyl and butyl acetate; ether-based ones, e.g., diethyl ether, tetrahydrofuran and dioxane; halogen-based ones, e.g., dichloromethane, chloroform, carbon tetrachloride, 1,2-dichloroethane and tetrachloroethylene; and polar ones, e.g., acetonitrile, N,N-dimethylformamide, N,N-dimethylacetoamide and N,N-dimethylimidazoline. These solvents may be used either individually or in combination.

The reaction temperature is not limited. However, it should be the level at which the acrylic acid as the starting compound or acrylic ester as the reaction product is not polymerized, and normally in a range from −78 to 150° C., preferably −20 to 120° C., more preferably −10 to 100° C., still more preferably 0 to 50° C.

The reaction time, which varies depending on reaction temperature, is not limited. However, it is normally in a range from several minutes to 100 hours, preferably 30 minutes to 50 hours, more preferably 1 to 20 hours. The reaction can be followed by a known analytical procedure (e.g., liquid chromatography, thin-film chromatography or IR), to determine the end of the reaction.

When the acrylic ester compound of the present invention represented by formula (1) is produced by reacting the sulfur-containing compound represented by formula (2) with an acid halide of acrylic acid, an inert gas (e.g., nitrogen or argon) may be blown into the reaction system to purge hydrogen halide (e.g., hydrogen chloride) as a by-product out of the system, or a dehydrohalogenating agent may be used.

The dehydrohalogenating agents useful for the present invention include organic bases, e.g., triethylamine, pyridine, picoline, dimethylaniline, diethylaniline, 1,4-diazabicyclo[2.2.2]octane (DABCO) and 1,8-diazabicyclo[5.4.0]undeca-7-ene (DBU); and inorganic bases, e.g., sodium hydrogen carbonate, sodium carbonate, potassium carbonate, lithium carbonate, sodium hydroxide, potassium hydroxide, calcium hydroxide and magnesium oxide.

Quantity of the dehydrohalogenating agent is not limited. However, it is incorporated at 0.05 to 10 mols per mol of the sulfur-containing compound represented by formula (2), preferably 0.05 to 5 mols, more preferably 0.5 to 3 mols.

The ((1)-b) process is more preferable to produce the acrylate ester compound represented by formula (1) in which $X_1$ and $X_2$ are each a sulfur atom.

The acrylate ester compound represented by formula (1) can be produced by reacting the sulfur-containing compound represented by formula (2), in which $X_1$ and $X_2$ are each a sulfur atom, with a halopropionic acid or its acid halide to produce a halopropionic ester compound, and then by dehydrohalogenating the product ester. Such a process is disclosed by, e.g., Japanese Patent Application Laid-open No. 10-67736.

When the acrylic ester compound of the present invention represented by formula (1) is produced, it is preferable to use a polymerization inhibitor to prevent polymerization of the product during or after the reaction process.

Examples of the polymerization inhibitors include known compounds, e.g., 2,6-di-tert-butyl-cresol, 4-methoxy phenol, hydroquinone and phenothiazine. Quantity of the polymerization inhibitor is not limited. However, it is normally incorporated at 0.01 to 5% by weight on the starting mixture in the reaction system or reaction product, preferably 0.05 to 3% by weight.

On completion of the reaction, the acrylic ester compound of the present invention represented by formula (1), as the reaction product, can be suitably isolated from the reaction system by a known operation or treatment procedure (e.g., neutralization, solvent extraction, water washing, fractionation or distillation to remove the solvent). Moreover, it may be further separated and/or purified, as required, to produce a higher-purity compound by a known procedure (e.g., chromatography, adsorption with the aid of activated carbon or the like, or recrystallization).

Next, the polymerizable composition containing, as the essential component, the acrylic ester compound of the present invention represented by formula (1), will be described in detail.

The polymerizable composition of the present invention, containing as the essential component the acrylic ester compound of the present invention represented by formula (1), and a polymerization initiator. The polymerization initiator is a compound which initiates polymerization of the polymerizable compound by light, heat or the like.

The polymerizable composition may be composed of the individual acrylic ester compound, or 2 or more of the different compounds represented by formula (1).

Moreover, the polymerizable composition of the present invention may contain one or more known polymerizable compounds (photopolymerizable or/and thermally polymerizable monomer(s) or oligomer(s)) other than the acrylic ester compound represented by formula (1), as required, within limits not harmful to the intended effect of the present invention.

Quantity of the acrylic ester compound represented by formula (1) in the polymerizable composition is not limited. However, it is normally incorporated at 10% by weight or more on the whole polymerizable composition, preferably 20% or more, more preferably 30% or more, still more preferably 50% or more.

The polymerization initiator is not limited for the polymerizable composition of the present invention, and may be selected from known initiators for photopolymerization or thermal polymerization.

The photopolymerization initiators useful for the present invention include: carbonyl compounds, e.g., benzophenone, 4-methylbenzophenone, 4,4'-dichlorobenzophenone, 2,4,6-trimethylbenzophenone, methyl o-benzoylbenzoate, 4-phenylbenzophenone, 4-(4-methyl-phenylthio)benzophenone, 3,3-dimethyl-4-methylbenzophenone, 4-(1,3-acryloyl-1,4,7,10,13-pentaoxa-tridecyl)benzophenone, 3,3',4,4'-tetra(tert-butylperoxy-carbonyl)benzophenone, 4-benzoyl-N,N,N-methylbenzene-methanaminium chloride, 2-hydroxy-3-(4-benzoylphenoxy)N,N,N-trimethyl-1-propanaminium chloride, 4-benzoyl-N,N-dimethyl-N-[(2-(1-oxo-2-propenoxy)ethyl)benzene methanaminium bromide, 4-benzoyl-N,N-dimethyl-N-[2-(1-oxo-2-propenyloxy)ethyl]benzene methanaminium bromide, 2-isopropylthioxanthone, 4-isopropylthioxanthone, 2,4-dimethylthioxanthone, 2,4-diethylthioxanthone, 2,4-diisopropylthioxanthone, 2,4-dichlorothioxanthone, 1-chloro-4-propoxythioxanthone, 2-hydroxy-3-(3,4-dimethyl-9-oxo9H-thioxanthon-2-yloxy)-N,N,N- thioxanthon-2yloxy)-N,N,N-trimethyl-1-propanaminium chloride and 2-benzoylmethylene-3-methylnaphtho(1,2-d) thiazoline; dicarbonyl compounds, e.g., benzyl, 1,7,7-trimethyl-bicyclo[2.2.1]heptane-2,3-dione (commonly referred to as camphorquinone), 2-methylanthraquinone, 2-ethylanthraquinone, 2-tert-butylanthraquinone, 1-chloroanthraquinone, 2-amylanthraquinone, 9,10-phenanthrenequinone and α-oxobenzene methyl acetate; acetophenone-based compounds, e.g., acetophenone, 2-hydroxy-2-methyl-1-phenylpropan-1-one, 1-(4-isopropylphenyl)-2-hydroxy-2-methylpropan-1-one, 1-[4-(2-hydroxy-ethoxy)phenyl]-2-hydroxy-2-methylpropan-1-one, 1-hydroxy-cyclohexylphenyl ketone, dimethoxyacetophenone, diethoxyacetophenone, dimethoxy-1,2-diphenylethan-1-one, 2,2-diethoxy-1,2-diphenylethan-1-one, 1,1-dichloro-acetophenone, N,N-dimethylaminoacetophenone, 2-methyl-1-(4-methylthiophenyl)-2-morpholinolpropan-1-one, 2-benzyl-2-dimethylamino-1-(4-morpholinophenyl)butan-1-one, 1-phenyl-1,2-propanedione-2-(o-ethoxycarbonyl)oxime and 3,6-bis(2-methyl-2-morpholinopropanoyl)-9-butylcarbazole; benzoin ether-based compounds, e.g., benzoin, benzoinmethyl ether, benzoinethyl ether, benzoinisopropyl ether, benzoin-n-butyl ether and benzoinisobutyl ether; aryl phosphine oxide-based compounds, e.g., 2,4,6-trimethylbenzoyldiphenyl phosphine oxide and bis(2,6-dichlorobenzoyl)-(4-n-propylphenyl)phosphine oxide; amino carbonyl compounds, e.g., methyl 4-dimethylamino-benzoate, ethyl 4-dimethylaminobenzoate, n-butoxyethyl 4-dimethylaminobenzoate, isoamyl 4-dimethylaminobenzoate, 2-dimethylaminoethylbenzoate, 4,4'-bisdimethylamino-benzophenone (Michler's ketone), 4,4'-bisdiethylamino-benzophenone and 2,5'-bis(4-dimethylaminobenzal)-cyclopentanone; halogen compounds, e.g., 2,2,2-trichloro-1-(4'-tert-butylphenyl)ethan-1-one, 2,2-dichloro-1-(4-phenoxyphenyl)ethan-1-one, α,α,α-tribromomethylphenylsulfone 2,4,6-tris (trichloromethyl)triazine, 2,4-bis(trichloromethyl)-6-(4-methoxyphenyl)triazine, 2,4-bis(trichloromethyl)-6-(4-methoxystyryl)triazine, 2,4-bis(trichloromethyl)-6-piperonyl-triazine, (2,4-bis(trichloromethyl)-6-(3,4-methylenedioxyphenyl)-triazine, 2,4-bis(trichloromethyl)-6-(4-methoxynaphthyl)-triazine, 2,4-bis(trichloromethyl)-6-[2-(5 5-methylfuryl)ethylidyne]triazine and 2,4-bis(trichloromethyl)-6-[2-furylethylidyne]triazine; and 9-phenylacridine, 2,2'-bis(o-chlorophenyl)-4,4',5,5'-tetraphenyl-1,2-biimidazole, 2,2-azobis(2-aminopropane)-dihydrochloride, 2,2-azobis[2-(imidazolin-2-yl)propane]-dihydrochloride, η-5-2-4-(cyclopentadienyl)-(1,2,3,4,5,6, η)-(methylethyl)-benzene]iron (II) hexafluorophosphate and bis(cyclopentadienyl)bis[2,6-difluoro-3-(1H-pyl-1-yl) phenyl]titanium, all of which are known compounds. They may be used either singly or in combination.

The photopolymerization initiator, when used, is incorporated at 0.001 to 10 parts by weight per 100 parts by weight of the polymerizable compound(s) [the acrylic ester compound represented by formula (1) and one or more known polymerizable compounds used, as required], preferably 0.01 to 5 parts, more preferably 0.01 to 3 parts, still more preferably 0.01 to 1 part.

The thermal polymerization initiators useful for the present invention include: peroxides, e.g., benzoyl peroxide, p-chlorobenzoyl peroxide, diisopropyl peroxycarbonate, di-2-ethylhexyl peroxycarbonate and tert-butylperoxypivalate; and azo compounds, e.g., azobisisobutylonitrile.

The thermal polymerization initiator, when used, is incorporated at 0.001 to 10 parts by weight per 100 parts by weight of the polymerizable compound(s) [the acrylic ester compound represented by formula (1) and one or more known polymerizable compounds used, as required], preferably 0.01 to 5 parts, more preferably 0.01 to 3 parts, still more preferably 0.01 to 1 part.

The known polymerizable compounds which can be used together with the acrylic ester compound represented by formula (1) for the polymerizable composition of the present invention include a variety of known polymerizable monomers, such as mono- and poly-valent (meth)acrylates, e.g., methyl (meth)acrylate, butyl (meth)acrylate, 2-ethylhexyl (meth)acrylate, ethylcarbitol (meth)acrylate, lauryl (meth)acrylate, tetracyclododecyl (meth)acrylate, phenoxyethyl (meth)acrylate, nonylphenoxyethyl (meth)acrylate, dicyclopentenyl (meth)acrylate, isobornyl (meth)acrylate, N-n-butyl-O-(meth)acryloyloxyethylcarbamate, acryloyl morpholine, trifluoroethyl (meth)acrylate, tribromobenzyl (meth)acrylate, perfluorooctylethyl (meth)acrylate, ethylene glycol di(meth)acrylate, propylene glycol di(meth)acrylate, neopentyl glycol di(meth)acrylate, 1,6-hexanediol di(meth)acrylate, triethylene glycol di(meth)acrylate, tripropylene glycol di(meth)acrylate, polyethylene glycol di(meth)acrylate, polypropylene glycol di(meth)acrylate, 2,2-bis(4-acryloyloxyphenyl)-propane, 2,2-bis(4-methacryloyloxyphenyl)propane, bis(4-acryloyloxyphenyl) methane, bis(4-methacryloyloxy-phenyl)methane, 4,4'-bis(2-acryloyloxy)phenyl sulfide, 4,4'-bis(2-methacryloyloxy) phenyl sulfide, 2,2-bis(4-acryloyloxyethoxyphenyl)propane, 2,2-bis(4-methacryloyl-oxyethoxyphenyl)propane, 2,2-bis [4-(2-acryloyloxy-propoxy)phenyl]propane, 2,2-bis[4-(2-methacryloyloxy-propoxy)phenyl]propane, bis(4-acryloyloxyethoxyphenyl)methane, bis(4-methacryloyloxyethoxyphenyl)methane, bis[4-(2-acryloyloxypropoxy)phenyl]methane, bis[4-(2-methacryloyloxypropoxy)phenyl]methane, 4,4'-bis(2-acryloyloxyethoxy)phenyl sulfide, 4,4'-bis(2-methacryloyloxyethoxy)phenyl sulfide, 4,4'-bis(2-acryloyloxypropoxy)phenyl sulfide, 4,4'-bis(2-methacryloyloxypropoxy)phenyl sulfide, 4,4'-bis(2-acryloyloxyethoxy)phenyl sulfone, 4,4'-bis(2-methacryloyloxyethoxy)phenyl sulfone, 4,4'-bis(2-acryloyloxypropoxy)phenyl sulfone, 4,4'-bis(2-methacryloyloxypropoxy)phenyl sulfone, di(meth)acrylate of ethylene or propylene oxide adduct of 2,2'-bis(4-hydroxyphenyl)propane, di(meth)acrylate of ethylene or propylene oxide adduct of bis(4-hydroxy-phenyl)methane, di(meth)acrylate of ethylene or propylene oxide adduct of 4,4'-dihydroxyphenyl sulfide, trimethylolpropane tri(meth)acrylate, dipentaerythritol pentaacrylate, pentaerythritol triacrylate, pentaerythritol tetraacrylate, ditrimethylol tetraacrylate, dipentaerythritol hexaacrylate, 2-(meth) acryloyloxyethyl trisisocyanurate and (meth)acryloxypropyl tris(methoxy)silane; epoxy (meth)acrylates obtained by acting a (meth)acrylic acid compound on a known mono- or di-valent epoxy compound such as phenol glycidyl ether, ethylene glycol diglycidyl ether, propylene glycol diglycidyl ether, resorcin diglycidyl ether, hydroquinone diglycidyl ether, bis(4-hydroxyphenyl)methane (commonly referred to as bisphenol F) diglycidyl ether, 2,2-bis(4-hydroxyphenyl)-propane (commonly referred to as bisphenol A) diglycidyl ether, 4,4'-bishydroxyphenyl sulfide diglycidyl ether, 4,4'-bishydroxyphenyl sulfide (commonly referred to as bisphenol S) diglycidyl ether, 3,3',5,5'-tetramethyl-4,4'-biphenol diglycidyl ether and tris(2,3-epoxypropyl)-isocyanurate; epoxy (meth)acrylates obtained by acting a (meth)acrylic acid compound on a known epoxy resin such as phenol novolac type, cresol novolac type, phenol zyrock type or bisphenol type epoxy resin; vinyl compounds, e.g., vinyl benzene, divinyl benzene, trivinyl benzene, isopropenyl benzene, diisopropenyl benzene, triisopropenyl benzene, N-vinyl pyrrolidone and N-vinyl caprolactam; compounds containing an allyl group, e.g., ethylene glycol diallyl carbonate, triallyl trimellitate ester and triallyl isocyanurate;

and a variety of known polymerizable olifomers, e.g., urethane (meth)acrylates, epoxy (meth)acrylates, polyester (meth)acrylates and polyether (meth)acrylates.

Quantity of those is not limited. However, it is normally incorporated at 300 parts by weight or less per 100 parts by weight of the acrylic ester compound of the present invention, preferably 200,parts or less, more preferably 100 parts or less, to secure the effect of the present invention.

The polymerizable composition of the present invention is produced by mixing and dissolving the acrylic ester compound of the present invention represented by formula (1), and, as required, one or more of the above-described known polymerizable compounds and the above-described polymerization initiator. The polymerizable composition may be filtered to remove impurities and/or foreign matter and, moreover, sufficiently defoamed under a vacuum, as required, before being polymerized and cured.

The starting mixture for the polymerizable composition may be incorporated one or more of a variety of known additives, as required, within limits not harmful to the effect of the present invention. These additives useful for the present invention include an internal releasing agent, a light stabilizer, an ultraviolet ray absorber, an antioxidant, a colorant/pigment (e.g., cyanine green and cyanine blue), a dye, a flow-adjusting agent, and an inorganic filler (e.g., talc, silica, alumina, barium sulfate or magnesium oxide).

The cured product of the present invention and optical component made of the cured product are obtained by polymerizing and curing the polymerizable composition. They have been suitably produced by a variety of known methods, typically by heat- or light-initiated radical polymerization of the polymerizable composition put in a mold.

One of the typical molds for the polymerization is composed of two mirror-polished molds having a gasket (e.g., of polyethylene, ethylene/vinyl acetate copolymer or polyvinyl chloride) therebetween. A set of two molds is a combination of glass and glass plates, glass and plastic plates or glass and metallic plates, among others. They may be adhered to each other via an adhesive tape (e.g., of polyester), instead of via a gasket of the above-described soft, thermoplastic resin (e.g., polyethylene, ethylene/vinyl acetate copolymer or polyvinyl chloride). The mold may be treated by a conventional procedure, e.g., releasing.

The radical polymerization may be effected by the aid of heat (thermal polymerization), light such as ultraviolet ray or visible ray (photopolymerization), activated energy ray such as gamma ray, or their combination.

When the photopolymerization is adopted, the cured product released out of the mold or the optical component thereof may be annealed to remove the internal stress or strain.

Of these methods, the photopolymerization is preferable in view of productivity for production of the optical component of the present invention, because it can cure the composition in several seconds to several minutes. This compared with several hours to more than 10 hours needed by the thermal polymerization.

The temperature for the heat polymerization is not limited, because it depends on polymerization conditions, e.g., type of polymerization initiator adopted. However, it is normally in a range from 25 to 200° C., preferably 50 to 170° C.

The optical lens can be molded by casting in which the polymerizable composition is polymerized in a mold by the aid of light and/or heat, as disclosed by, e.g., Japanese Patent Laid-open Publication Nos. 60-135901, 10-67736 and 10-130250. More specifically, the polymerizable composition prepared in the above-described manner to contain the acrylic ester compound of the present invention represented by formula (1), is put in a mold where it is suitably polymerized normally with the aid of light, after being defoamed as required by an adequate procedure. When the thermal polymerization is adopted, it can be suitably carried out by heating the polymerizable composition slowly from low to high temperature.

The optical lens produced may be annealed as required, after being cured. It may be further treated physically or chemically by a known procedure, e.g., surface polishing, antistatic treatment, hard coating, reflection free coating, dye treatment or light modulation (for example, photochromic lens treatment), as required, for various purposes, e.g., preventing light reflection, imparting hardness, improving wear resistance, imparting anti-fogging property or imparting fashinability.

For production of a substrate for information recording medium, e.g., optical disk, the polymerizable composition prepared in the above-described manner to contain the acrylic ester compound of the present invention represented by formula (1), is injected into a cavity for disk substrates, where it is polymerized by a known procedure, e.g., radical polymerization followed, as required, by heating for post-treatment (disclosed by, e.g., Japanese Patent Laid-open Publication Nos. 58-130450, 58-137150 and 62-280008), photopolymerization in a mold with glass plates on both sides (disclosed by, e.g., Japanese Patent Laid-open Publication No. 60-202557), or thermal polymerization of liquid resin in a vacuum mold or under pressure after it is injected into a mold (disclosed by, e.g., Japanese Patent Laid-open Publication No. 60-203414).

The cured product of the photopolymerized composition of the present invention and the optical component thereof can be produced in a shorter time of several minutes to several hours for polymerization (curing) and molding than the conventional thermosetting optical resin represented by polydiethylene glycol diallyl carbonate or polythiourethane. Higher productivity is one of the characteristics of the present invention. The cured product and the optical component thereof of the present invention are also characterized by high transparency and higher refractive index than that of the conventional thermosetting resin, while involving practically no problems in mechanical and thermal characteristics. The optical component of the present invention can find wide applications, e.g., various types of plastic optical lenses represented by vision-correcting spectacles lenses and pickup lenses, optical disk substrates for information recording media, plastic substrates for liquid crystal cells, and various transparent coating materials, e.g., anti-reflective coating.

The cured product or optical component of the present invention can be produced efficiently in a short time by photopolymerization or the like; is high in refractive index and good in optical characteristics (e.g., transparency and Abbe number), thermal characteristics (e.g., thermal deformation temperature) and mechanical characteristics (e.g., impact resistance; and hence is useful for various purposes, e.g., various types of plastic lenses represented by vision-correcting spectacles lenses, transparent substrate materials for optical information recording media and liquid crystal cells, various transparent coating materials, e.g., those for anti-reflective coating, various transparent sealants, e.g., those for light-emitting diodes (LEDs), and dental materials.

The present invention will be described in more detail by EXAMPLES, which by no means limit the present invention.

◇ Synthesis of the Sulfur-Containing Compound of the Present Invention Represented by Formula (2-a)

EXAMPLE 1

[Synthesis of Example Compound No. (2-a-1); Sulfur-containing compound represented by formula (2) in which "a" is 1, $R_1$ is a directly bonded single bond, "k" and "l" are each 1, and $X_1$ and $X_2$ are each an oxygen atom]

A starting mixture of 50.4 g (0.406 mol) of 2,3-dimercapto-1-propanol and 26.2 g of a 40% aqueous solution of glyoxal (0.180 mol as glyoxal) dissolved in 55 g of dioxane was prepared, to which 0.36 g of 98% sulfuric acid (3.6 mmols as $H_2SO_4$) was added dropwise under water cooling at 25° C. The resultant mixture was stirred under heating at 60° C. for 8 hours. After completion of the reaction, the reaction mixture was heated at 50° C. under a vacuum for concentration while distilling off dioxane and water, to obtain a yellowish liquid as a crude product. The crude product thus prepared was further purified by silica gel column chromatography (developing solvent: toluene/ethyl acetate: 15/85), to obtain 41.3 g (0.153 mol) of the dihydroxy compound represented by the following formula, which was a colorless, transparent liquid, as Example Compound No. (2-a-1). Its yield was 85% on glyoxal as the starting compound.

270 MHz $^1$H-NMR $\delta$ (CDCl$_3$); 3.10 to 3.70 (m, 8H), 3.72 to 3.90 (m, 2H), 4.30 to 4.60 (m, 2H), 4.80 to 4.90 (m, 2H) EI-MS: 270(M)

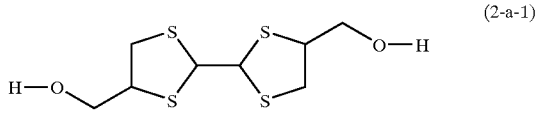

(2-a-1)

EXAMPLE 2

[Synthesis of Example Compound No. (2-a-2); Sulfur-containing compound represented by formula (2) in which "a" is 1, $R_1$ is a methylene group, "k" and "l" are each 1, and $X_1$ and $X_2$ are each an oxygen atom]

A glass-made reactor (inside volume: 2 L) equipped with a condenser, thermometer, gas-blowing tube and stirrer was charged with 500 g of 2-methoxy ethanol, into which 36.5 g (1.00 mol) of hydrogen chloride gas was blown at 15° C. in 1 hour to be dissolved therein, and then 82.0 g (0.50 mol) of malondialdehyde bisdimethylacetal(1,1,3,3-tetramethoxypropane) was added at 10° C. Then, 137.0 g (1.10 mols) of 2,3-dimercapto-1-propanol was added immediately to the above mixture at the same temperature, and the resultant mixture was stirred at 25° C. for 12 hours. After the starting compound was confirmed to disappear by gas chromatography, the reaction mixture was added, with stirring, to 1000 g of water in 30 minutes. The resultant mixture was subjected to extraction with chloroform and washing with water, and separation to obtain an organic phase. Chloroform was distilled at 45° C. under a vacuum to obtain a singly yellowish, transparent liquid crude product. The crude product thus prepared was purified by silica gel column chromatography (developing solvent: using mixed solvent of toluene/ethyl acetate: 60/40), to obtain 92.4 g (0.325 mol) of the dihydroxy compound represented by the following formula, which was a lightly yellowish crystal, as Example Compound No. (2-a-2). Its yield was 65% on malondialdehyde bisdimethylacetal as the starting compound.

270 MHz $^1$H-NMR $\delta$ (CDCl$_3$); 2.18 to 2.33 (m, 2H), 3.15 to 3.38, (m, 4H), 3.42 to 3.68 (m, 4H), 3.72 to 3.88 (m, 2H), 4.47 (dq, 2H), 4.72 to 4.78 (m, 2H) EI-MS: 284(M)

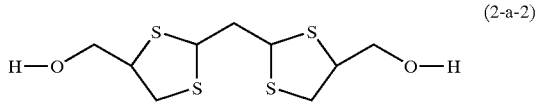

(2-a-2)

EXAMPLE 3

[Synthesis of Example Compound No. (2-a-3); Sulfur-containing compound represented by formula (2) in which "a" is 1, $R_1$ is a dimethylene group, "k" and "l" are each 1, and $X_1$ and $X_2$ are each an oxygen atom]

The dihydroxy compound represented by the following formula was prepared as Example Compound No. (2-a-3) in the same manner as in EXAMPLE 2, except that malondialdehyde bisdimethylacetal (1,1,3,3-tetramethoxypropane) was replaced by succinaldehyde bisdimethylacetal (1,1,4,4-tetramethylbutane).

EI-MS: 298(M) 270 MHz $^1$H-NMR $\delta$ (CDCl$_3$); 1.93 to 2.10 (m, 4H), 2.54 (br, 2H), 3.23 to 3.32 (m, 4H), 3.52 to 3.97 (m, 6H), 4.43 to 4.53 (m, 2H)

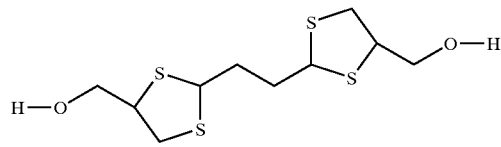

(2-a-3)

EXAMPLE 4

[Synthesis of Example Compound No. (2-a-11); Sulfur-containing compound represented by formula (2) in which "a" is 1, $R_1$ is a 1,4-phenylene group, "k" and "l" are each 1, and $X_1$ and $X_2$ are each an oxygen atom]

A starting mixture of 50.2 g (0.404 mol) of 2,3-dimercapto-1-propanol and 26.8 g (0.200 mol) of terephthalaldehyde dissolved in 200 g of dioxane was prepared, to which 0.20 g of 98% sulfuric acid (0.002 mol as $H_2SO_4$) was added dropwise under water cooling at 25° C. The resultant mixture was stirred under heating at 60° C. for 4 hours. It was observed that a solid precipitated as the reaction proceeded. After the completion of the reaction, 40 g of hexane was added dropwise to the reaction mixture at 60° C., and the resultant mixture was left to cool to room temperature, to collect the precipitated solid by filtration. The collected solids were washed with 50 g of mixed solvent of dioxane/hexane (1:1 by weight), and the resultant yellowish crystals as the crude product were purified by recrystallization from mixed solvent of dioxane/hexane (2:1 by weight), to obtain 55.5 g (yield: 80%) of the dihydroxy compound represented by the following formula of Example Compound No. (2-a-11) as lightly yellowish crystals.

270 MHz $^1$H-NMR $\delta$ (CDCl$_3$); 3.25 to 4.15 (m, 10H), 3.30 to 4.25 (br, 2H), 5.72 (s, 2H), 7.48,(d, 4H) EI-MS: 346(M)

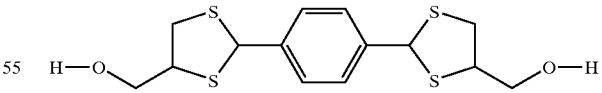

(2-a-11)

EXAMPLE 5

[Synthesis of Example Compound No. (2-a-12); Sulfur-containing compound represented by formula (2) in which "a" is 1, $R_1$ is a 1,3-phenylene group, "k" and "l" are each 1, and $X_1$ and $X_2$ are each an oxygen atom]

The dihydroxy compound represented by the following formula was prepared as Example Compound No. (2-a-12) in the same manner as in EXAMPLE 4, except that terephthalaldehyde was replaced by isophthalaldehyde.

270 MHz $^1$H-NMR δ (CDCl$_3$); 3.25 to 4.20 (m, 12H), 3.30 to 4.25 (br, 2H), 5.65 (d, 2H), 7.15 to 7.48 (m, 4H) EI-MS: 346(M)

(2-a-12)

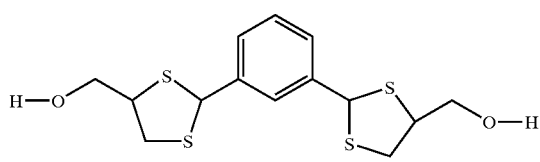

EXAMPLE 6
[Synthesis of Example Compound No. (2-a-21); Sulfur-containing compound represented by formula (2) in which "a" is 1, R$_1$ is a directly bonded single bond, "k" and "l" are each 1, and X$_1$ and X$_2$ are each a sulfur atom]

A glass-made reactor (inside volume: 1L) equipped with a stirrer and condenser was charged with 54.8 g (0.72 mol) of thiourea and 194.8 g of 18% hydrochloric acid (0.96 mol as hydrogen chloride), which were mixed with each other with stirring. Then, 64.8 g (0.24 mol) of the dihydroxy compound prepared in EXAMPLE 1 [Example Compound No. (2-a-1)] was added dropwise to the above mixture at 80° C. in 1 hour, and the reaction was allowed to proceed at 100° C. for 3 hours to produce a thiuronium salt. After the reaction solution was confirmed to contain no hydroxy compound as the starting compound by high performance liquid chromatography, 307.2 g of a 25% aqueous solution of sodium hydroxide (1.92 mols as sodium hydroxide) was added to the solution at 50° C. in 30 minutes, and then the thiuronium salt was hydrolyzed at 100° C. for 1 hour. The resultant solution was cooled to 25° C., neutralized with 243.2 g of 18% hydrochloric acid (1.20 mols as hydrogen chloride), subjected to extraction with 800 g of toluene and washed with water, to separate an organic phase. Toluene was distilled off at 40° C. under a vacuum to obtain a crude product. The crude product was purified by silica gel column chromatography, to obtain 64.4 g (yield: 85%) of the dithiol compound represented by the following formula, which was the form of lightly yellowish crystals, as Example Compound No. (2-a-21).

Purity: above 99% (determined by the area method of high performance liquid chromatography) 270 MHz $^1$H-NMR δ (CDCl$_3$); 1.55 to 1.78 (m, 2H), 2.75 to 2.96 (dt, 4H), 3.22 to 3.45 (m, 4H), 3.78 to 3.92 (m, 2H), 4.65 to 4.80 (m, 2H) EI-MS: 302(M)

(2-a-21)

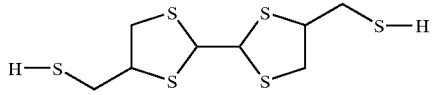

EXAMPLE 7
[Synthesis of Example Compound No. (2-a-22); Sulfur-containing compound represented by formula (2) in which "a" is 1, R$_1$ is a methylene group, "k" and "l" are each 1, and X$_1$ and X$_2$ are each a sulfur atom]

The dithiol compound represented by the following formula (2-a-22) was prepared in the same manner as in EXAMPLE 6, except that the dihydroxy compound prepared in EXAMPLE 1 [Example Compound No. (2-a-1)] was replaced by Example Compound No. (2-a-2) prepared in EXAMPLE 2.

Purity: >99% (determined by the area method of high performance liquid chromatography) 270 MHz $^1$H-NMR δ (CDCl$_3$); 1.66 (t, 2H), 2.20 to 2.41 (m, 2H), 2.80 (dd, 4H), 3.22 to 3.37 (m, 4H), 3.78 to 3.88 (m, 2H), 4.46 to 4.60 (m, 2H) EI-MS: 316(M)

(2-a-22)

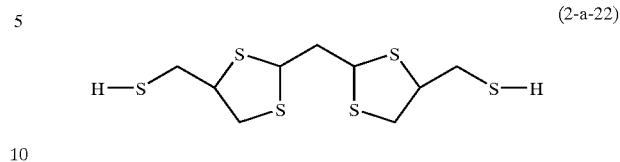

EXAMPLE 8
[Synthesis of Example Compound No. (2-a-23); Sulfur-containing compound represented by formula (2) in which "a" is 1, R$_1$ is a dimethylene group, "k" and "l" are each 1, and X$_1$ and X$_2$ are each a sulfur atom]

The dithiol compound represented by the following formula (2-a-23) was prepared in the same manner as in EXAMPLE 6, except that the dihydroxy compound prepared in EXAMPLE 1 [Example Compound No. (2-a-1)] was replaced by Example Compound No. (2-a-3) prepared in EXAMPLE 3.

Purity: >99% (determined by the area method of high performance liquid chromatography) 270 MHz $^1$H-NMR δ (CDCl$_3$); 1.60 to 1.72 (q, 2H), 1.88 to 2.05 (m, 4H), 2.74 to 2.88 (m, 4H), 3.28 to 3.35 (m, 2H), 3.72 to 3.88 (m, 2H), 4.42 to 4.55 (m, 2H) EI-MS: 330(M)

(2-a-23)

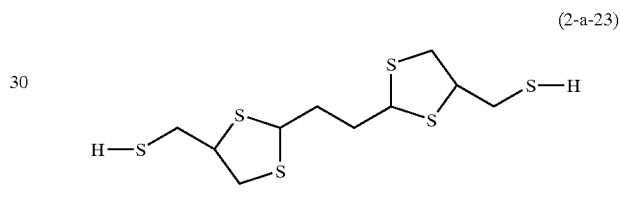

EXAMPLE 9
[Synthesis of Example Compound No. (2-a-31); Sulfur-containing compound represented by formula (2) in which "a" is 1, R$_1$ is a 1,4-phenylene group, "k" and "l" are each 1, and X$_1$ and X$_2$ are each a sulfur atom]

A glass-made reactor (inside volume: 1 L) equipped with a stirrer and condenser was charged with 45.6 g (0.60 mol) of thiourea and 162.4 g of 18% hydrochloric acid (0.80 mol as hydrogen chloride), which were mixed with each other with stirring. Then, 69.2 g (0.20 mol) of the dihydroxy compound prepared in EXAMPLE 4 [Example Compound No. (2-a-11)] was added dropwise to the above mixture at 60° C. in 35 minutes, and the reaction was allowed to proceed at 100° C. for 4 hours to produce a thiuronium salt. After the reaction solution was confirmed to contain no hydroxy compound as the starting compound by high performance liquid chromatography, 256 g of a 25% aqueous solution of sodium hydroxide (1.60 mols as sodium hydroxide) was added to the solution at 50° C. in 30 minutes, and then the thiuronium salt was hydrolyzed at 100° C. for 1 hour. The resultant solution was cooled to 25° C., and neutralized with 200.4 g of 18% hydrochloric acid (1.00 mol as hydrogen chloride). The oil layer produced was extracted with 600 g of toluene and washed with water, and the organic phase separated from the solution was taken out. Toluene was distilled off at 40° C. under a vacuum to obtain a crude product. The crude product was purified by silica gel column chromatography, to obtain 64.4 g (yield: 85%) of the dithiol compound represented by the following formula, which was a form of lightly yellowish crystals, as Example Compound No. (2-a31).

Purity: 99% (determined by the area method of high performance liquid chromatography) 270 MHz $^1$H-NMR δ

(CDCl$_3$); 1.70 (t, 2H), 2.83 to 3.15 (m, 4H), 3.35 to 3.60 (m, 4H), 3.97 (dm, 2H), 5.63 (d, 2H), 7.48 (d, 4H) EI-MS: 378(M)

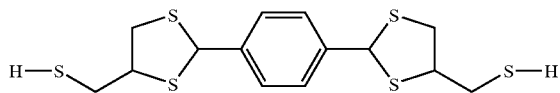
(2-a-31)

EXAMPLE 10

[Synthesis of Example Compound No. (2-a-32); Sulfur-containing compound represented by formula (2) in which "a" is 1, R$_1$ is a 1,3-phenylene group, "k" and "l" are each 1, and X$_1$ and X$_2$ are each a sulfur atom]

The dithiol compound represented by the following formula (2-a-32) was prepared in the same manner as in EXAMPLE 9, except that the dihydroxy compound prepared in EXAMPLE 4 [Example Compound No. (2-a-11)] was replaced by Example Compound No. (2-a-12) prepared in EXAMPLE 5.

Purity: above 99% (determined by the area method of high performance liquid chromatography) 270 MHz $^1$H-NMR δ (CDCl$_3$); 1.70 (t, 2H), 2.80 to 3.12 (m, 4H), 3.33 to 3.57 (m, 4H), 3.96 (dm, 2H), 5.63 (d, 2H), 7.12 to 7.46 (m, 4H) EI-MS: 378(M)

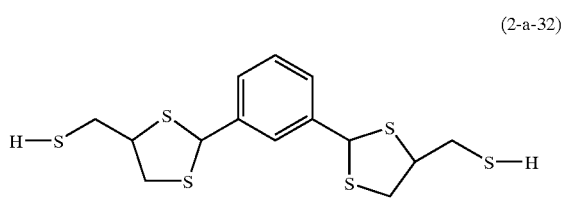
(2-a-32)

◇ Synthesis of the Acrylic Ester Compound Represented by Formula (1-a)

EXAMPLE 11

[Synthesis of Example Compound No. 1-a-21; Acrylic ester compound represented by formula (1) in which "a" is 1, R$_1$ is a directly bonded single bond, R$_2$ and R$_3$ are each a hydrogen atom, "k" and "l" are each 1, and X$_1$ and X$_2$ are each a sulfur atom]

First, 80.0 g (0.63 mol) of 3-chloropropionic acid chloride was added dropwise to a solution of 65.0 g (0.21 mol) of the dithiol compound (2-a-21), prepared in EXAMPLE 6, dissolved in 320 g of toluene at 100° C. in 30 minutes. They were allowed to react at 110° C. for 6 hours, with stirring. The reaction mixture was cooled to 25° C., to which 689 g of a 5% aqueous solution of sodium hydrogen carbonate (0.42 mol as sodium hydrogen carbonate) was added. The resultant mixture was stirred for 30 minutes, and treated with 800 g of toluene for extraction. The extract organic phase (toluene solution) was washed with 500 g of pure water 3 times, and the separated organic phase was taken out after the aqueous phase was confirmed to turn neutral. It was distilled under a vacuum to be concentrated while removing toluene, to obtain 80.0 g of a lightly yellowish, transparent liquid as a crude product. The crude product thus prepared was purified by silica gel column chromatography (developing solvent: toluene/chloroform: 90/10), to obtain 82.2 g (0.17 mol) of 2,2'-bi[4-(3-chloropropionyl-thiomethyl)-1,3-dithiolan, which was a lightly yellowish, transparent liquid.

Next, 52.0 g (0.51 mol) of triethylamine was added dropwise to a solution of 82.2 g (0.17 mol) of 2,2'-bi[4-(3-chloropropionylthiomethyl)-1,3-dithiolan prepared above and dissolved in 340 g of acetone at. 5° C. in 1 hour. They were allowed to react at the same temperature for 3 hours, with stirring, to which 800 g of water was added. The resultant mixture was treated with 800 g of toluene to extract the reaction product. The extract organic phase (toluene solution) was washed with pure water until the aqueous phase turned neutral. Then, the separated organic phase was taken out, incorporated with 0.15 g of 4-methoxyphenol as a polymerization inhibitor, and distilled under a vacuum to be concentrated while removing toluene, to obtain a lightly yellowish, transparent liquid as a crude product. The crude product thus prepared was purified by silica gel column chromatography (developing solvent: toluene/chloroform: 90/10), and again incorporated with 0.15 g of 4-methoxyphenol as a polymerization inhibitor, to obtain 58.0 g (0.14 mol) of 2,2'-bi(4-acryloylthiomethyl-1,3-dithiolan) represented by the following formula (1-a-21). It was 99% pure, as determined by the area method of high performance liquid chromatography, and produced in a yield of 67% on 2,2'-bi(4-mercaptomethyl-1,3-dithiolan).

The compound as a liquid at 20° C. had a refractive index (nd) of 1.653.

270 MHz $^1$H-NMR δ (CDCl$_3$); 3.10 to 3.42 (m, 8H), 3.88 to 4.03 (m, 2H), 4.72 (dt, 2H), 5.70 to 5.79 (m, 2H), 6.38 (d, 4H) EI-MS: 410(M)

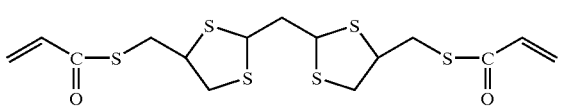
(1-a-21)

EXAMPLE 12

[Synthesis of Example Compound No. 1-a-22; Acrylic ester compound represented by formula (1) in which "a" is 1, R$_1$ is a methylene group, R$_2$ and R$_3$ are each a hydrogen atom, "k" and "l" are each 1, and X$_1$ and X$_2$ are each a sulfur atom]

Bis(4-acryloylthiomethyl-1,3-dithiolan-2-yl)methane as a colorless, transparent liquid represented by the following formula (1-a-22) was prepared in the same manner as in EXAMPLE 11, except that the dithiol compound prepared in EXAMPLE 6 [Example Compound No. (2-a-21)] was replaced by the dithiol compound prepared in EXAMPLE 7 [Example Compound No. (2-a-22)]. It was above 99% pure, as determined by the area method of high performance liquid chromatography, and produced in a yield of 72% on bis(4-mercaptomethyl-1,3-dithiolan-2-yl)methane.

The compound as a liquid at 20° C. had a refractive index (nd) of 1.640.

270 MHz $^1$H-NMR δ (CDCl$_3$); 2.20 to 2.41 (m, 2H), 3.05 to 3.35 (m, 8H), 3.80 to 3.95 (m, 2H), 4.50 to 4.65 (m, 2H), 5.70 (dd, 2H), 6.35 (dd, 4H) EI-MS: 424(M)

(1-a-22)

EXAMPLE 13

[Synthesis of Example Compound No. (1-a-23); Acrylic ester compound represented by formula (1) in which "a" is 1, R$_1$ is a dimethylene group, R$_2$ and R$_3$ are each a hydrogen atom, "k" and "l" are each 1, and X$_1$ and X$_2$ are each a sulfur atom]

Bis(4-acryloylthiomethyl-1,3-dithiolan-2-yl)ethane as a colorless, transparent liquid represented by the following formula (1-a-23) was prepared in the same manner as in EXAMPLE 11, except that the dithiol compound prepared in EXAMPLE 6 [Example Compound No. (2-a-21)] was replaced by the dithiol compound prepared in EXAMPLE 8 [Example Compound No. (2-a-23)]. It was above 99% pure, as determined by the area method of high performance liquid chromatography, and produced in a yield of 75% on bis(4-mercaptomethyl-1,3-dithiolan-2-yl)ethane.

The compound as a liquid at 20° C. had a refractive index (nd) of 1.634.

270 MHz $^1$H-NMR δ (CDCl$_3$); 1.85 to 2.05 (m, 4H), 3.08 to 3.32 (m, 8H), 3.80 to 3.95 (m, 2H), 4.45 to 4.55 (m, 2H), 5.71 (dd, 2H), 6.32 (dd, 4H) EI-MS: 438(M)

(1-a-23)

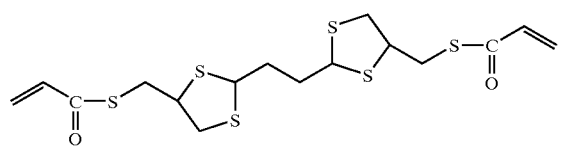

EXAMPLE 14

[Synthesis of Example Compound No. (1-a-31); Acrylic ester compound represented by formula (1) in which "a" is 1, $R_1$ is a 1,4-phenylene group, $R_2$ and $R_3$ are each a hydrogen atom, "k" and "l" are each 1, and $X_1$ and $X_2$ are each a sulfur atom]

In EXAMPLE 11, 1,4-bis(4-acryloylthiomethyl-1,3-dithiolan-2-yl)benzene as a colorless, transparent liquid represented by the following formula (1-a-31) was prepared in the same manner as in EXAMPLE 11, except that the dithiol compound prepared in EXAMPLE 6 [Example Compound No. (2-a-21)] was replaced by the dithiol compound prepared in EXAMPLE 9 [Example Compound No. (2a-31)]. It was above 99% pure, as determined by the area method of high performance liquid chromatography, and produced in a yield of 80% on 1,4-bis(4-mercaptomethyl-1,3-dithiolan-2-yl)benzene.

The compound as a liquid at 20° C. had a refractive index (nd) of 1.661.

270 MHz $^1$H-NMR δ (CDCl$_3$); 3.20 to 3.55 (m, 8H), 4.07 (dm, 2H), 5.63 to 5.78 (m, 4H), 6.38 (d, 4H), 7.48 (dd, 4H) EI-MS: 486(M)

(1-a-31)

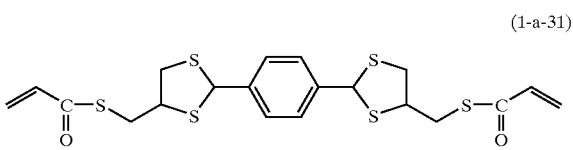

EXAMPLE 15

[Synthesis of Example Compound No. (1-a-32); Acrylic ester compound represented by formula (1) in which "a" is 1, $R_1$ is a 1,3-phenylene group, $R_2$ and $R_3$ are each a hydrogen atom, "k" and "l" are each 1, and $X_1$ and $X_2$ are each a sulfur atom]

In EXAMPLE 11, 1,3-bis(4-acryloylthiomethyl-1,3-dithiolan-2-yl)benzene as a colorless, transparent liquid represented by the following formula (1-a-32) was prepared in the same manner as in EXAMPLE 11, except that the dithiol compound prepared in EXAMPLE 6 [Example Compound No. (2-a-21)] was replaced by the dithiol compound prepared in EXAMPLE 10 [Example Compound No. (2a-32)].

It was above 99% pure, as determined by the area method of high performance liquid chromatography, and produced in a yield of 80% on 1,3-bis(4-mercaptomethyl-1,3-dithiolan-2-yl)benzene.

The compound as a liquid at 20° C. had a refractive index (nd) of 1.660.

270 MHz $^1$H-NMR δ (CDCl$_3$); 3.20 to 3.58 (m, 8H), 4.10 (dm, 2H), 5.63 to 5.78 (m, 4H), 6.40 (d, 4H), 7.18 to 7.52 (m, 4H) EI-MS: 486(M)

(1-a-32)

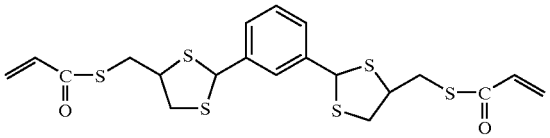

◊ Production of the Polymerizable Composition Containing the Acrylic Ester Compound Represented by Formula (1-a), and of the Cured Product by Curing the Same Composition The cured product prepared in each of EXAMPLES or COMPRATIVE EXAMPLES described below, or the optical component (lens) of the same product was evaluated by the following procedures:

Appearances: Color and transparency were confirmed by visual observation.

Specific gravity: Determined by "DENSIMETER D-1" manufactured by Toyo Seiki Seisaku-Sho, Ltd.

Refractive index and Abbe number: Determined at 20° C. by a Pulfrich refractometer.

Heat resistance: Measured by the needle penetration method using the thermomechanical analysis (TMA), to determine glass transition temperature (Tg) from the displacement point from the TMA curve of the cured product.

Impact resistance: An iron ball (16.2 g) was dropped from a height of 127 cm onto the center of a minus lens, 1.5 mm thick at the center, to observe whether it was cracked or not.

EXAMPLE 16

[Production of the polymerizable composition containing the acrylic ester compound of the present invention, and of the cured product by curing the same composition]

First, 60 mg of 2-hydroxy-2-methyl-1-phenylpropan-1-one (Ciba Geigy's Darocur-1173) as a photopolymerization initiator was added to, well mixed with and dissolved in 30 g of the acrylic ester compound prepared in EXAMPLE 11 (Example Compound No. 1-a-21). Then, the liquid thus prepared was sufficiently degassed under a vacuum, and put in a mold composed of glass molds and a gasket, where it was irradiated with ultraviolet ray emitted from a metal halide lamp (80 W/cm) for 180 seconds to carry out polymerization. After the completion of the polymerization, it was slowly cooled, and the cured product was separated out from the mold and heat-treated at 80° C. for 2 hours for annealing. It was colorless and transparent, and showed no optical strain.

The cured product had a refractive index (nd) of 1.681, Abbe number (vd) of 34.6 and specific gravity of 1.40, and was good in heat resistance having a glass transition temperature (Tg) of 123° C.

EXAMPLE 17

The polymerizable composition and cured (polymerized) product thereof were prepared in the same manner as in EXAMPLE 16, except that the acrylic ester compound prepared in EXAMPLE 11 (Example Compound No. 1-a-21) was replaced by the one prepared in EXAMPLE 12 (Example Compound No. 1-a-22).

The cured product had a refractive index (nd) of 1.673 and Abbe number (vd) of 34.5, and was good in heat resistance having a glass transition temperature (Tg) of 116° C.

EXAMPLE 18

The polymerizable composition and cured (polymerized) product thereof were prepared in the same manner as in EXAMPLE 16, except that the acrylic ester compound prepared in EXAMPLE 11 (Example Compound No. 1-a-21) was replaced by the one prepared in EXAMPLE 13 (Example Compound No. 1-a-23).

The cured product had a refractive index (nd) of 1.662 and Abbe number (vd) of 35.8 and was good in heat resistance having a glass transition temperature (Tg) of 117° C.

EXAMPLE 19

The polymerizable composition and cured (polymerized) product thereof were prepared in the same manner as in EXAMPLE 16, except that the acrylic ester compound prepared in EXAMPLE 11 (Example Compound No. 1-a-21) was replaced by the one prepared in EXAMPLE 14 (Example Compound No. 1-a-31).

The cured product had a refractive index (nd) of 1.687 and Abbe number (vd) of 30.0 and was good in heat resistance having a glass transition temperature (Tg) of 125° C.

EXAMPLE 20

The polymerizable composition and cured (polymerized) product thereof were prepared in the same manner as in EXAMPLE 16, except that the acrylic ester compound prepared in EXAMPLE 11 (Example Compound No. 1-a-21) was replaced by the one prepared in EXAMPLE 15 (Example Compound No. 1-a-32).

The cured product had a refractive index (nd) of 1.684 and Abbe number (vd) of 30.1 and was good in heat resistance having a glass transition temperature (Tg) of 123° C.

◇ Fabrication of an Optical Component (Lens)

EXAMPLE 21

First, 100 mg of 2-hydroxy-2-methyl-1-phenylpropan-1-one (at a content of 0.1% by weight on the total weight of the polymerizable compounds) was added to, well mixed with and dissolved in a mixture of 90 g of the acrylic ester compound prepared in EXAMPLE 11 (Example Compound No. 1-a-21) and 10 g of epoxy methacrylate of bisphenol A diglycidyl ether. Then, the liquid thus prepared was sufficiently degassed under a vacuum, and put in a mold (adjusted to have a minus lens shape) composed of glass molds and a tape, where it was irradiated with ultraviolet ray emitted from a metal halide lamp (120 W/cm) for 120 seconds. After the completion of the polymerization, the cured product was separated out from the mold, and heat-treated at 100° C. for 1 hour for annealing in an inert oven. It was left to cool to room temperature, to obtain a colorless, transparent minus lens of 80 mm in diameter and 1.5 mm thick at the center.

The lens was colorless and transparent, and showed no optical strain or striae. It had a refractive index (nd) of 1.669 and Abbe number (vd) of 34.0. Moreover, it was good both in heat resistance (thermal deformation temperature) and impact resistance, and showed no problem associated with dye-affinity with a known dispersed dye for dyeing lenses.

EXAMPLE 22

The lens was fabricated in the same manner as in EXAMPLE 21, except that the acrylic ester compound prepared in EXAMPLE 11 (Example Compound No. 1-a-21) was replaced by the one prepared in EXAMPLE 12 (Example Compound No. 1-a-22).

The lens was colorless and transparent, and showed no optical strain or striae. It had a refractive index (nd) of 1.663 and Abbe number (vd) of 35.0. Moreover, it was good both in heat resistance (thermal deformation temperature) and impact resistance, and showed no problem associated with dye-affinity with a known dispersed dye for dyeing lenses.

◇ Synthesis of the Sulfur-Containing Compound of the Present Invention Represented by Formula (2-c)

REFERENCE SYNTHESIS EXAMPLE 1

[Synthesis of the compound represented by formula (10) in Scheme B in which "k" and "m" are each 1]

A 500 mL four-neck flask equipped with a thermometer, condenser and stirrer was charged with 292 g of N,N-dimethylformamide and 102.2 g (0.895 mol) of potassium thioacetate salt and kept at 65 to 70° C., to which 168.8 g (0.856 mol) of bromoacetoaldehyde diethylacetal was added dropwise in 3 hours. The reaction was allowed to proceed at 70° C. for 4 hours with stirring. Then, the reaction solution was cooled to 25° C., to which 950 g of water was added, and the resultant mixture was treated with 500 g of toluene for extraction. The organic phase (toluene solution) was washed with water until it turned neutral. It was distilled under a vacuum to be concentrated while removing solvent, to obtain a lightly yellowish, transparent liquid as a crude product. The crude product was purified by silica gel column chromatography, to obtain 156 g of acetylthioacetoaldehyde diethylacetal, which was a colorless, transparent liquid.

EXAMPLE 23

[Synthesis of Example Compound No. 2-c-5; Compound represented by formula (2) in which "a" is 0, $X_1$ and $X_2$ are an oxygen atom and a sulfur atom, respectively, and "k" and "l" are each 1]

A glass-made reactor equipped with a stirrer, condenser, gas inlet tube and thermometer was charged with 320 g of 2-methoxy ethanol, into which 46.0 g (1.26 mols) of hydrogen chloride gas was blown at 15° C. Then, 61.5 g (0.32 mol) of the acetylthioacetoaldehyde diethylacetal prepared in REFERENCE SYNTHESIS EXAMPLE 1 was added with stirring to the above solution kept at 10° C., to which 49.7 g (0.40 mol) of 2,3-dimercapto-1-propanol was added at the same temperature. The reaction was allowed to proceed at 20° C. for 12 hours with stirring. The reaction mixture was incorporated with 480 g of water, and the resultant mixture was stirred at 30° C. for 30 minutes. It was treated with 720 g of chloroform for extraction, after the acetylthio group of 2-acethylthiomethyl-4-hydroxymethyl-1,3-dithiolan was confirmed to be hydrolyzed by high performance liquid chromatography and the compound disappeared, and the organic phase was washed with water repeatedly until the aqueous phase turned neutral. The organic phase (chloroform solution) was separated out, and distilled under a vacuum to be concentrated while removing chloroform, to obtain a lightly yellowish, transparent liquid as a crude product. The crude product was purified by silica gel column chromatography (developing solvent: toluene/ethyl acetate: 80/20), to obtain 37.0 g of 2-mercaptomethyl-4-hydroxymethyl-1,3-dithiolan, which was a lightly yellowish, transparent liquid in a yield of 63%.

Purity: >99% (determined by the area method of high performance liquid chromatography) 270 MHz $^1$H-NMR δ

(CDCl$_3$); 1.80 to 1.95 (t, 1H), 2.15 to 2.30 (br, 1H), 2.75 to 2.95 (2H), 3.20 to 3.35 (2H), 3.55 to 3.95 (3H), 4.50 to 4.65 (dtm, 1H) EI-MS: 182(M)

◊ Synthesis of the Acrylic Ester Compound of the Present Invention Represented by Formula (1-c)

EXAMPLE 24

[Synthesis of Example Compound No. 1-c-5 shown in Table 1; Compound represented by formula (1) in which "a" is 0, $R_2$ and $R_3$ are each a hydrogen atom, $X_1$ and $X_2$ are an oxygen atom and a sulfur atom, respectively, and "k" and "m" are each 1]

First, 40.0 g (0.31 mol) of 3-chloropropionic acid chloride was added dropwise to a solution of 23.7 g (0.13 mol) of 2-mercaptomethyl-4-hydroxymethyl-1,3-dithiolan, prepared in EXAMPLE 23, dissolved in 78 g of toluene at 100° C. in 15 minutes. They were allowed to react at 110° C. for 6 hours, with stirring. The reaction mixture was cooled to 25° C., to which 437 g of a 5% aqueous solution of sodium hydrogen carbonate (0.26 mol as sodium hydrogen carbonate) was added and then stirred for 30 minutes. The resultant solution was treated with 132 g of toluene for extraction. The extract organic phase (toluene solution) was washed with 260 g of pure water until the aqueous phase turned neutral, and the organic phase was separated out. It was distilled under a vacuum to be concentrated while removing toluene, to obtain 50.0 g of 2-(3-chloropropionylthiomethyl)-4-(3-chloropropionyloxymethyl)-1,3-dithiolan as a crude product, which was a lightly yellowish, transparent liquid.

Next, 40.0 g (0.39 mol) of triethylamine was added dropwise to a solution of 50.0 g (0.13 mol) of 2-(3-chloropropionylthiomethyl)-4-(3-chloropropionyloxymethyl)-1,3-dithiolan prepared above dissolved in 195 g of acetone at 2 to 5° C. in 1 hour. They were allowed to react at the same temperature for 1.5 hours, with stirring, to which 520 g of water was added. The resultant mixture was treated with 520 g of toluene to extract the reaction product. The extract organic phase (toluene solution) was washed with water until the aqueous phase turned neutral. Then, the organic phase was separated out, incorporated with 0.12 g of 4-methoxyphenol as a polymerization inhibitor, and distilled under a vacuum to be concentrated while removing toluene, to obtain a lightly yellowish, transparent liquid as a crude product. The crude product thus prepared was purified by silica gel column chromatography (developing solvent: hexane/ethyl acetate mixture), to obtain 29.0 g of 2-acryloylthiomethyl-4-acryloyloxymethyl-1,3-dithiolan, which was a colorless, transparent liquid, in a yield of 77%.

Purity: >99% (determined by the area method of high performance liquid chromatography) 270 MHz $^1$H-NMR δ (CDCl$_3$); 3.10 to 3.50 (m, 4H), 3.90 to 4.05 (m, 1H), 4.05 to 4.25 (2H), 4.55 to 4.75 (t, 1H), 5.6 to 5.8 (dd, 2H), 6.30 to 6.50 (d, 4H) EI-MS: 290(M)

◊ Production of the Polymerizable Composition Containing the Acrylic Ester Compound of the Present Invention Represented by Formula (1-c), and of the Cured Product or Optical Component by Curing the Same Composition

EXAMPLE 25

First, 60 mg of 2-hydroxy-2-methyl-1-phenylpropan-1-one (Ciba Geigy's Darocur-1173) as a photopolymerization initiator was added to, well mixed with and dissolved in 30 g of the acrylic ester compound prepared in EXAMPLE 24 (Example Compound No. 1-c-5). Then, the liquid thus prepared was sufficiently degassed under a vacuum, and put in a mold composed of glass molds and a gasket, where it was irradiated with ultraviolet ray emitted from a metal halide lamp (80 W/cm) for 360 seconds to proceed polymerization. After the completion of the polymerization, it was slowly cooled, and the cured product was separated out from the mold and heat-treated at 80° C. for 1 hour for annealing. It was colorless and transparent, and showed no optical strain. It had a refractive index (nd) of 1.625, Abbe number (vd) of 41 and specific gravity of 1.40, and was good in heat resistance (thermal deformation temperature), impact resistance and bending strength.

◊ Fabrication of an Optical Component (Lens)

EXAMPLE 26

First, 100 mg of 2-hydroxy-2-methyl-1-phenylpropan-1-one (at a content of 0.1% by weight on the total weight of the polymerizable compounds) was added to, well mixed with and dissolved in a mixture of 90 g of the acrylic ester compound prepared in EXAMPLE 24 (Example Compound No. 1-C-5) and 10 g of epoxy acrylate of bisphenol A diglycidyl ether. Then, the liquid thus prepared was sufficiently degassed under a vacuum, and put in a mold (adjusted to have a minus lens shape) composed of glass molds and a tape, where it was irradiated with ultraviolet ray emitted from a metal halide lamp for 60 seconds. The resultant cured product was heat-treated at 80° C. for 1 hour for annealing. It was left to cool to room temperature, to obtain a colorless, transparent minus lens of 30 mm in diameter and 1.5 mm thick at the center.

The lens was colorless and transparent, and showed no optical strain or striae. It had a refractive index (nd) of 1.618 and Abbe number (vd) of 41. Moreover, it was good in heat resistance (thermal deformation temperature), impact resistance and mechanical strength, and showed good dye-affinity with a known dispersed dye for dyeing lenses.

◊ Synthesis of the Acrylic Ester Compound of the Present Invention Represented by Formula (1-d)

REFERENCE SYNTHESIS EXAMPLE 2

[Synthesis of Example Compound No. (2-d-1); Sulfur-containing compound represented by formula (2) in which "a" is 0, $X_1$ and $X_2$ are each a sulfur atom, and "k" and "l" are each 1]

A glass-made reactor (inside volume: 500 mL) equipped with a stirrer and condenser was charged with 46.0 g (0.60 mol) of thiourea and 194.7 g of 18% hydrochloric acid (0.96 mol as hydrogen chloride), which were mixed with each other with stirring. Then, 72.9 g (0.40 mol) of 2-mercaptomethyl-4-hydroxymethyl-1,3-dithiolan prepared in EXAMPLE 23 was added dropwise to the above mixture at 60° C. in 35 minutes, and the reaction was allowed to proceed at 80° C. for 4 hours to produce a thiuronium salt. After the reaction solution was confirmed to contain no hydroxy compound as the starting compound by high performance liquid chromatography, 267 g of a 30% aqueous solution of sodium hydroxide (2.0 mols as sodium hydroxide) was added to the solution at 50° C. in 10 minutes, to hydrolyze the thiuronium salt at 50° C. for 2 hours. The resultant solution was neutralized with 324.4 g of 18% hydrochloric acid (1.6 mols as hydrogen chloride) and extracted with 200 g of toluene. The separated toluene phase was washed with water until the aqueous phase turned neutral. The toluene phase was separated and distilled at 40° C. under a vacuum, to obtain a lightly yellowish, transparent liquid as a crude product. The crude product was purified by silica gel column chromatography (solvent: toluene), to obtain 63.5 g (0.32 mol, yield: 80%) of 2,4-bismercaptomethyl-1,3-dithiolan, which was a colorless liquid.

Purity: >99% (determined by the area method of high performance liquid chromatography) 270 MHz $^1$H-NMR δ (CDCl$_3$); 1.60 to 1.75 (dt, 1H), 1.85 to 1.95 (dt, 1H), 2.75 to 3.00 (m, 4H), 3.20 to 3.40 (m, 2H), 3.80 to 3.95 (m, 1H), 4.50 to 4.65 (dt, 1H) EI-MS: 198(M)

EXAMPLE 27

[Synthesis of Example Compound No. 1-d-1; Compound represented by formula (1) in which "a" is 0, $R_2$ and $R_3$ are each a hydrogen atom, and "k" and "l" are each 1]

First, 40.0 g (0.31 mol) of 3-chloropropionic acid chloride was added dropwise to a solution of 25.7 g (0.13 mol) of 2,4-bismercaptomethyl-1,3-dithiolan, prepared in REFERENCE SYNTHESIS EXAMPLE 2, dissolved in 78 g of toluene at 100° C. in 15 minutes. They were allowed to react at 110° C. for 6 hours, with stirring. The reaction mixture was cooled to 25° C., to which 437 g of a 5% aqueous solution of sodium hydrogen carbonate (0.26 mol as sodium hydrogen carbonate) was added. The resultant mixture was stirred for 30 minutes, and treated with 132 g of toluene for extraction. The extract organic phase (toluene solution) was washed with 260 g of pure water until the aqueous phase turned neutral, and the organic phase was separated out. It was distilled under a vacuum to be concentrated while removing toluene, to obtain 52.1 g of 2,4-bis(3-chloropropionylthiomethyl)-1,3-dithiolan, a lightly yellowish, transparent liquid as a crude product.

Next, 40.0 g (0.39 mol) of triethylamine was added dropwise to a solution of 52.1 g of 2,4-bis(3-chloropropionylthiomethyl)-1,3-dithiolan prepared above and dissolved in 195 g of acetone at 2 to 50° C. in 1 hour. They were allowed to react at the same temperature for 1.5 hours, with stirring, to which 520 g of water was added. The resultant mixture was treated with 520 g of toluene to extract the reaction product. The extract organic phase (toluene solution) was washed with water until the aqueous phase turned neutral. Then, the organic phase was separated out, incorporated with 0.12 g of 4-methoxyphenol as a polymerization inhibitor, and distilled under a vacuum to be concentrated while removing toluene, to obtain a lightly yellowish, transparent liquid as the crude product. The crude product thus prepared was purified by silica gel column chromatography (developing solvent: hexane/ethyl acetate mixture), to obtain 24.6 g (0.10 mol) of 2,4-bis(acryloylthiomethyl)-1,3-dithiolan.

Yield: 77%. Purity: >99% (determined by the area method of high performance liquid chromatography), 270 MHz $^1$H-NMR δ (CDCl$_3$); 3.10 to 3.50 (m, 6H), 3.85 to 4.05 (m, 1H), 4.55 to 4.75 (dt, 1H), 5.65 to 5.80 (dd, 2H), 6.30 to 6.45 (d, 4H) EI-MS: 306(M)

◊ Production of the Polymerizable Composition Containing the Acrylic Ester Compound of the Present Invention Represented by Formula (1-d), and of the Cured Product or Optical Component by Curing the Same Composition

EXAMPLE 28

First, 60 mg of 2-hydroxy-2-methyl-1-phenylpropan-1-one (Ciba Geigy's Darocur-1173) as a photopolymerization initiator was added to, well mixed with and dissolved in 30 g of the acrylic ester compound prepared in EXAMPLE 27 (Example Compound No. 1-d-1). Then, the liquid thus prepared was sufficiently degassed under a vacuum, and put in a mold composed of glass molds and a gasket, where it was irradiated with ultraviolet ray emitted from a metal halide lamp (80 W/cm) for 360 seconds to proceed polymerization. After the completion of the polymerization, the cured product was slowly cooled and taken out from the mold, and heat-treated at 80° C. for 1 hour for annealing. It was colorless and transparent, and showed no optical strain. It had a refractive index (nd) of 1.662, Abbe number (vd) of 33.5 and specific gravity of 1.42, and was good in heat resistance having a glass transition temperature (Tg) of 120° C.

EXAMPLE 29

(Fabrication of an Optical Component)

First, 100 mg of 2-hydroxy-2-methyl-1-phenylpropan-1-one (at a content of 0.1% by weight on the total weight of the polymerizable compounds) was added to, well mixed with and dissolved in a mixture of 94 g of the acrylic ester compound prepared in EXAMPLE 27 (Example Compound No. 1-d-1) and 6 g of an epoxy acrylate of bisphenol A diglycidyl ether. Then, the liquid thus prepared was sufficiently degassed under a vacuum, and put in a mold (adjusted to have a minus lens shape) composed of glass molds and a tape, where it was irradiated with ultraviolet ray emitted from a metal halide lamp for 60 seconds. The resultant cured product was heat-treated at 80° C. for 1 hour for annealing. It was left to cool to room temperature, to obtain a colorless, transparent minus lens of 30 mm in diameter and 1.5 mm thick at the center.

The lens was colorless and transparent, and showed no optical strain or striae. It had a refractive index (nd) of 1.655 and Abbe number (vd) of 34. Moreover, it was good in heat resistance (thermal deformation temperature), impact resistance and mechanical strength, and showed good dye-affinity with a known dispersed dye for lenses.

◊ Synthesis of the Sulfur-Containing Compound of the Present Invention Represented by Formula (2-b)

EXAMPLE 30

[Synthesis of Example Compound No. 2-b-1; Compound represented by formula (2-b) in which $R_4$ is a methylene group, "k", "l", "m" and "n" are each 1, and $X_1$ and $X_2$ are each an oxygen atom]

First, 97.0 g of a 28% methanol solution of sodium methoxide (0.50 mol as sodium methoxide) was added to a solution of 61.6 g (0.50 mol) of 2-mercaptomethyl-4-hydroxymethyl-1,3-dithiolan prepared in EXAMPLE 23, dissolved in 100 g of methanol, at 10° C. in 30 minutes. The resultant mixture was stirred at the same temperature for around 30 minutes, to which a solution of 43.5 g (0.25 mol) of dibromomethane dissolved in 100 g of methanol was added at 15° C. for 1 hour. Then, the resultant mixture was stirred at 20° C. for 4 hours, and distilled at 40° C. under a vacuum to remove methanol, after completion of the reaction was confirmed by high performance liquid chromatography. The residue was incorporated with 500 g of chloroform, filtered to remove the precipitated inorganic salt, and washed with water. The organic phase was separated out, and distilled under a vacuum to remove chloroform, to obtain 89.5 g of a crude product as a lightly yellowish, transparent liquid. The crude product thus prepared was purified by silica gel column chromatography (developing solvent: chloroform/methanol: 98/2), to obtain 75.6 g (yield: 80%) of Example Compound No. (2-b-1) represented by the following formula, which was a syrup-like, colorless liquid.

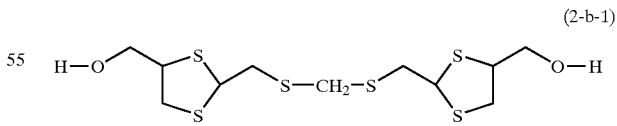

(2-b-1)

EXAMPLE 31

[Synthesis of Example Compound No. (2-b-17); Sulfur-containing compound represented by formula (2-b) in which $R_4$ is a p-xylylene group, "k", "l", "m" and "n" are each 1, and $X_1$ and $X_2$ are each an oxygen atom]

The dihydroxy compound represented by the following formula was prepared as Example Compound No. (2-b-17) in the same manner as in EXAMPLE 30, except 43.5 g (0.25 mol) of dibromomethane was replaced by 43.8 g (0.25 mol) of p-xylylene dichloride.

EI-MS: 466(M)

replaced by Example Compound No. (2-b-17) prepared in EXAMPLE 31.

Purity: >99% (determined by the area method of high performance liquid chromatography) EI-MS: 498(M)

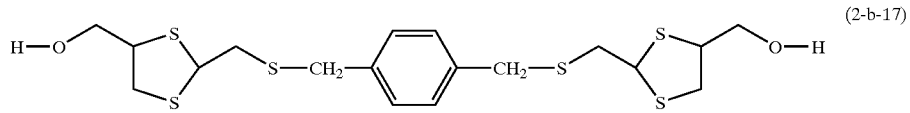

(2-b-17)

EXAMPLE 32

[Synthesis of Example Compound No. (2-b-36); Sulfur-containing compound represented by formula (2-b) in which

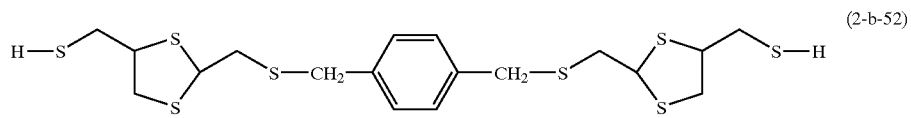

(2-b-52)

$R_4$ is a methylene group, "k", "l", "m" and "n" are each 1, and $X_1$ and $X_2$ are each a sulfur atom]

A glass-made reactor (inside volume: 500 mL) equipped with a stirrer and condenser was charged with 30.8 g (0.405 mol) of thiourea and 109.5 g of 18% hydrochloric acid (0.54 mol as hydrogen chloride), which were mixed with each other with stirring. Then, 52.7 g (0.14 mol) of the dithiol compound [Example Compound No. (2-b-1)] prepared in EXAMPLE 30 was added dropwise to the above mixture at 60° C. in 35 minutes, and the reaction was allowed to proceed at 100° C. for 4 hours to produce a thiuronium salt. After the reaction solution was confirmed to contain no hydroxy compound as the starting compound by high performance liquid chromatography, 173 g of a 25% aqueous solution of sodium hydroxide (1.08 mols as sodium hydroxide) was added thereto at 25° C. in 10 minutes, to hydrolyze the thiuronium salt at 100° C. for 1 hour. The resultant solution was cooled to 25° C., filtered to remove the insolubles, neutralized with 137 g of 18% hydrochloric acid (0.676 mol as hydrogen chloride), extracted with 500 g of chloroform, and washed with water. The organic phase was separated out and distilled at 40° C. under a vacuum, to obtain a crude product. It was purified by silica gel column chromatography (developing solvent: chloroform/hexane: 60/40), to obtain 45.8 g (yield: 80%) of Example Compound No. (2-b-36) represented by the following formula, which was a colorless, transparent, oily liquid.

Purity: >99% (determined by the area method of high performance liquid chromatography) EI-MS: 408(M)

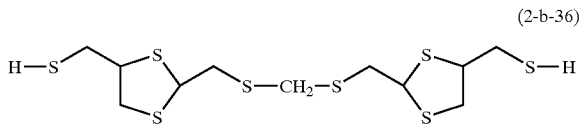

(2-b-36)

EXAMPLE 33

[Synthesis of Example Compound No. (2-b-52); Sulfur-containing compound represented by formula (2-b) in which $R_4$ is a xylylene group, "k", "l", "m" and "n" are each 1, and $X_1$ and $X_2$ are each a sulfur atom]

The dithiol compound represented by the following formula (2-b-52) was prepared in the same manner as in EXAMPLE 32, except the dithiol compound [Example Compound No. (2-b-1)] prepared in EXAMPLE 30 was ◇ Synthesis of the Acrylic Ester Compound Represented by Formula (1-b)

EXAMPLE 34

[Synthesis of Example Compound No. 1-b-11; Acrylic ester compound represented by formula (1-b) in which $R_4$ is a methylene group, $R_2$ and $R_3$ are each a hydrogen atom, "k", "l", "m" and "n" are each 1, and $X_1$ and $X_2$ are each a sulfur atom]

First, 40.0 g (0.31 mol) of 3-chloropropionic acid chloride was added dropwise to a solution of 53.0 g (0.13 mol) of the dithiol compound [Example Compound No. (2-b36)], prepared in EXAMPLE 32, dissolved in 100 g of toluene, at 100° C. in 15 minutes. They were allowed to react at 110° C. for 6 hours with stirring. The reaction mixture was cooled to 25° C., to which 437 g of a 5% aqueous solution of sodium hydrogen carbonate (0.26 mol as sodium hydrogen carbonate) was added. The resultant mixture was stirred for 30 minutes, and treated with 132 g of toluene for extraction. The extract organic phase (toluene solution) was washed with 260 g of pure water until the aqueous phase turned neutral. The organic phase was separated out and distilled under a vacuum to be concentrated while removing toluene, to obtain a crude product of bis[4-(3-chloropropionylthiomethyl)-1,3-dithiolan-2-ylmethylthio] methane, which was a lightly yellowish, transparent liquid.

Next, 40.0 g (0.39 mol) of triethylamine was added dropwise to a solution of 76.7 g of bis[4-(3-chloropropionylthiomethyl)-1,3-dithiolan-2-ylmethyl-thio] methane prepared above, dissolved in 300 g of acetone, at 2 to 5° C. in 1 hour. They were allowed to react at the same temperature for 1.5 hours, with stirring, to which 520 g of water was added. The resultant mixture was treated with 520 g of toluene to extract the reaction product. The extract organic phase (toluene solution) was washed with pure water until the aqueous phase turned neutral. Then, the organic phase was separated out, incorporated with 0.12 g of 4-methoxyphenol as a polymerization inhibitor, and distilled under a vacuum to be concentrated while removing toluene, to obtain a crude product as a lightly yellowish, transparent liquid. The crude product thus prepared was purified by silica gel column chromatography (developing solvent: hexane/ethyl acetate mixture), to obtain 51.6 g (0.10 mol) of bis[4-(acryloylthiomethyl)-1,3-dithiolan-2-ylmethylthio] methane, which was a colorless, transparent liquid.

Purity: >99% (determined by the area method of high performance liquid chromatography) 270 MHz $^1$H-NMR δ

(CDCl$_3$); 3.10 to 3.50 (m, 12H), 3.85 to 4.05 (m, 2H), 4.55 to 4.75 (dt, 4H), 5.65 to 5.80 (dd, 2H), 6.30 to 6.45 (d, 4H) EI-MS: 516(M)

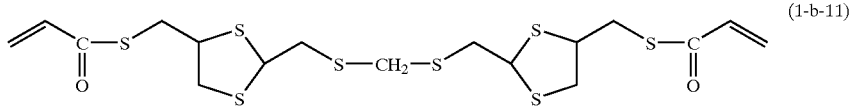

(1-b-11)

EXAMPLE 35

Synthesis of Example Compound No. (1-b-15); Acrylic Ester Compound Represented by Formula (1-b) in which $R_4$ is a Xylylene Group, "k", "l", "m" and "n" are each 1, and $X_1$ and $X_2$ are Each a Sulfur Atom]

1,4-Bis[4-(acryloylthiomethyl)-1,3-dithiolan-2-ylmethylthiomethyl]benzene, a colorless, transparent liquid, was prepared in the same manner as in EXAMPLE 34, except the dithiol compound [Example Compound No. (2-b-36)] prepared in EXAMPLE 32 was replaced by Example Compound No. (2-b-52) prepared in EXAMPLE 33.

Purity: >99% (determined by the area method of high performance liquid chromatography) 270 MHz $^1$H-NMR δ (CDCl$_3$); 3.10 to 3.50 (m, 12H), 3.85 to 4.05 (m, 2H), 4.10 to 4.35 (m, 4H), 4.55 to 4.75 (dt, 2H), 5.65 to 5.80 (dd, 2H), 6.30 to 6.45 (d, 4H), 7.05 to 7.35 (m, 4H) EI-MS: 606(M)

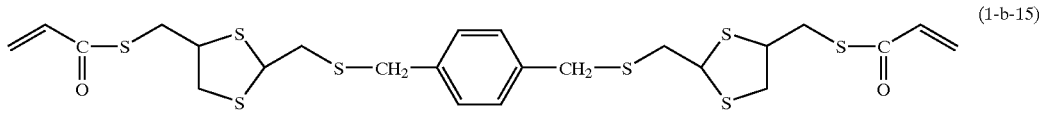

(1-b-15)

◊ Production of the Polymerizable Composition Containing the Acrylic Ester Compound of the Present Invention Represented by Formula (1-b), and of the Cured Product or Optical Component by Curing the Same Composition

EXAMPLE 36

First, 60 mg of 2-hydroxy-2-methyl-1-phenylpropan-1-one ("Darocur-1173", Ciba Geigy's product name) as a photopolymerization initiator was added to, well mixed with and dissolved in 30 g of the acrylic ester compound prepared in EXAMPLE 34 (Example Compound No. 1-b-11). Then, the liquid thus prepared was sufficiently degassed under a vacuum, and put in a mold composed of glass molds and a gasket, where it was irradiated with ultraviolet ray emitted from a metal halide lamp (80 W/cm) for 360 seconds to proceed polymerization. After the completion of the polymerization, the cured product was slowly cooled and taken out from the mold, and heat-treated at 80° C. for 1 hour for annealing. It was colorless and transparent, and showed no optical strain.

It had a refractive index (nd) of 1.685, Abbe number (vd) of 34.0 and specific gravity of 1.40, and was good in heat resistance having a glass transition temperature (Tg) of 80° C. or higher.

EXAMPLE 37

The polymerizable composition and cured (polymerized) product thereof were prepared in the same manner as in EXAMPLE 36, except that 30 g of the acrylic ester compound prepared in EXAMPLE 34 (Example Compound No. 1-b-11) was replaced by 30 g of the one prepared in EXAMPLE 35 (Example Compound No. 1-b-15).

The cured product had a refractive index (nd) of 1.683, Abbe number (vd) of 31.5 and specific gravity of 1.40, and was good in heat resistance having a glass transition temperature (Tg) of 80° C. or higher.

EXAMPLE 38

(Fabrication of an Optical Component)

First, 100 mg of 2-hydroxy-2-methyl-1-phenylpropan-1-one (at a content of 0.1% by weight on the total weight of the polymerizable compounds) was added to, well mixed with and dissolved in a mixture of 90 g of the acrylic ester compound prepared in EXAMPLE 34 (Example Compound No. 1-b-11) and 6 g of an epoxy methacrylate of bisphenol A diglycidyl ether. Then, the liquid thus prepared was sufficiently degassed under a vacuum, and put in a mold (adjusted to have a minus lens shape) composed of glass molds and a tape, where it was irradiated with ultraviolet ray emitted from a metal halide lamp for 60 seconds. The resultant cured product was heat-treated at 80° C. for 1 hour for annealing. It was left to cool to room temperature, to obtain a colorless, transparent minus lens of 30 mm in diameter and 1.5 mm thick at the center.

The lens was colorless and transparent, and showed no optical strain or striae. It had a refractive index (nd) of 1.673 and Abbe number (vd) of 34.5. Moreover, it was good in heat resistance (thermal deformation temperature), impact resistance and mechanical strength, and showed no problem associated with dye-affinity with a known dispersed dye for dyeing lenses.

EXAMPLE 39

A lens was fabricated in the same manner as in EXAMPLE 38, except that the acrylic ester compound prepared in EXAMPLE 34 (Example Compound No. 1-b-11) was replaced by of the one prepared in EXAMPLE 35 (Example Compound No. 1-b-15). The lens was colorless and transparent, and showed no optical strain or striae. It had a refractive index (nd) of 1.673 and Abbe number (vd) of 32.0. Moreover, it was good in heat resistance (thermal deformation temperature) and impact resistance, and showed no problem associated with dye-affinity with a known dispersed dye for dyeing lenses.

◊ Synthesis Examples of the Compounds Represented by Formulae (3), (2-c) and (1-c)

EXAMPLE 40

[Synthesis of Example Compound No., 3-1, Compound represented by formula (3) in which "b" is 1, and $X_3$ is a bromine atom]

A glass-made reactor (inside volume: 500 mL) equipped with a stirrer was charged with 33.48 g (0.270 mol) of 2,3-dimercapto-1-propanol, 10 mL of a boron trifluoride ether complex and 100 g of toluene, to which 54.20 g (0.275 mol) of bromoacetoaldehyde diethylacetal was added at 20° C. in 1 hour, and the reaction was allowed to proceed at 20° C. for 5 hours. Then, 150 g of ice water and 50 g of toluene were added to the above reaction mixture. The resultant mixture was stirred for 15 minutes, and allowed to stand. The toluene phase was separated out, and washed with an alkali (150 g of a 3% aqueous solution of sodium hydrogen carbonate) and then with water until the aqueous phase turned neutral. The toluene phase was separated out and distilled at 40° C. under a vacuum, to obtain a crude product as a lightly yellowish, transparent liquid. It was purified by silica gel column chromatography, to obtain 49.46 g (0.216 mol) of 2-(2'-bromomethyl)-4-hydroxymethyl-1,3-dithiolan.

Yield: 80%, Purity: >99% (determined by the area method of high performance liquid chromatography) FD-MS: 228 (M), 230 (M+2)

EXAMPLE 41

[Synthesis of Example Compound No., 2-C-1, Compound represented by formula (2-c) in which "l" is 1, and $X_2$ is an oxygen atom]

A glass-made reactor (inside volume: 100 mL) equipped with a stirrer was charged with 22.90 g (0.10 mol) of 2-(2'-bromomethyl)-4-hydroxymethyl-1,3-dithiolan prepared in EXAMPLE 40, 13.6 g (0.20 mol) of sodium formate and 1.61 g (0.005 mol) of tetramethyl ammonium bromide, and the resultant mixture was stirred under heating at 110° C. for 1.5 hours. After the completion of the reaction, 8.8 g of a 50% aqueous solution of sodium hydroxide was added dropwise to the above reaction mixture in 15 minutes. The reaction product was extracted with toluene and washed with water. The extract was distilled at 40° C. under a vacuum, to remove toluene. This produced a crude product as a lightly yellowish, transparent liquid. It was purified by silica gel column chromatography, to obtain 13.28 g of 2-(2'-hydroxymethyl)-4-hydroxymethyl-1,3-dithiolan.

Yield: 80%, Purity: >99% (determined by the area method of high performance liquid chromatography) FD-MS: 166 (M)

EXAMPLE 42

[Synthesis of Example Compound No. 1-C-1, Compound represented by formula (1-c) in which $R_2$ and $R_3$ are each a hydrogen atom, "l" is 1, and $X_2$ is, an oxygen atom]

2-Acryloyloxymethyl-4-acryloyloxymethyl-1,3-dithiolan as a colorless, transparent liquid was prepared in the same manner as in EXAMPLE 24, except that 2-mercaptomethyl-4-hydroxymethyl-1,3-dithiolan was replaced by 2-(2'-hydroxymethyl)-4-hydroxymethyl-1,3-dithiolan prepared in EXAMPLE 41.

Purity: >99% (determined by the area method of high performance liquid chromatography) FD-MS: 274(M)

COMPARATIVE EXAMPLE 1

A polymerizable composition was prepared and lens was fabricated in the same manner as in EXAMPLE 21, except that 24 g of 2,5-bis(acryloyloxyethylthiomethyl)-1,4-dithian, a known acrylic ester disclosed by Japanese Patent Publication No. 4-161410, instead of the acrylic ester of the present invention as a polymerizable compound represented by formula (1) and 6 g of dimethyloltricyclodecane acrylate were used. The lens was colorless and transparent, and had a refractive index (nd) of 1.61 and Abbe number (vd) of 42.

COMPARATIVE EXAMPLE 2

A polymerizable composition was prepared and lens was fabricated in the same manner as in EXAMPLE 21, except that 24 g of 1,4-bis(2-methacryloyloxy-ethylthio)xylylene, a known methacrylic ester disclosed by Japanese Patent Pub lication No. 3-217412, and 6 g of 2,2-bis(4-methacryloyloxyethoxyphenyl)propane instead of the sulfur-containing (meth)acrylic ester of the present invention as a polymerizable compound represented by formula (1), were used. The lens was colorless and transparent, and had a refractive index (nd) of 1.59 and Abbe number (vd) of 39.

Use of the polymerizable composition containing the acrylic ester compound of the present invention allows the polymerization and molding/curing in a short time, to produce optical components, e.g., plastic lenses typified by vision-correcting lenses efficiently. The cured product and optical components produced from the polymerizable composition have a higher refractive index than a known photopolymerizable resin, involving no problem with respect to transparency and Abbe number. They also have practically sufficient characteristics with respect to thermal characteristics (e.g., thermal deformation temperature) and mechanical characteristics (e.g., impact resistance).

Possibility of Industrial Utilization

The acrylic ester compound of the present invention is useful for various purposes, e.g., optical and dental materials, as a monomer for polymerizable compositions capable of starting to polymerize by the aid of light, and curable and moldable.

The cured product or optical component of the present invention can be produced efficiently in a short time by photopolymerization or the like; is high in refractive index and good in optical characteristics (e.g., transparency and Abbe number), thermal characteristics (e.g., thermal deformation temperature) and mechanical characteristics (e.g., impact resistance); and hence is useful for various purposes, e.g., various types of plastic lenses typified by vision-correcting spectacles lenses, transparent substrates for optical information recording media and liquid crystal cells, various transparent coating materials, e.g., those for anti-reflective coating, various transparent sealants, e.g., those for light-emitting diodes (LEDs), and dental materials.

Moreover, the sulfur-containing compound of the present invention represented by formula (2), is useful as a synthesis intermediate for the acrylic ester compound represented by formula (1).

What is claimed is:

1. An acrylic ester compound represented by formula (1):

(1)

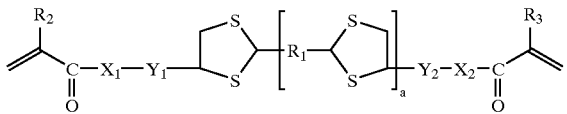

(wherein "a" is an integer of 0 to 4;

$R^1$ is a directly bonded single bond, an alkylene group which may have a substituent, an aralkylene group which may have a substituent, an arylene group which may have a substituent, or a —$Y_3$—S—$R_4$—S—$Y_4$— group;

$R_2$ and $R_3$ are each a hydrogen atom or an alkyl group; $X_1$ and $X_2$ are each an oxygen atom or a sulfur atom; $Y_1$ and $Y_2$ are each an alkylene group which may contain an oxygen atom or a sulfur atom; and $R_4$ in the —$Y_3$—S—$R_4$—S—$Y_4$— group is an alkylene group, an aralkylene group or an arylene group, and $Y_3$ and $Y_4$ in the —$Y_3$—S—$R_4$—S—$Y_4$— group are each independently an alkylene group).

2. The acrylic ester compound according to claim 1, wherein in formula (1), "a" is 1; $R_1$ is a directly bonded single bond, an alkylene group which may have a substituent, an aralkylene group which may have a substituent, an arylene group which may have a substituent or a —$(CH_2)_m$—S—$R_4$—S—$(CH_2)_n$— group [wherein "m" and "n" are each an integer of 1 to 4]; and $Y_1$ is a —$(CH_2)_k$— group and $Y_2$ is a —$(CH_2)_l$— group ("k" and "l" are each an integer of 1 to 4).

3. The acrylic ester compound according to claim 1, wherein in formula (1), "a" is 0; and $Y_1$ is a —$(CH_2)_k$— group and $Y_2$ is a —$(CH_2)_l$— group ("k" and "l" are each an integer of 1 to 4).

4. The acrylic ester compound according to claim 2, wherein the compound represented by formula (1) is represented by formula (1-a):

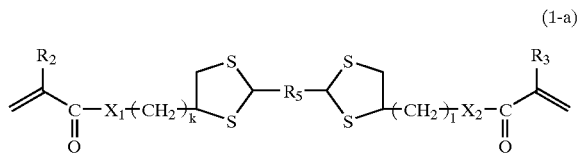

(1-a)

(wherein $R_5$, which is similar to $R_1$, is a directly bonded single bond, an alkylene group which may have a substituent, an aralkylene group which may have a substituent, or an arylene group which may have a substituent; and $R_2$, $R_3$, $X_1$, $X_2$, "k" and "l" are same meanings as described above).

5. The acrylic ester compound according to claim 2, wherein the compound represented by formula (1) is a compound represented by formula (1-b):

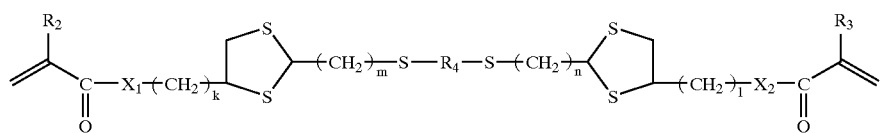

(1-b)

(wherein $R_2$, $R_3$, $R_4$, $X_1$, $X_2$, "k", "l", "m" and "n" are same meanings as described above).

6. The acrylic ester compound according to claim 3, wherein the compound represented by formula (1) is a compound represented by formula (1-c):

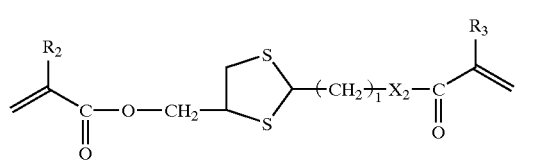

(1-c)

(wherein $R_2$, $R_3$, $X_2$ and "l" are same meanings as described above).

7. The acrylic ester compound according to claim 3, wherein the compound represented by formula (1) is a compound represented by formula (1-d):

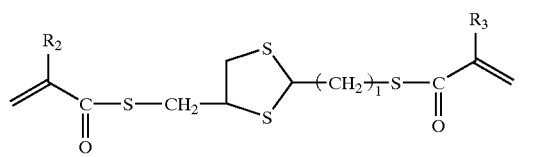

(1-d)

(wherein $R_2$, $R_3$ and "l" are same meanings as described above).

8. A polymerizable composition containing the acrylic ester compound according to claim 1.

9. A cured product obtained by polymerizing the polymerizable composition according to claim 8.

10. An optical component comprising the cured product according to claim 9.

11. A process for producing the acrylic ester compound represented by formula (1) of claim 1 in accordance with acrylate-esterification of a sulfur-containing compound represented by formula (2);

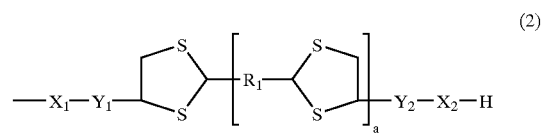

(2)

(wherein "a", $R_1$, $X_1$, $X_2$, $Y_1$ and $Y_2$ are same meanings as described above).

12. The production process according to claim 11, wherein the acrylate-esterification is effected by reacting the compound represented by formula (2) with a halopropionic acid or its acid halide to convert it into a halopropionate ester compound, and then by dehydrohalogenating the halopropionate ester compound into the acrylic ester.

13. The process for producing the acrylic ester compound according to claim 11, wherein the compound represented by formula (2) is a compound represented by formula (2-a):

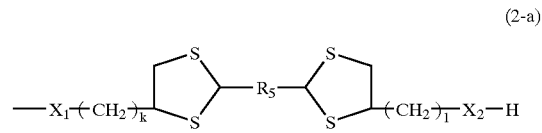

(2-a)

(wherein $R_5$ is a directly bonded single bond, an alkylene group which may have a substituent, an aralkylene group which may have a substituent, or an arylene group which may have a substituent; "k" and "l" are each an integer of 1 to 4; and $X_1$ and $X_2$ are each an oxygen atom or a sulfur atom).

14. The process for producing the acrylic ester compound according to claim 11, wherein the compound represented by formula (2) is a compound represented by formula (2-b):

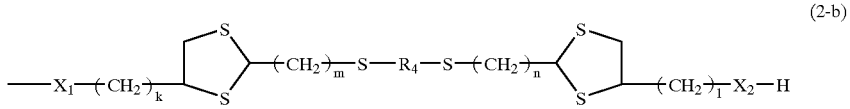
(2-b)

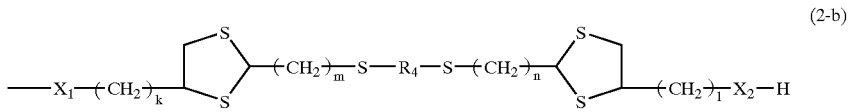
(2-b)

(wherein $R_4$ is an alkylene, an aralkylene or an arylene group; "k", "l", "m" and "n" are each an integer of 1 to 4; and $X_1$ and $X_2$ are each an oxygen atom or a sulfur atom).

15. The process for producing the acrylic ester compound according to claim 11, wherein the compound represented by formula (2) is a compound represented by formula (2-c):

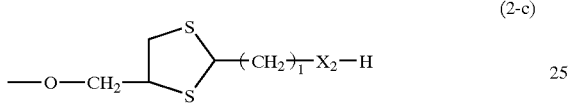
(2-c)

(wherein $X_2$ is an oxygen atom or a sulfur atom; and "l" is an integer of 1 to 4).

16. The process for producing the acrylic ester compound according to claim 11, wherein the compound represented by formula (2) is a compound represented by formula (2-d):

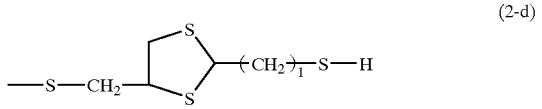
(2-d)

(wherein "l" is an integer of 1 to 4).

17. A sulfur-containing compound represented by formula (2-a):

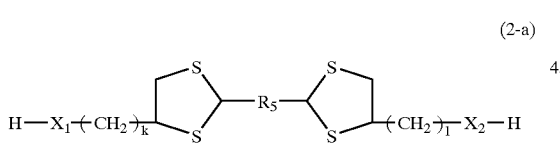
(2-a)

(wherein $R_1$ is a directly bonded single bond, an alkylene group which may have a substituent, an aralkylene group which may have a substituent, or an arylene group which may have a substituent; "k" and "l" are each an integer of 1 to 4; and $X_1$ and $X_2$ are each an oxygen atom or a sulfur atom).

18. A sulfur-containing compound represented by formula (2-b):

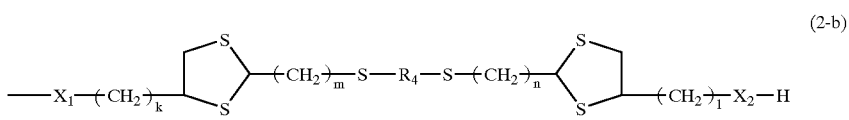
(2-b)

(wherein $R_4$ is an alkylene, aralkylene or arylene group; "k", "l", "m", and "n" are each an integer of 1 to 4; and $X_1$ and $X_2$ are each an oxygen atom or a sulfur atom).

19. A sulfur-containing compound represented by formula (2-c):

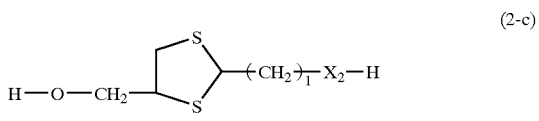
(2-c)

(wherein $X_2$ is an oxygen atom or a sulfur atom; and "l" is an integer of 1 to 4).

20. A sulfur-containing compound represented by formula (3):

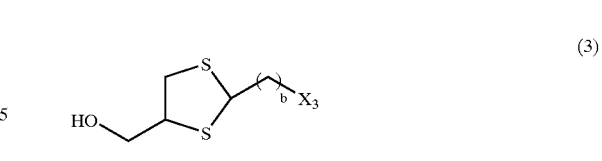
(3)

(wherein $X_3$ is a halogen atom; and "b" is an integer of 1 to 4).

* * * * *